(12) United States Patent
Malhotra et al.

(10) Patent No.: US 11,730,705 B2
(45) Date of Patent: Aug. 22, 2023

(54) SMALL MOLECULE CMKLR1 ANTAGONISTS IN INFLAMMATORY DISEASE

(71) Applicants: The Board of Trustees of the Leland Stanford Junior University, Stanford, CA (US); The United States Government As Represented By The Department of Veterans Affairs, Washington, DC (US)

(72) Inventors: Sanjay Malhotra, Palo Alto, CA (US); Vineet Kumar, Palo Alto, CA (US); Melissa LaJevic, Mountain View, CA (US); Mallesh Pandrala, Palo Alto, CA (US); Brian A. Zabel, Redwood City, CA (US)

(73) Assignees: The Board of Trustees of the Leland Stanford Junior University, Stanford, CA (US); The United States Government As Represented By The Department of Veterans Affairs, Washington, DC (US)

( * ) Notice: Subject to any disclaimer, the term of this patent is extended or adjusted under 35 U.S.C. 154(b) by 409 days.

(21) Appl. No.: 16/847,186

(22) Filed: Apr. 13, 2020

(65) Prior Publication Data

US 2020/0345661 A1 Nov. 5, 2020

Related U.S. Application Data

(60) Provisional application No. 62/841,990, filed on May 2, 2019.

(51) Int. Cl.
*A61K 31/135* (2006.01)
*A61P 17/06* (2006.01)
*A61K 31/14* (2006.01)
*A61K 31/133* (2006.01)
*A61P 25/28* (2006.01)

(52) U.S. Cl.
CPC .......... *A61K 31/135* (2013.01); *A61K 31/133* (2013.01); *A61K 31/14* (2013.01); *A61P 17/06* (2018.01); *A61P 25/28* (2018.01)

(58) Field of Classification Search
CPC .................................................. A61K 31/135
See application file for complete search history.

(56) References Cited

U.S. PATENT DOCUMENTS 9,265,738 B2 2/2016 Graham et al.
2021/0147558 A1* 5/2021 Poirier .................... A61P 29/00

FOREIGN PATENT DOCUMENTS

| CA | 2851643 A1 | 4/2013 | |
|----|------------|--------|---|
| CN | 104434888 A * | 3/2015 | ............. A61K 31/14 |
| EP | 1632778 A2 | 8/2006 | |
| EP | 2480531 B1 | 5/2014 | |
| EP | 3037401 A2 | 6/2016 | |
| WO | WO2012172336 A2 | 12/2012 | |
| WO | WO-2013109543 A1 * | 7/2013 | ............. A61K 31/12 |

OTHER PUBLICATIONS

Kumar et al., Novel ligands of Choline Acetyltransferase designed by in silico molecular docking, hologram QSAR and lead optimization, Scientific Reports.*
STN document No. 162:468906, Mar. 25, 2015.*

* cited by examiner

*Primary Examiner* — Svetlana M Ivanova
(74) *Attorney, Agent, or Firm* — Pamela J. Sherwood; Bozicevic, Field & Francis LLP

(57) ABSTRACT

α-NETA analogs are provided for the treatment of inflammatory disease.

8 Claims, 14 Drawing Sheets

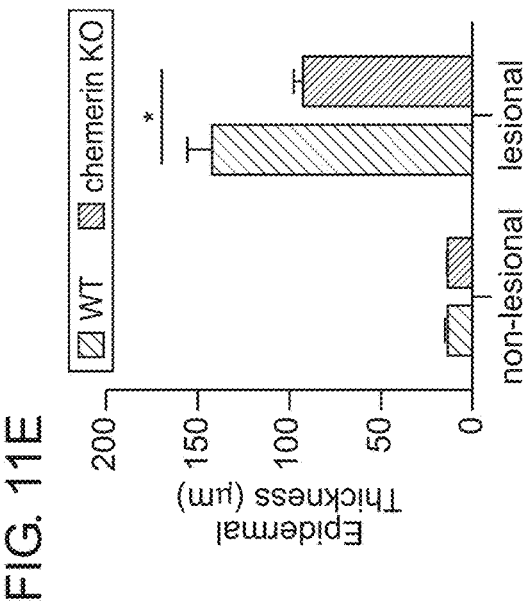
FIG. 11C
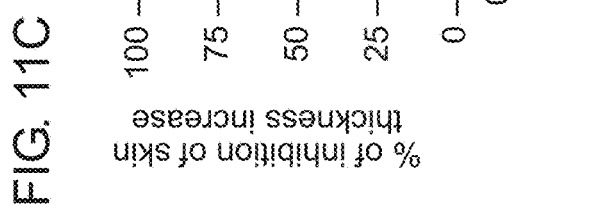
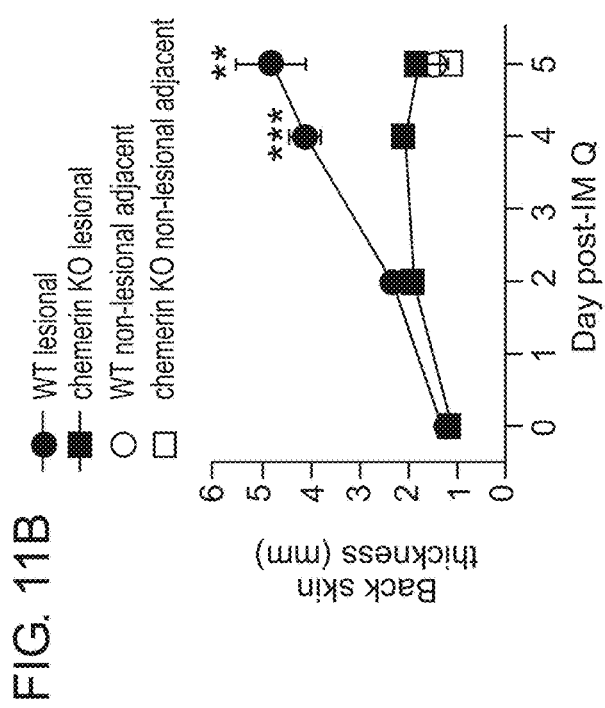
FIG. 11B
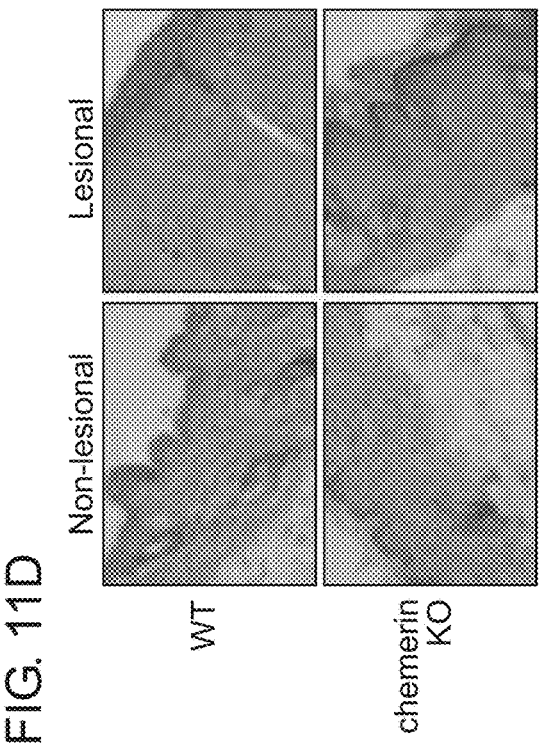
FIG. 11E
FIG. 11D

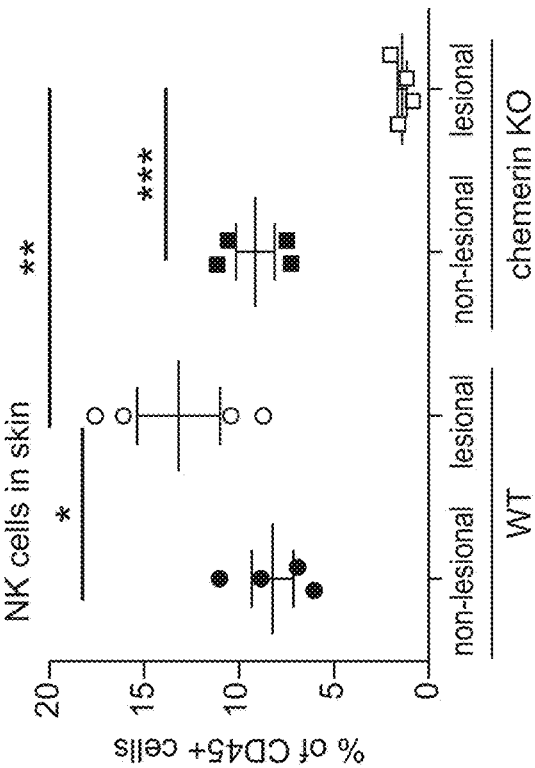
FIG. 11F
FIG. 11G
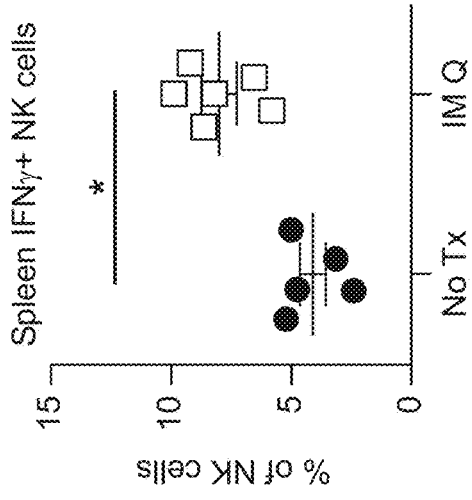
FIG. 12A
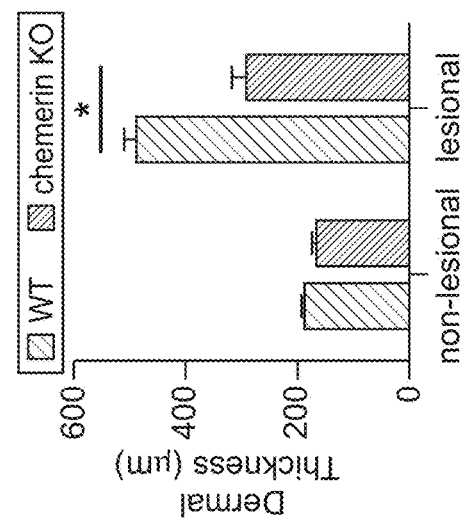
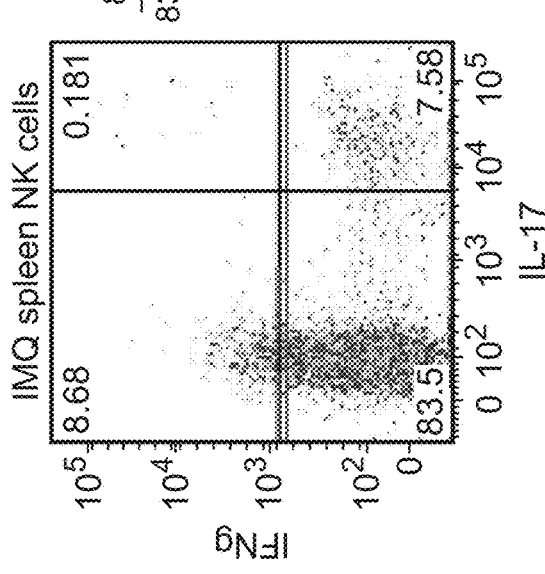
FIG. 12B

Day 4
(peak of disease)

α-NETA
$IC_{50} = 4.9 \pm 1.5 \, \mu M$ $IC_{50} = 11.9 \, \mu M$ $IC_{50} = 5.6 \pm 0.7 \, \mu M$ $IC_{50} = 2.5 \pm 0.8 \, \mu M$

α-NETA
β-arr IC$_{50}$: 4.9 ± 1.5 μM
CTX IC$_{50}$: 37.0 ± 8.9 μM

Cmpd (27)
β-arr IC$_{50}$: 1.9 ± 0.2 μM
CTX IC$_{50}$: 4.5 ± 1.5 μM

Cmpd (6)
β-arr IC$_{50}$: 6.2 ± 2.5 μM
CTX IC$_{50}$: 14.6 ± 4.4 μM

SMALL MOLECULE CMKLR1 ANTAGONISTS IN INFLAMMATORY DISEASE

CROSS REFERENCE

This application claims benefit of U.S. Provisional Application No. 62/841,990, filed May 2, 2019.

INTRODUCTION

Multiple sclerosis (MS) is a disabling demyelinating disease of the central nervous system (CNS) that affects approximately 2.5 million people worldwide. The pathomechanism of MS and its mouse-model counterpart experimental autoimmune encephalomyelitis (EAE) is based on inflammatory autoreactive leukocytes entering the CNS, destroying axonal myelin, and contributing to neurodegeneration. FDA-approved disease modifying therapies such as dimethyl fumarate (Tecfidera) aim to prevent MS relapses and slow neurodegeneration, although the existing medications are only partially effective and can have undesirable side-effects (e.g. lymphopenia, increased susceptibility to opportunistic infections, progressive multifocal leukoencephalopathy). Even though a number of MS treatments are available, due to the heterogeneity of the MS disease process, individual patient responses, and medication toxicities, there remains a substantial unmet clinical need for improved therapies.

Small molecule therapeutics that target leukocyte trafficking pathways can reduce disease activity and improve clinical outcomes in MS. For example, FTY720 (Fingolimod, Gilenya), a small molecule that targets S1P receptors, is an approved treatment for MS that inhibits the migration of autoreactive T cells into the CNS by triggering lymphocyte sequestration in lymph nodes. S1P receptors are expressed on most leukocytes, and thus agents that target S1P receptors may lead to systemic defects in immunity, and incidences of lymphoproliferative disorders have been reported. Agents that selectively target the trafficking of key inflammatory cell subsets involved in the pathophysiology of MS may therefore be superior to current treatment strategies.

Chemokine-like receptor-1 (CMKLR1) is a chemoattractant receptor that binds chemerin, a proteolytically regulated leukocyte chemoattractant. CMKLR1 is expressed by key effector cells in EAE and MS, including macrophages, subsets of dendritic cells (DC), natural killer (NK) cells and microglia. Lande et al. reported chemerin co-localization with intralesional endothelial cells in the brains of MS patients, and identified CMKLR1+ leukocytes in the leptomeninges and in perivascular cuffs of chronic and active MS lesions. In preclinical studies, we showed that CMKLR1-knockout (KO) mice develop less severe clinical and histological EAE than wild-type (WT) mice. We sought to identify CMKLR1 inhibitors to pharmaceutically recapitulate the CMKLR1 KO phenotype in EAE. We identified a lead CMKLR1 antagonist α-NETA, which inhibited chemerin-driven CMKLR1 signaling (β-arrestin2 and chemotaxis) in vitro and suppressed EAE in vivo.

SUMMARY

The present invention is drawn to compositions and methods for interfering with the biological processes associated with CMKLR1 signaling, which processes include, without limitation, regulation of inflammatory diseases, including psoriasis and demyelinating inflammatory disease.

In some embodiments, inhibitors of CMKLR1 are provided, which inhibitors are useful for the treatment or prevention of MS, psoriasis, and other diseases, e.g. experimental animal models such as experimental autoimmune encephalomyelitis (EAE).

In some embodiments a composition comprising a therapeutic α-NETA analog are provided. In some embodiments a formulation of an α-NETA analog are provided. The formulation may comprise an effective dose of the analog and a pharmaceutically acceptable excipient. The formulation maybe prepared for the desired route of administration, e.g. oral, parenteral, topical, etc., usually parenteral. Exemplary inhibitors are disclosed herein and include particularly the structures of FIGS. 7 and 8, and disclosed in the examples.

In some embodiments the therapeutic α-NETA analog is selected from:

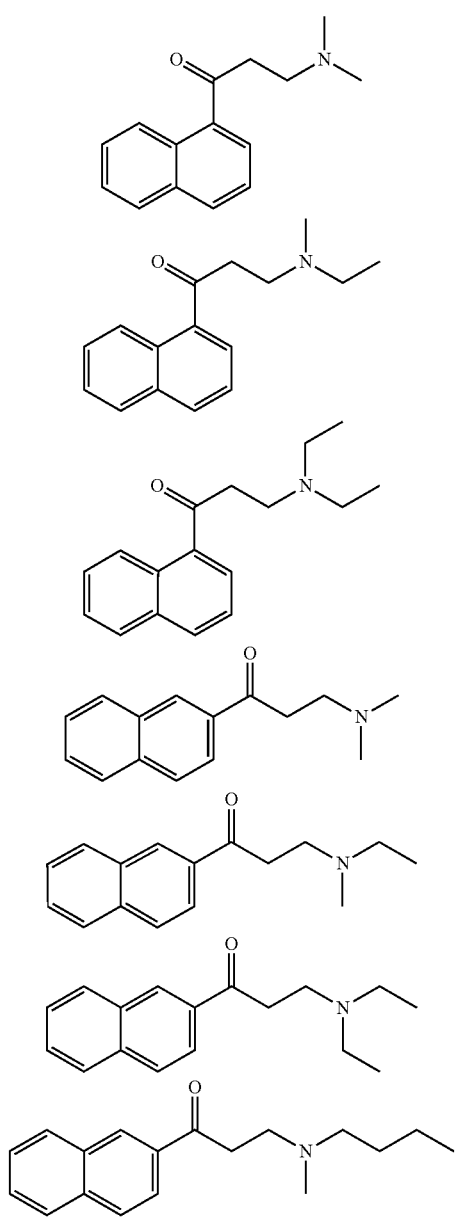

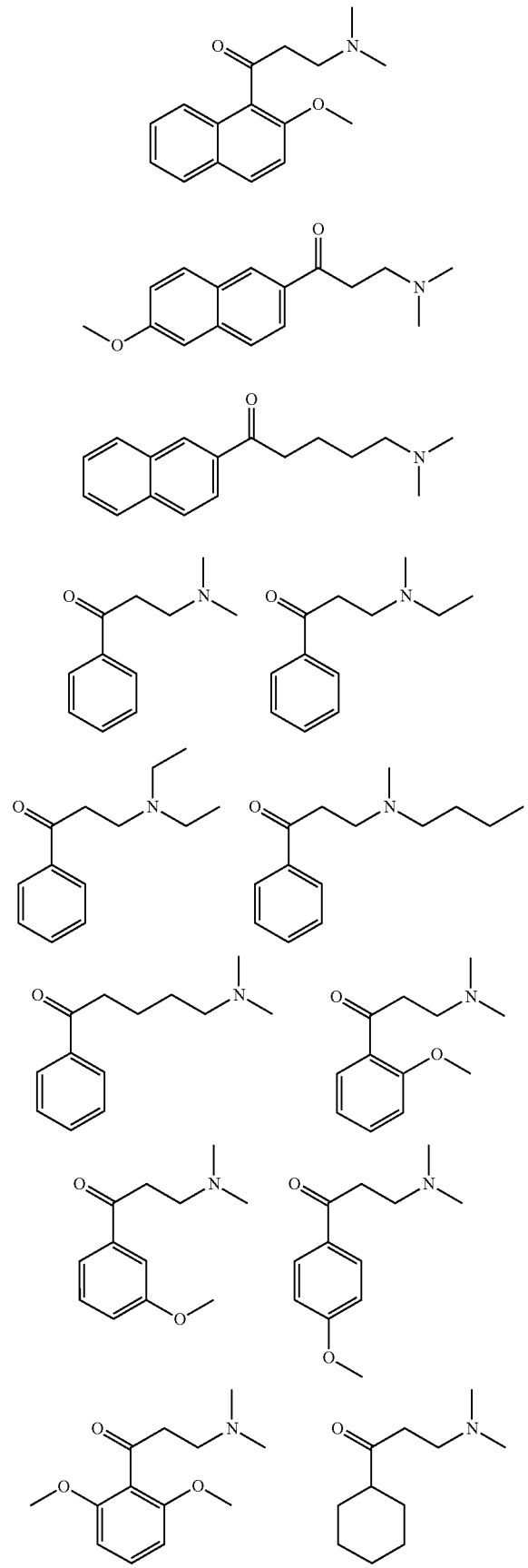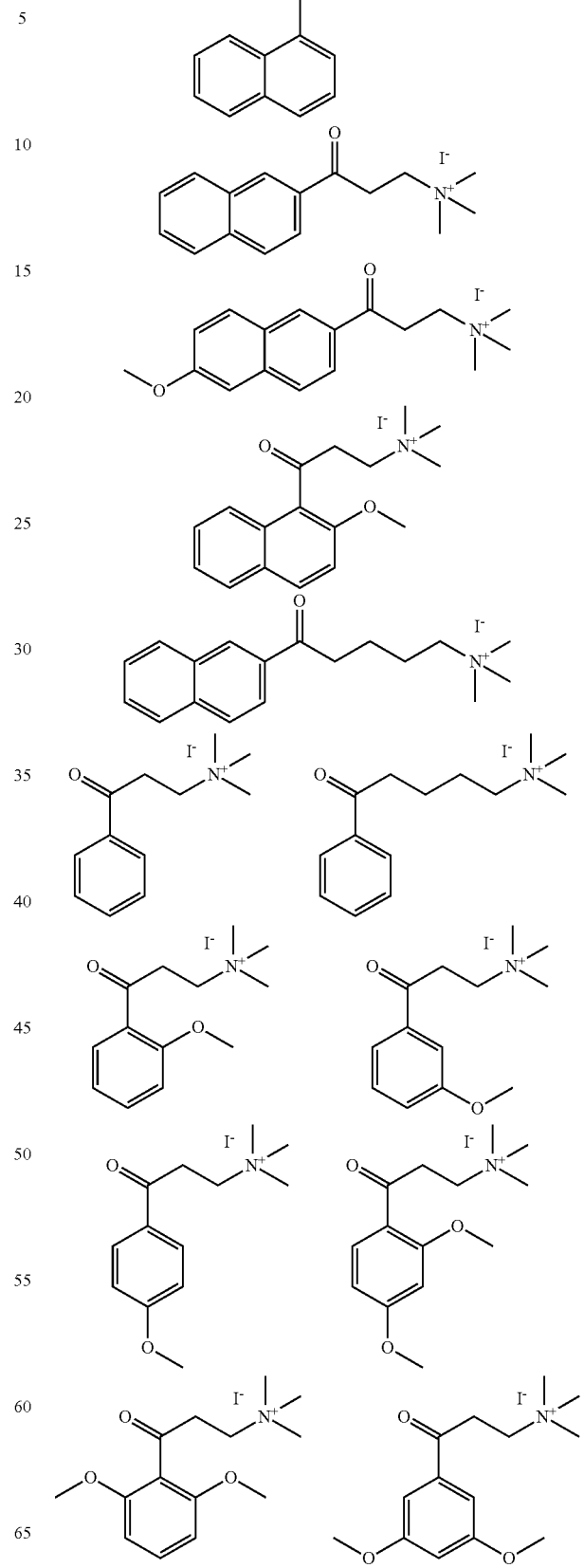

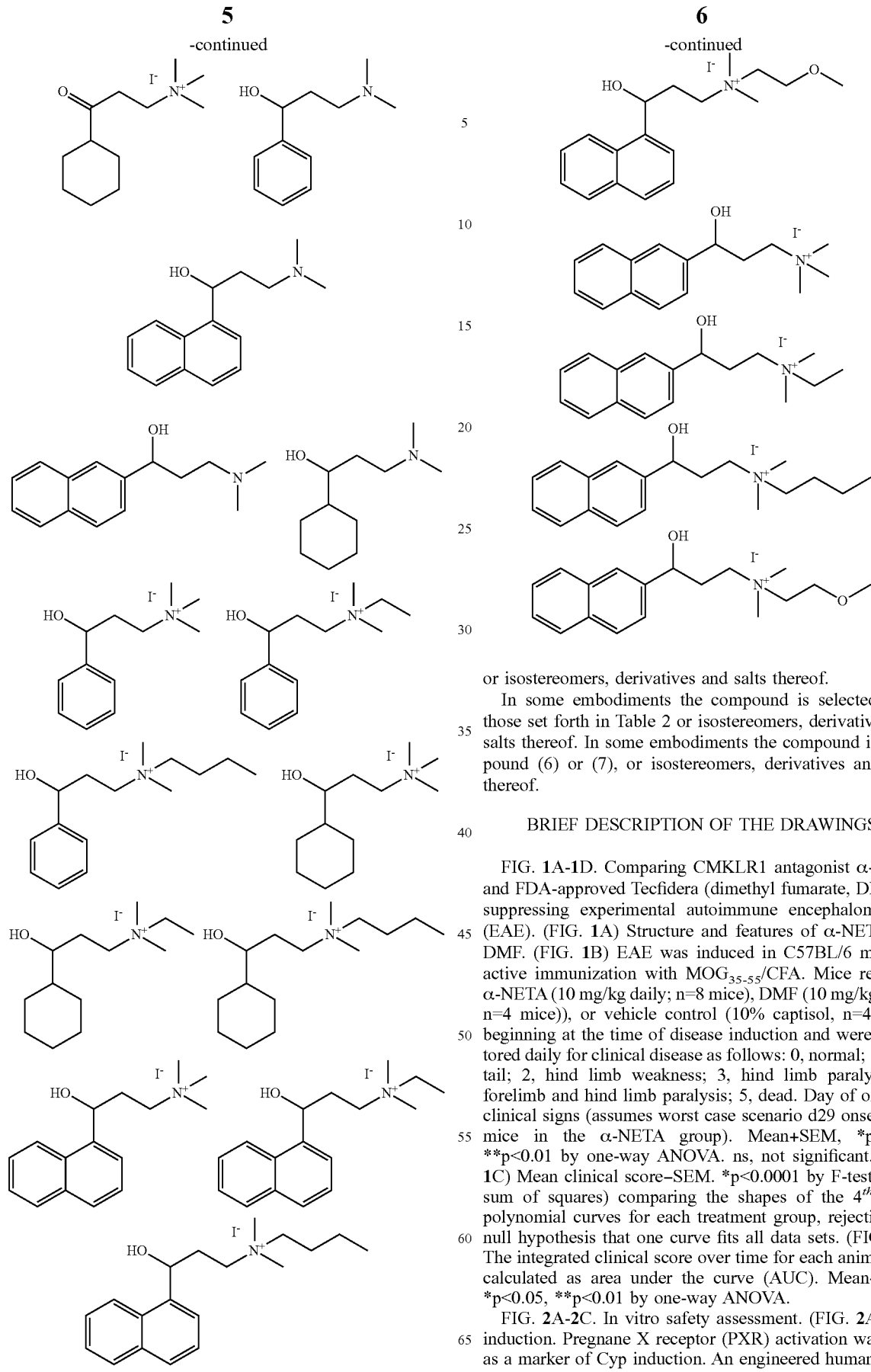

or isostereomers, derivatives and salts thereof.

In some embodiments the compound is selected from those set forth in Table 2 or isostereomers, derivatives and salts thereof. In some embodiments the compound is compound (6) or (7), or isostereomers, derivatives and salts thereof.

BRIEF DESCRIPTION OF THE DRAWINGS

(FIG. 1A) Structure and features of α-NETA and DMF. (FIG. 1B) EAE was induced in C57BL/6 mice by active immunization with $MOG_{35-55}$/CFA. Mice received α-NETA (10 mg/kg daily; n=8 mice), DMF (10 mg/kg daily, n=4 mice)), or vehicle control (10% captisol, n=4 mice) beginning at the time of disease induction and were monitored daily for clinical disease as follows: 0, normal; 1, limp tail; 2, hind limb weakness; 3, hind limb paralysis; 4, forelimb and hind limb paralysis; 5, dead. Day of onset of clinical signs (assumes worst case scenario d29 onset for 2 mice in the α-NETA group). Mean+SEM, *p<0.05, **p<0.01 by one-way ANOVA. ns, not significant. (FIG. 1C) Mean clinical score−SEM. *p<0.0001 by F-test (extra sum of squares) comparing the shapes of the $4^{th}$ order polynomial curves for each treatment group, rejecting the null hypothesis that one curve fits all data sets. (FIG. 1D) The integrated clinical score over time for each animal was calculated as area under the curve (AUC). Mean+SEM, *p<0.05, **p<0.01 by one-way ANOVA.

(FIG. 2A) Cyp induction. Pregnane X receptor (PXR) activation was used as a marker of Cyp induction. An engineered human hepatoma cell line with a PXR luciferase reporter was incubated with the indicated concentrations of α-NETA, Rifampicin (positive control), or DMSO (negative control), and luciferase activity assessed. Mean±range of duplicate wells. (FIG. 2B) hERG inhibition. Patch-clamp assay with single CHO-hERG cell transfectants were used to quantify potential α-NETA-dependent hERG inhibition (2-3 cells per compound concentration). Basal hERG current was measured, α-NETA (0.008, 0.04, 0.2, 1, 5, 25 uM) was added, the cell was depolarized, the hERG tail current was measured, and IC50 determined. Mean+range or SEM displayed. (FIG. 2C) Ames test for genotoxicity. Histidine revertants were quantified following exposure to α-NETA (0.1, 1, 10 uM; 48 wells/dose). Mean number of positive wells+SEM displayed. (−) control: PBS; (+) control: sodium azide.

(FIG. 4A) Mouse body weight was recorded daily and displayed as percent initial weight on d0, mean+SEM, n=3 mice per dose. (FIG. 4B) On day 14, the mice were euthanized and the wet weight of the indicated organs determined and displayed, normalized to body weight. Mean weight+SEM, n=3 mice/dose. No significant differences noted.

(FIG. 10A) Chemerin RNA expression and protein levels were quantified by RT-QPCR and ELISA, respectively, in skin samples on the indicated day post-IMQ application (5% cream, twice daily application). Chemerin RNA expression was normalized to β-actin and expressed as fold change relative to day 0 (no treatment) by the 2-ΔΔCt method. Chemerin protein per μg skin is shown. mean±SEM; n=4 mice/group; *p<0.05 by ANOVA comparing the indicated day vs. day 0. (FIG. 10B) CMKLR1 expression was assessed on blood leukocytes from untreated (No Tx) mice or mice treated with IMQ (24 h). Cells were stained for CMKLR1 (BZ186 mAb, rIgG2a isotype) and various cell surface markers. CMKLR1 was expressed on blood NK cells (CD3-CD19-Gr1-DX5+) from untreated and IMQ-treated mice; CMKLR1 was induced by IMQ on CD3-CD19-DX5-F4/80+ monocytes. Representative flow cytometry plots of pooled WBC from 2 mice shown. (FIG. 10C) CMKLR1-positive blood NK cells migrate to chemerin. Transwell migration of peripheral blood leukocytes isolated 24 h post-IMQ-treatment. After 2 h, the migrated cells were collected and stained for CD3-DX5+NK cells or CD3+13220+T and B cells. For each lymphocyte population the data from 2 experiments was combined and plotted normalized to the maximum migration signal. (+) ctrl=100 nM CXCL12, (−) ctrl=no chemokine. mean±SEM; n=4 wells/condition; *p<0.05 by ANOVA comparing the indicated chemoattractant/concentration vs. (−) ctrl. (FIG. 10D) IMQ-induced Increased percentages of CMKLR1+ blood NK cells and monocytes in vivo. Blood leukocytes were isolated from untreated (Control) mice or 24 h after IMQ treatment. The percent of NK cells or monocytes among total blood leukocytes was determined by flow cytometry. mean±SEM; n=3-4 mice/group; *p<0.05 by t-test for NK cells. n=1-2 mice/group for monocytes (mean±range). (FIG. 10E) NK cells infiltrate the skin in IMQ-treated mice. The number of NK cells (CD45+DX5+CD3−Ly6g−F480−) in the skin of untreated (Control) or IMQ treated (day 5) mice as determined by flow cytometry and normalized to skin sample weight, n=4-6 mice per group; mean±SEM; *p<0.05 by t-test.

FIG. 11A-11G. Chemerin KO mice are protected against IMQ-induced psoriasis. IMQ was applied to the denuded backs of WT and chemerin KO mice twice daily, inducing severe psoriaform lesions in WT mice (redness, flakiness, skin contraction) (FIG. 11A). Chemerin KO mice were protected against IMQ-induced morphological skin changes. Representative images of the same mouse shown over time. (FIG. 11B) Chemerin KO mice were significantly resistant to IMQ-induced increases in back skin thickness as measured by calipers (the back skin was doubled-over for measurements). mean±SEM, n=8 per group, *p<0.05 by 2-tailed t-test comparing WT vs. KO at the indicated timepoints. (FIG. 11C) Comparing the effect of chemerin deficiency versus global immune suppression via steroid dexamethasone in inhibiting IMQ-dependent psoriasis. Mice were treated twice daily with IMQ±dexamethasone (DEX, 200 ug/mouse) 1 h prior to IMQ treatment. The percent inhibition of skin thickening by DEX was plotted for each day; for chemerin deficiency, the percent inhibition could only be determined for day 5 (based on nonlesional skin thickness measurements in (FIG. 11B). mean±SEM, n=5-8 mice per group. (FIG. 11D) Chemerin KO mice were protected against histopathological changes in the skin. H&E stained skin sections show an increase in the epidermis and dermis in IMQ-treated WT mice compared with untreated WT and with IMQ-treated chemerin KO mice. (FIG. 11E) Microscopic measurement of epidermal and (FIG. 11F) dermal thickness was determined on day 5 post-IMQ on histological sections of non-lesional or lesional skin. mean±SEM, n=8 per group, *p<0.05 by 2 tailed t-test. (FIG. 11G) NK cell (CD45+DX5+CD11b-CD3-CD19-) infiltration into lesional or non-lesional adjacent skin was determined by flow cytometry (6 day timepoint) for IMQ-treated WT and chemerin KO mice. mean±SEM, n=4 mice per genotype, *p<0.005 by 2-tailed t-test; p<0.01 by 2-tailed t-test; *p<0.05 by 1-tailed t-test.

FIG. 12A-12E. Chemerin is required for efficient recruitment of pro-psoriatic NK cells into the skin. IMQ-treatment upregulates IFNγ and IL-17 in splenic (systemic) NK cells. (FIG. 12A) Representative intracellular cytokine staining for IFNγ and IL-17 on CD45+CD3-B220-Gr1-DX5+ gated spleen NK cells from IMQ-treated mice (3d post-IMQ treatment). (FIG. 12B, 12C) Quantification of percent of total spleen NK cells positive for IFNγ (FIG. 12B) or IL-17 (FIG. 12C) from untreated (No Tx) or IMQ treated mice; mean±SEM, n=6 mice/condition. *p<0.05 by Student's t-test. (FIG. 12D, 12E) Chemerin is required for efficient recruitment of IFNγ+ and IL-17+NK cells into the skin during experimental psoriasis. Quantification of fold change comparing the percent of total skin infiltrating NK cells positive for IFNγ (FIG. 12D) or IL-17 (FIG. 12E) induced by IMQ. Fold change is calculated as individual treated/(average of untreated samples) within each genotype. Mean±SEM; two independent experiments were combined; n=5-6 mice per condition per genotype. *p<0.05 by Student's t-test.

(FIG. 13A) CMKLR1 KO mice were significantly resistant to IMQ-induced increases in back skin thickness (24 h timepoint). Fold change with respect to day 0 measurements are shown. (FIG. 13B) NK cell (CD45+DX5+Ly6G-CD3-CD19-) accumulation in IMQ-treated skin was significantly reduced in CMKLR1 KO mice vs. WT as quantified by flow cytometry (24 h). (FIG. 13C) Subcutaneous administration of CMKLR1 small molecule antagonist α-NETA inhibits IMQ-induced increases in back skin thickness. α-NETA (10 mg/kg) was administered via s.c injection at a ventral skin site opposite from the IMQ treatment site at the time of IMQ administration, 24 h timepoint shown. For A-C, n=3 untreated, n=5 IMQ-treated mice of each genotype, mean±SEM, *p<0.05 by 2-tailed t-test. (FIG. 13D) Oral administration of α-NETA inhibits clinical signs of IMQ-induced psoriasis. α-NETA (30 mg/kg in 10% captisol) or vehicle control was administered by oral gavage daily beginning one day prior to psoriasis induction, 7 days total. α-NETA-treated mice are protected against clinical signs of psoriasis, with visibly reduced skin inflammation (representative images) and significantly reduced skin thickening over time. n=6 mice/group, mean±SEM, *p<0.05 by 2-tailed t-test, posthoc Bonferroni correction for multiple comparisons; t p<0.05 by t-test comparing area under the curve (AUC, integrated disease experienced over time for each mouse).

(FIG. 14A) α-NETA. (FIG. 14B) Ring modification from napthalene to cyclohexane resulted in ~3-fold loss in potency. (FIG. 14C) Ring modification from napthalene to benzene resulted in retained target potency. (FIG. 14C) Changing from α- to β-substituted NETA slightly improved potency.

(FIG. 15A) α-NETA. (FIG. 15B) Ring modification from napthalene to benzene with a para-methoxy substitution significantly improved target potency. (FIG. 15C) Uncharged ortho-methoxy-substituted α-NEDA retained target potency. (FIG. 15A-15C) mean±SEM, n=3-18 independent experiments. (FIG. 15D) Oral administration of α-NETA, (27), and (6) suppress clinical signs of IMQ-induced psoriasis in mice. 0.2 ml each compound (in 10% captisol) or vehicle control was administered by oral gavage beginning one day prior to psoriasis induction. Back skin thickness was measured daily and normalized to day 0. mean±SEM, n=10 mice for vehicle and α-NETA groups pooled from two independent trials; n=3 mice for (27) and (6) from one trial.

DETAILED DESCRIPTION

Figure 1A:
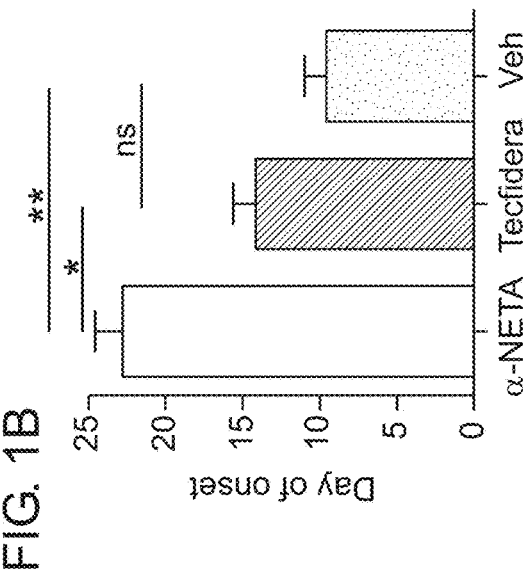
FIG. 1A-1D. Comparing CMKLR1 antagonist α-NETA and FDA-approved Tecfidera (dimethyl fumarate, DMF) in suppressing experimental autoimmune encephalomyelitis (EAE).

As summarized above, the present invention is drawn to compositions and methods for inhibiting the activity of CMKLR1. In some embodiments such methods include treating inflammatory disease in a subject by administering an agent that antagonizes the activity of chemokine-like receptor 1 (CMKLR1) and/or a CMKLR1 ligand (e.g., chemerin or other endogenous CMKLR1 ligands. As such, the methods of the invention find use in treating EAE or MS in a subject. The methods of the invention also find use in treating psoriasis.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Terms

"Activity" of CMKLR1 shall mean any signaling or binding function performed by that protein.

"Comparable cell" shall mean a cell whose type is identical to that of another cell to which it is compared. Examples of comparable cells are cells from the same cell line.

"Inhibiting" the onset of a disorder shall mean either lessening the likelihood of the disorder's onset, or preventing the onset of the disorder entirely. In the preferred embodiment, inhibiting the onset of a disorder means preventing its onset entirely. As used herein, onset may also refer to deterioration in a patient that has chronic/progressive disease, or relapse in a patient that has ongoing relapsing-remitting disease.

The methods of the invention may be specifically applied to individuals that have been diagnosed with an autoimmune disease, e.g. a chronic/progressive or relapsing-remitting disease such as MS or EAE. Treatment is aimed at the treatment or prevention of relapses, which are an exacerbation of a pre-existing condition.

"Inhibiting" the expression of a gene in a cell shall mean either lessening the degree to which the gene is expressed, or preventing such expression entirely.

"Specifically inhibit" the expression of a protein shall mean to inhibit that protein's expression or activity (a) more than the expression or activity of any other protein, or (b) more than the expression or activity of all but 10 or fewer other proteins.

"Subject" or "patient" shall mean any animal, such as a human, non-human primate, mouse, rat, guinea pig or rabbit.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function.

In one embodiment, the term "suitable conditions" as used herein means physiological conditions.

"Treating" a disorder shall mean slowing, stopping or reversing the disorder's progression. In the preferred embodiment, treating a disorder means reversing the disorder's progression, ideally to the point of eliminating the disorder itself. As used herein, ameliorating a disorder and treating a disorder are equivalent.

The term "immune" response is the development of a beneficial humoral (antibody mediated) and/or a cellular (mediated by antigen-specific T cells or their secretion products) response directed against CMKLR1 in a recipient patient. Such a response can be an active response induced by an "immunogen" that is capable of inducing an immunological response against itself on administration to a mammal, optionally in conjunction with an adjuvant.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

As used herein, the term "dose amount" refers to the quantity, e.g., milligrams (mg), of the substance which is administered to the subject. In one embodiment, the dose amount is a fixed dose, e.g., is not dependent on the weight of the subject to which the substance is administered. In another embodiment, the dose amount is not a fixed dose, e.g., is dependent on the weight of the subject to which the substance is administered, or for a topical therapy a dose may be related to the surface area that is treated, e.g. dose/m$^2$ of skin.

Exemplary dose amounts, e.g., fixed dose amounts, for use treating an adult human by the methods of the invention include, about 0.01 mg, about 0.05 mg, about 0.1 mg, about 0.5 mg, about 1 mg, about 5 mg, about 10 mg, about 50 mg, about 100 mg, about 500 mg, or more.

Exemplary dose amounts, e.g., dose amounts for topical use treating an adult human by the methods of the invention include, about 0.01 mg/m$^2$ surface area, about 0.05 mg/m$^2$ surface area, about 0.1 mg/m$^2$ surface area, about 0.5 mg/m$^2$ surface area, about 1 mg/m$^2$ surface area, about 5 mg/m$^2$ surface area, about 10 mg/m² surface area, about 50 mg/m² surface area, about 100 mg/m² surface area, about 500 mg/m² surface area, or more.

Ranges intermediate to the above-recited ranges are also contemplated by the invention. For example, ranges having any one of these values as the upper or lower limits are also intended to be part of the invention, e.g., about 0.01 mg to about 100 mg, about 1 mg to about 10 mg, etc.

As used herein, the term "periodicity" as it relates to the administration of a substance refers to a (regular) recurring cycle of administering the substance to a subject. In one embodiment, the recurring cycle of administration of the substance to the subject achieves a therapeutic objective. The periodicity of administration of the substance may be about once a week, once every other week, about once every three weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks, about once every 21 weeks, about once every 22 weeks, about once every 23 weeks, about once every 24 weeks, about once every 5-10 days, about once every 10-20 days, about once every 10-50 days, about once every 10-100 days, about once every 10-200 days, about once every 25-35 days, about once every 20-50 days, about once every 20-100 days, about once every 20-200 days, about once every 30-50 days, about once every 30-90 days, about once every 30-100 days, about once every 30-200 days, about once every 50-150 days, about once every 50-200 days, about once every 60-180 days, or about once every 80-100 days. Periodicities intermediate to the above-recited times are also contemplated by the invention. Ranges intermediate to the above-recited ranges are also contemplated by the invention. For example, ranges having any one of these values as the upper or lower limits are also intended to be part of the invention, e.g., about 110 days to about 170 days, about 160 days to about 220 days, etc.

The "duration of a periodicity" refers to a time over which the recurring cycle of administration occurs. For example, a duration of the periodicity of administration of a substance may be may be up to about 4 weeks, up to about 8 weeks, up to about 12 weeks, up to about 16 weeks or more, up to about 20 weeks, up to about 24 weeks, up to about 28 week, up to about 32 weeks or more, during which the periodicity of administration is about once every week. For example, a duration of the periodicity may be about 6 weeks during which the periodicity of administration is about once every 4 weeks, e.g., the substance is administered at week zero and at week four.

In one embodiment, the duration of periodicity is for a length of time necessary or required to achieve a therapeutic objective, e.g., treatment, maintenance of treatment, etc. e.g., maintain a PASI 50, PASI 75, PASI 90, PASI 100 score or PGA of 0 or 1 score. Durations of a periodicity intermediate to the above-recited times are also contemplated by the invention.

As used herein, and unless otherwise specified, the terms "treat," "treating" and "treatment" can refer to an action that occurs while a patient is suffering from psoriasis, which reduces the severity of psoriasis, or retards or slows the progression of the psoriasis, or achieving or maintaining a therapeutic objective. An "effective patient response" refers to any increase in the therapeutic benefit to the patient. An "effective patient psoriasis response" can be, for example, a 5%, 10%, 25%, 50%, or 100% decrease in the physical symptoms of psoriasis.

"Treatment of or "treating" psoriasis may mean achieving or maintaining a PGA score of 0/1 or a PASI 50, PASI 75, PASI 90, or PASI 100 response score for a period of time during or following treatment (e.g., for at least 2, 4, 6, 8, 10, 12, 14, 16, 18, 20, 22, 24, 26, 28, 30, 32, 34, 36, 38, 40, 42, 46, 48, 50, 52, 54, 56, 58 or 60 weeks or longer). "Treatment of or "treating" psoriasis may also mean achieving or maintaining a health-related quality of life (HRQOL) outcome. HRQOL outcomes include Dermatology Life Quality Index (DLQI), visual analog scales for Ps-related (VAS-Ps) and psoriatic arthritis-related (VAS-PsA) pain, Short Form 36 Health Survey Mental (MCS) and Physical (PCS) Component Summary scores, and Total Activity Impairment (TAI) scores.

"Treatment of or "treating" psoriasis may also mean achieving or maintaining a minimum clinically important difference (MCID) for any of the HRQOL outcomes provided herein, e.g., any one or combination of DLQI, VAS-Ps, VAS-PsA, MCS, PCS and TAI.

"Treatment of" or "treating" psoriasis may also mean achieving or maintaining a minimum clinically important difference (MCID) response rate for any of the HRQOL outcomes provided herein, e.g., any one or combination of DLQI, VAS-Ps, VAS-PsA, MCS, PCS and TAI. "Treatment of or "treating" psoriasis may also mean achieving or maintaining a clinically meaningful reduction in any of the HRQOL outcomes provided herein, e.g., any one or combination of DLQI, VAS-Ps, VAS-PsA, MCS, PCS and TAI.

"Treatment of" or "treating" psoriasis may also mean achieving or maintaining a Nail Psoriasis Severity Index (NAPSI) score for a period of time during or following treatment (e.g., for at least 2, 4, 6, 8, 10, 12, 14, 16, 18, 20, 22, 24, 26, 28, 30, 32, 34, 36, 38, 40, 42, 46, 48, 50, 52, 54, 56, 58 or 60 weeks or longer).

"Treatment of" or "treating" psoriasis may also mean achieving or maintaining any of the outcomes provided herein in a certain percentage of a population of subjects (e.g., in at least about 10%, 15%, 20%, 25%, 30%, 35%, 40%, 45%, 50%, 55%, 60%, 65%, 70%, 75%, 80%, 85%, 90%, 95%, 99%, or 100% of a population of subjects).

The term "kit" as used herein refers to a packaged product comprising components with which to administer the epithelial ion channel blocker of the invention for treatment of psoriasis. The kit preferably comprises a box or container that holds the components of the kit. The box or container may be affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for use.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl ($(CH_3)_2CH$—), n-butyl ($CH_3CH_2CH_2CH_2$—), isobutyl ($(CH_3)_2CHCH_2$—), sec-butyl ($(CH_3)(CH_3CH_2)CH$—), t-butyl ($(CH_3)_3C$—), n-pentyl ($CH_3CH_2CH_2CH_2CH_2$—), and neopentyl ($(CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Carboxyl," "carboxy" or "carboxylate" refers to —CO$_2$H or salts thereof.

"Carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Halo" or "halogen" refers to fluoro, chloro, bromo, and iodo.

"Hydroxy" or "hydroxyl" refers to the group —OH.

"Nitro" refers to the group —NO$_2$.

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Thiol" refers to the group —SH.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$ (M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$ M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$ M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(N)R$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each Mt is a counter ion with a net single positive charge. Each M+ may independently be, for example, an alkali ion, such as K+, Na+, Li+; an ammonium ion, such as +N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

Representative Embodiments

The present invention provides methods for treating inflammatory disease, including inflammatory demyelinating diseases, such multiple sclerosis; etc. and including psoriasis. These methods comprise administering to the subject having an autoimmune condition, e.g. a demyelinating condition; psoriasis, etc. an effective amount of an inhibitor of CMKLR1.

In some embodiments, a method is provided for inhibiting autoimmune diseases in a subject, the method comprising administering to the subject a prophylactically effective amount of a small molecule that specifically reduces levels of CMKLR1. In other embodiments, a method is provided for inhibiting inflammatory demyelinating disease in a subject, the method comprising administering to the subject a therapeutically effective amount of a small molecule.

In other embodiments, the method comprising administering to said subject an agent that downregulates the expression, or inhibits the activity of, a ligand of CMKLR1, which ligand includes, without limitation, chemerin. In these methods, the CMKLR1-expressing cell can be, without limitation, a macrophage; a dendritic cell; or a microglial cell.

Small Molecule Compounds

This disclosure concerns compounds which are useful as small molecule CMKLR1 antagonists in demyelinating disease and are thus useful for treating a variety of diseases and disorders that are mediated or sustained through the activity of CMKLR1. This disclosure also relates to pharmaceutical compositions comprising these compounds, methods of using these compounds in the treatment of various diseases and disorders, processes for preparing these compounds and intermediates useful in these processes.

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The present embodiments provide a compound of formula (I):

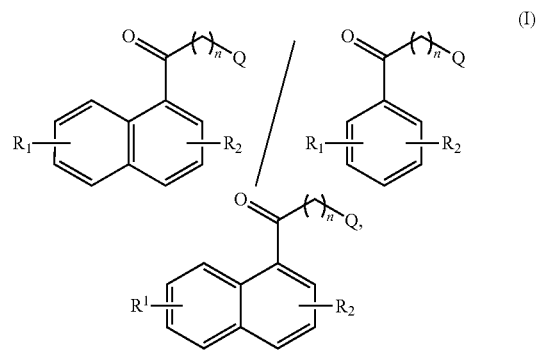

wherein
Q is selected from —NR$^Q_4$+, —NH$_4$+, —NH$_2$, —NHR$^Q$, —NR$^Q_2$, —OH, —SH, and lower alkyl; wherein R$^Q$ is lower alkyl; and wherein; Q is selected from —NR$^Q_4$+ or —NH$_4$+, then X$^-$ is present and is a counterion;

R$^1$ and R$^2$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, and sulfonyl; and n is a number from one to four.

In formula (I), Q is selected from —NR$^Q_4$+, —NH$_4$+, —NH$_2$, —NHR$^Q$, —NR$^Q_2$, —OH, —SH, and lower alkyl; wherein R$^Q$ is lower alkyl; and wherein; Q is selected from —NR$^Q_4$+ or —NH$_4$+, then X$^-$ is present and is a counterion;

In certain embodiments, Q is —NR$^Q_4$+, wherein R$^Q$ is lower alkyl; and wherein X$^-$ is present and is a counterion. In certain embodiments, X$^-$ is selected from fluoride, bromide, chloride, and fluoride.

In certain embodiments, Q is selected from —NR$^Q_4{}^+$ and —NH$_4{}^+$, wherein R$^Q$ is lower alkyl; and wherein X$^-$ is present and is a counterion. In certain embodiments, X$^-$ is selected from fluoride, bromide, chloride, and fluoride.

In certain embodiments, Q is selected from —NH$_2$, —NHR$^Q$, and —NR$^Q_2$; wherein R$^Q$ is lower alkyl. In certain embodiments, Q is —NH$_2$. In certain embodiments, Q is —NHR$^Q$; wherein R$^Q$ is lower alkyl. In certain embodiments, Q is —NR$^Q_2$; wherein R$^Q$ is lower alkyl.

In certain embodiments, Q is selected from —OH, —SH, and lower alkyl. In certain embodiments, Q is —OH. In certain embodiments, Q is —SH. In certain embodiments, Q is lower alkyl.

In formula (I), R$^1$ and R$^2$ are independently selected from hydrogen, alkyl, substituted alkyl, hydroxy, alkoxy, substituted alkoxy, amino, substituted amino, carboxyl, carboxyl ester, cyano, halogen, acyl, aminoacyl, nitro, and sulfonyl.

In certain embodiments, R$^1$ and R$^2$ are hydrogen.

In certain embodiments, R$^1$ and R$^2$ are independently selected from hydrogen, alkyl, and substituted alkyl. In certain embodiments, R$^1$ and R$^2$ are independently selected from hydrogen, hydroxy, alkoxy, and substituted alkoxy. In certain embodiments, R$^1$ and R$^2$ are independently selected from hydrogen, amino, and substituted amino. In certain embodiments, R$^1$ and R$^2$ are independently selected from hydrogen, carboxyl, and carboxyl ester. In certain embodiments, R$^1$ and R$^2$ are independently selected from hydrogen, cyano, halogen, acyl, aminoacyl, nitro, and sulfonyl.

In formula (I), n is a number from one to four. In certain embodiments, n is one. In certain embodiments, n is two. In certain embodiments, n is three. In certain embodiments, n is four.

The present embodiments provide a compound of formula (II):

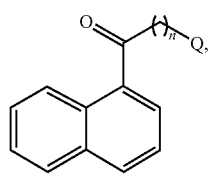

(II)

wherein
Q is selected from —NR$^Q_4{}^+$, —NH$_4{}^+$, —NH$_2$, —NHR$^Q$, —NR$^Q_2$, —OH, —SH, and lower alkyl; wherein R$^Q$ is lower alkyl; and wherein; Q is selected from —NR$^Q_4{}^+$ or —NH$_4{}^+$, then X$^-$ is present and is a counterion; and n is a number from one to four.

In formula (II), Q is selected from —NR$^Q_4{}^+$, —NH$_4{}^+$, —NH$_2$, —NHR$^Q$, —NR$^Q_2$, —OH, —SH, and lower alkyl; wherein R$^Q$ is lower alkyl; and wherein; Q is selected from —NR$^Q_4{}^+$ or —NH$_4{}^+$, then X$^-$ is present and is a counterion;

In certain embodiments, Q is —NR$^Q_4{}^+$, wherein R$^Q$ is lower alkyl; and wherein X$^-$ is present and is a counterion. In certain embodiments, X$^-$ is selected from fluoride, bromide, chloride, and fluoride.

In certain embodiments, Q is selected from —NR$^Q_4{}^+$ and —NH$_4{}^+$, wherein R$^Q$ is lower alkyl; and wherein X$^-$ is present and is a counterion. In certain embodiments, X$^-$ is selected from fluoride, bromide, chloride, and fluoride.

In certain embodiments, Q is selected from —NH$_2$, —NHR$^Q$, and —NR$^Q_2$; wherein R$^Q$ is lower alkyl. In certain embodiments, Q is —NH$_2$. In certain embodiments, Q is —NHR$^Q$; wherein R$^Q$ is lower alkyl. In certain embodiments, Q is —NR$^Q_2$; wherein R$^Q$ is lower alkyl.

In certain embodiments, Q is selected from —OH, —SH, and lower alkyl. In certain embodiments, Q is —OH. In certain embodiments, Q is —SH. In certain embodiments, Q is lower alkyl.

In formula (II), n is a number from one to four. In certain embodiments, n is one. In certain embodiments, n is two. In certain embodiments, n is three. In certain embodiments, n is four.

The present embodiments provide a compound of formula (III):

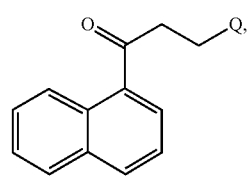

(III)

wherein
Q is selected from —NR$^Q_4{}^+$, —NH$_4{}^+$, —NH$_2$, —NHR$^Q$, —NR$^Q_2$, —OH, —SH, and lower alkyl; wherein R$^Q$ is lower alkyl; and wherein; Q is selected from —NR$^Q_4{}^+$ or —NH$_4{}^+$, then X$^-$ is present and is a counterion.

In formula (III), Q is selected from —NR$^Q_4{}^+$, —NH$_4{}^+$, —NH$_2$, —NHR$^Q$, —NR$^Q_2$, —OH, —SH, and lower alkyl; wherein R$^Q$ is lower alkyl; and wherein; Q is selected from —NR$^Q_4{}^+$ or —NH$_4{}^+$, then X$^-$ is present and is a counterion;

In certain embodiments, Q is —NR$^Q_4{}^+$, wherein R$^Q$ is lower alkyl; and wherein X$^-$ is present and is a counterion. In certain embodiments, X$^-$ is selected from fluoride, bromide, chloride, and fluoride.

In certain embodiments, Q is selected from —NR$^Q_4{}^+$ and —NH$_4{}^+$, wherein R$^Q$ is lower alkyl; and wherein X$^-$ is present and is a counterion. In certain embodiments, X$^-$ is selected from fluoride, bromide, chloride, and fluoride.

In certain embodiments, Q is selected from —NH$_2$, —NHR$^Q$, and —NR$^Q_2$; wherein R$^Q$ is lower alkyl. In certain embodiments, Q is —NH$_2$. In certain embodiments, Q is —NHR$^Q$; wherein R$^Q$ is lower alkyl. In certain embodiments, Q is —NR$^Q_2$; wherein R$^Q$ is lower alkyl.

In certain embodiments, Q is selected from —OH, —SH, and lower alkyl. In certain embodiments, Q is —OH. In certain embodiments, Q is —SH. In certain embodiments, Q is lower alkyl.

A particular compound of interest is shown as Formula IV below:

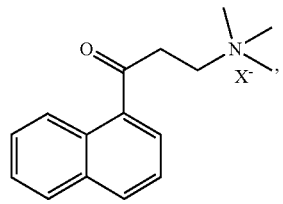

(IV)

wherein
X$^-$ is selected from iodide, bromide, chloride, and fluoride.

A particular compound of interest is 2-(alpha-naphthoyl) ethyltrimethyl ammonium iodide, shown below:

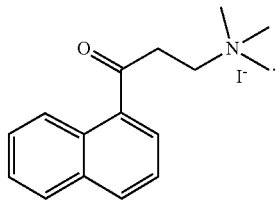

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Exemplary synthetic methods for the compounds described herein are described below.

In certain embodiments, analogs of 2-(alpha-naphthoyl) ethyltrimethyl ammonium iodide, shown below:

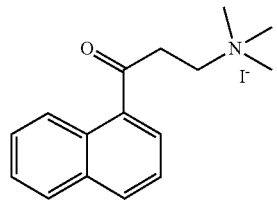

are used. In certain embodiments, counterion exchanges can be performed with ion exchange chromatography. Modification of the naphthyl ring with substituents can be performed with standard chemical reactions known to one skilled in the art. Suitable reactions for modification of the naphthyl ring include electrophilic aromatic substitution. For example, the naphthyl ring can react with chlorine to form a chloro-substituted naphthyl ring. Further reaction of chloro-substituted naphthyl ring can occur with appropriate substituents. The naphthyl ring can also be alkylated using Friedel-Crafts reactions.

In certain embodiments, a Friedel-Crafts acylation can be performed on naphthylene. Further reaction of carbonyl group of the acylated naphthyl ring can be performed to obtain compounds of Formula (I)-(III).

Administration

In a certain embodiment, the present invention is drawn to methods for treating psoriasis or demyelinating inflammatory disease in a subject by administering an α-NETA analog as described herein.

In a certain embodiment, relapse of an autoimmune disease in a subject is inhibited or prevented by administering to the subject a prophylactically or therapeutically effective amount of an agent of the invention.

Determining a therapeutically or prophylactically effective amount of the analog compositions can be done based on animal data using routine computational methods.

In this invention, administering the instant compositions can be effected or performed using any of the various methods and delivery systems known to those skilled in the art. The administering can be performed, for example, intravenously, orally, via implant, transmucosally, transdermally, intramuscularly, intrathecally, and subcutaneously. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone. Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and Jun. 2, 2005 antioxidants (e.g., parabens, vitamins E and C, and ascorbic acid), anti-caking agents, coating agents, and chelating agents (e.g., EDTA), captisol, etc.

Formulations. The present invention provides pharmaceutically acceptable compositions which comprise a therapeutically-effective amount of at least one α-NETA analog, optionally combined with one or more additional agents for treatment of psoriasis or multiple sclerosis, formulated together with one or more pharmaceutically acceptable excipients. The active ingredients and excipient(s) may be formulated into compositions and dosage forms according to methods known in the art. As described in detail below, the pharmaceutical compositions of the present invention may be specially formulated for administration in solid or liquid form, including those adapted for the following: oral administration, for example, tablets, capsules, powders, granules, pastes for application to the tongue, aqueous or non-aqueous solutions or suspensions, drenches, or syrups; parenteral administration, for example, by subcutaneous, intramuscular or intravenous injection as, for example, a sterile solution or suspension. In other embodiments the formulation is provided for topical application, for example, as a lotion, cream, ointment, spray, patch, microneedle array, etc. applied to the skin.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: ethanol, sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19.sup.th Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose, hydroxypropyl methyl cellulose, liquid glucose, magnesium aluminum silicate, maltodextrin, methylcellulose, polymethacrylates, povidone, pregelatinized starch, sodium alginate and starch. The dissolution rate of a compacted solid pharmaceutical composition in the subject's stomach may be increased by the addition of a disintegrant to the composition. Disintegrants include alginic acid, carboxymethylcellulose calcium, carboxymethylcellulose sodium, colloidal silicon dioxide, croscarmellose sodium, crospovidone, guar gum, magnesium aluminum silicate, methyl cellulose, microcrystalline cellulose, polacrilin potassium, powdered cellulose, pregelatinized starch, sodium alginate, sodium starch glycolate and starch.

In liquid pharmaceutical compositions of the present invention, the agent and any other solid excipients are dissolved or suspended in a liquid carrier such as water, water-for-injection, vegetable oil, alcohol, polyethylene glycol, propylene glycol or glycerin. Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol. Liquid pharmaceutical compositions of the present invention may also contain a viscosity enhancing agent to improve the mouth-feel of the product and/or coat the lining of the gastrointestinal tract. Sweetening agents such as sorbitol, saccharin, sodium saccharin, sucrose, aspartame, fructose, mannitol and invert sugar may be added to improve the taste. Flavoring agents and flavor enhancers may make the dosage form more palatable to the patient. Preservatives and chelating agents such as alcohol, sodium benzoate, butylated hydroxy toluene, butylated hydroxyanisole and ethylenediamine tetraacetic acid may be added at levels safe for ingestion to improve storage stability. Selection of excipients and the amounts used may be readily determined by the formulation scientist based upon experience and consideration of standard procedures and reference works in the field.

In several embodiments of the invention the α-NETA analog is formulated for topical application to the skin various specific formulations are provided, including lotions, gels, liquids, patches, intralesional injection, and the like. A typical dose for a topical formulation in lotion or liquid form is from about 1 µl to about 100 µl to about 1 ml, to about 10 ml, applied in a lotion, cream, gel, etc. to the affected skin.

In general, the subject formulations will typically contain at least about 1 µg/ml active agent, at least about 10 µg/ml, at least about 50 µg/ml, at least about 100 µg/ml, at least about 500 µg/ml, and not more than about 100 mg/ml. In some embodiments the formulation comprises at least about 0.1 mM, at least about 0.05, at least about 1 mM, at least about 5 mM, at least about 10 mM, at least about 50 mM. The active agents of the present invention are formulated at an effective concentration within the subject formulations, meaning at a concentration that provides the intended benefit when applied topically.

The dose of active agent is as described above with respect to the surface area to be treated, where the dose may be up to about 0.01 mg/kg body weight, up to about 0.05 mg/kg body weight, up to about 0.1 mg/kg body weight, up to about 0.5 mg/kg body weight, up to about 1 mg/kg body weight, up to about 2 mg/kg body weight, up to about 5 mg/kg body weight, up to about 10 mg/kg body weight.

Administration may be every 6 hours, every 12 hours, every 24 hours, every 48 hours, every 3 days, every 4 days, every 5 days, weekly, biweekly, monthly, etc. In various of these embodiments, the therapeutically effective dose is administered on consecutive days for at least a week, at least a month, at least a year, or on as needed basis for the rest of the patient's life. The therapeutically effective dose, e.g. of Benzamil, or pharmaceutically acceptable salt thereof, can be about 10-500 mg/day, about 50-400 mg/day, about 100-200 mg/day, or about 120-180 mg/day. Benzamil or pharmaceutically acceptable salt thereof, can be administered to a subject at about 1-110 mg daily, 1-100 mg twice a day, 1-100 mg. every other day, as needed.

Examples are provided herein of dosages useful for treatment of an animal model. As is known in the art, in order to convert dosage from, for example, a mouse to a human, the animal dose should not be extrapolated to a human equivalent dose (HED) by a simple conversion based on body weight. The more appropriate conversion of drug doses from animal studies to human studies, uses the body surface area (BSA) normalization method. BSA correlates well across several mammalian species with several parameters of biology, including oxygen utilization, caloric expenditure, basal metabolism, blood volume, circulating plasma proteins, and renal function. See, for example, Reagan-Shaw et al. (2008) *The FASEB Journal* 22(3), 659-661, herein specifically incorporated by reference. The appropriate dose for a human may be roughly $\frac{1}{10}^{th}$ to $\frac{1}{20}^{th}$ of the dose for a mouse. See also, FDA guidance for Estimating the Maximum Safe Starting Dose in Initial Clinical Trials for Therapeutics in Adult Healthy Volunteers.

In some embodiments, the topical formulation comprises skin penetration enhancers. Such enhancers reversibly decrease skin barrier resistance, and include without limitation, sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes.

Topical formulations include lotions, gels, creams, etc. Such formulations may include a pharmaceutically acceptable vehicle to act as a dilutant, dispersant or carrier for the active agent(s), so as to facilitate distribution when the composition is applied to the skin. Vehicles other than or in addition to water can include liquid or solid emollients, solvents, humectants, thickeners and powders. The vehicle will usually form from 5% to 99.9%, preferably from 25% to 80% by weight of the composition, and can, in the absence of other cosmetic adjuncts, form the balance of the composition. The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from 0.3% to 30% by weight, and preferably from 0.5% to 20% by weight, relative to the total weight of the composition. When the lotions are formulated as an oily solution or gel, the fatty phase may constitute more than 90% of the total weight of the composition.

Formulations may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase, into the aqueous phase.

Exemplary oils which may be used according to this invention include mineral oils (liquid petrolatum) and solid oils, e.g. petrolatum, plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats. Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol. Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons. Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids. Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients for lotions are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality. Powders may be incorporated into a lotion. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

An alternative formulation for topical delivery is an array of microneedles. Microneedles (MN), as used herein, refers to an array comprising a plurality of micro-projections, generally ranging from about 25 to about 2000 µm in length, which are attached to a base support. An array may comprise $10^2$, $10^3$, $10^4$, $10^5$ or more microneedles, and may range in area from about 0.1 cm² to about 100 cm². Application of MN arrays to biological membranes creates transport pathways of micron dimensions, which readily permit transport of macromolecules such as large polypeptides. In some embodiments of the invention, the microneedle array is formulated as a transdermal drug delivery patch. MN arrays can alternatively be integrated within an applicator device which, upon activation, can deliver the MN array into the skin surface, or the MN arrays can be applied to the skin and the device then activated to push the MN through the SC.

Various materials have been used for microneedles. For example, biodegradable materials into which the therapeutic agent, e.g. Benzamil, can be incorporated are of interest. Such materials include various biodegradable or biocompatible polymers or cross-linked monomers, as known in the art. The dose of agent to be delivered will vary, and may range from at least about 1 ng/microneedle array, at least about 10 ng, at least about 0.1 µg, at least about 1 µg, at least about 10 µg, at least 0.1 mg, at least 1 mg, or more in a single array. MNs may be fabricated with a wide range of designs (different sizes and shapes) and different types (solid, hollow, sharp, or flat), and may be in-plane and/or out-of-plane.

Polymeric MNs can provide biocompatibility, biodegradability, strength, toughness, and optical clarity. To accurately produce the micro-scale dimensions of polymer MNs, a variety of mould-based techniques, such as casting, hot embossing, injection molding, and investment molding may be used, e.g. beveled-tip, chisel-tip, and tapered-cone polydimethylsiloxane (PDMS) molds. Polymeric materials of interest for fabrication include without limitation; poly (methylmetha-acrylate) (PMMA), poly-L-lactic acid (PLA), poly-glycolic acid (PGA), and poly-lactic-co-glycolic acid (PLGA), cyclic-olefin copolymer, poly (vinyl pyrrolidone), and sodium carboxymethyl cellulose. Sugars have also been used to fabricate the MNs, such as galactose, maltose, aliginate, chitosan, and dextrin. Materials may be cross-linked through ion exchange, photo-polymerization, and the like.

In other embodiments, a topical formulation is provided as a transdermal patch. Medical dressings suitable for formulation in a transdermal patch can be any material that is biologically acceptable and suitable for placing over the skin. In exemplary embodiments, the support may be a woven or non-woven fabric of synthetic or non-synthetic fibers, or any combination thereof. The dressing may also comprise a support, such as a polymer foam, a natural or man-made sponge, a gel or a membrane that may absorb or have disposed thereon, a therapeutic composition. A gel suitable for use as a support is sodium carboxymethylcellulose 7H 4F, i.e. ethylcellulose.

For example, hydrocolloids (eg, RepliCare, DuoDERM, Restore, Tegasorb), which are combinations of gelatin, pectin, and carboxymethylcellulose in the form of wafers, powders, and pastes; some have adhesive backings and others are typically covered with transparent films to ensure adherence. Alginates (polysaccharide seaweed derivatives containing alginic acid), which come as pads, ropes, and ribbons (AlgiSite, Sorbsan, Curasorb), are indicated for extensive exudate and for control of bleeding after surgical debridement. Foam dressings (Allevyn, LYOfoam, Hydrasorb, Mepilex, Curafoam, Contreet) are useful as they can handle a variety of levels of exudate and provide a moist environment for healing. Those with adhesive backings stay in place longer and need less frequent changing.

In some embodiments, a transdermal patch comprises permeation enhancer, e.g. transcutol, (diethylene glycol monoethyl ether), propylene glycol, dimethylsulfoxide (DMSO), menthol, 1-dodecylazepan-2-one (Azone), 2-nonyl-1,3-dioxolane (SEPA 009), sorbitan monolaurate (Span20), and dodecyl-2-dimethylaminopropanoate (DDAIP), which may be provided at a weight/weight concentration of from about 0.1% to about 10%, usually from about 2.5% to about 7.5%, more usually about 5%.

Transdermal patches may further comprise additives to prevent crystallization. Such additives include, without limitation, one or more additives selected from octyldodecanol at a concentration of from about 1.5 to about 4% w/w of polymer; dextrin derivatives at a concentration of from about 2 to about 5% w/w of polymer; polyethylene glycol (PEG) at a concentration of from about 2 to about 5% w/w of polymer; polypropylene glycol (PPG) at a concentration of from about 2 to about 5% w/w of polymer; mannitol at a concentration of from about 2 to about 4% w/w of polymer; Poloxamer 407, 188, 401 and 402 at a concentration of from about 5 to about 10% w/w of polymer; and Poloxamines 904 and 908 at a concentration of from about 2 to about 6% w/w of polymer.

Polyvinylpyrrolidine (PVP) may also be included in a transdermal patch formulation, for example at a concentration of from about 5 wt % to about 25 weight %, about 7 wt % to about 20 wt %, about 8 wt % to about 18 wt %, about 10 wt % to about 16 wt %, about 10 wt %, about 12 wt %, about 14 wt %, about 16 wt %.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

Therapeutic formulations for treatment of psoriasis or multiple sclerosis with an α-NETA analog can be used alone or in combination with an additional agent, e.g., a therapeutic agent, said additional agent being selected by the skilled artisan for its intended purpose. For example, the additional agent can be a therapeutic agent art-recognized as being useful to treat autoimmune disease. The agents set forth below are illustrative for purposes and not intended to be limited. The combinations which are part of this invention can be an α-NETA analog and at least one additional agent selected from the lists below. The combination can also include more than one additional agent, e.g., two or three additional agents if the combination is such that the formed composition can perform its intended function.

Additional therapeutic agents include, without limitation, methotrexate, 6-MP, azathioprine sulphasalazine, mesalazine, olsalazine chloroquinine/hydroxychloroquine, pencillamine, aurothiomalate (intramuscular and oral), azathioprine, colchicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, etc., phosphodiesterase inhibitors, adensosine agonists, antithrombotic agents, complement inhibitors, adrenergic agents, agents which interfere with signaling by proinflammatory cytokines such as TNFα. or IL-1 (e.g. IRAK, NIK, IKK, p38 or MAP kinase inhibitors), IL-1.beta. converting enzyme inhibitors (e.g., Vx740), anti-P7s, p-selectin glycoprotein ligand (PSGL), TNFα converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG and p55TNFRIgG, sIL-1RI, sIL-1RII, sIL-6R, soluble IL-13 receptor (sIL-13)) and anti-inflammatory cytokines (e.g. IL-4, IL-10, IL-11, IL-13 and TGFβ). In some embodiments the dose of the additional therapeutic agent when co-formulated with an ENAC blocker is lower than the conventional dose. In some embodiments, Benzamil is co-formulated with a glucocorticoid.

Treatment with an α-NETA analog for psoriasis can also be combined with PUVA therapy. PUVA is a combination of psoralen (P) and long-wave ultraviolet radiation (UVA) that is used to treat many different skin conditions. In still another embodiment, the compositions of the invention are administered with excimer laser treatment for treating psoriasis.

Treatment for psoriasis often includes a topical corticosteroids, vitamin D analogs, and topical or oral retinoids, or combinations thereof. In one embodiment, an ENAC blocker is administered in combination with or the presence of one of these common treatments.

The composition can be packaged in any suitable container to suit its viscosity and intended use. The invention accordingly also provides a closed container containing a therapeutically acceptable composition as herein defined.

The pharmaceutical compositions of the invention may include a "therapeutically effective amount" or a "prophylactically effective amount". A "therapeutically effective amount" refers to an amount effective, at dosages and for periods of time necessary, to achieve the desired therapeutic result. A therapeutically effective amount may vary according to factors such as the disease state, age, sex, and weight of the individual, and the ability to elicit a desired response in the individual. A therapeutically effective amount is also one in which any toxic or detrimental effects are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In one embodiment, the dose is administered to the subject upon a flare of disease. In another embodiment, the dose is administered to the subject prior to a flare of disease.

A flare of psoriasis may be monitored by determining a subject's Psoriasis Area and Severity Index (PAST), e.g., PASI 100 response, PASI 90 response, PASI 75 response, PASI 50 response, the PASI response of a single body region, two body regions, three body regions, or four body regions, e.g., trunk, lower extremities, upper extremities, or head and neck. Alternatively, the flare of psoriasis may be monitored by determining a subject's Physician's Global Assessment (PGA) rating.

Conditions for Analysis and Therapy

The compositions and methods of the invention find use in combination with a variety of demyelinating autoimmune conditions, including chronic/progressive and relapsing demyelinating autoimmune diseases and psoriasis. Generally patients for the methods of the present invention are diagnosed as having an autoimmune condition, e.g. psoriasis, a relapsing-remitting autoimmune condition, prior to treatment. The inhibition of CMKLR1 decreases the severity or incidence of relapses in such patients.

Multiple sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

Clinical data alone may be sufficient for a diagnosis of MS. If an individual has suffered two separate episodes of neurologic symptoms characteristic of MS, and the individual also has consistent abnormalities on physical examination, a diagnosis of MS can be made with no further testing. Magnetic resonance imaging (MRI) of the brain and spine is often used during the diagnostic process. MRI shows areas of demyelination (lesions) as bright spots on the image. A substance, called Gadolinium, can be injected into the spinal column to highlight active plaques and, by elimination, demonstrate the existence of historical lesions not associated with clinical symptoms. This can provide the evidence of chronic disease needed for a definitive diagnosis of MS. Testing of cerebrospinal fluid (CSF) can provide evidence of chronic inflammation of the central nervous system. The CSF is tested for oligoclonal bands, which are immunoglobulins found in 85% to 95% of people with definite MS. Combined with MRI and clinical data, the presence of oligoclonal bands can help make a definite diagnosis of MS. Lumbar puncture is the procedure used to collect a sample of CSF.

The brain of a person with MS often responds less actively to stimulation of the optic nerve and sensory nerves. These brain responses can be examined using visual evoked potentials (VEPs) and somatosensory evoked potentials (SEPs). Decreased activity on either test can reveal demyelination which may be otherwise asymptomatic. Along with other data, these exams can help find the widespread nerve involvement required for a definite diagnosis of MS.

In 1996 the United States National Multiple Sclerosis Society standardized the following four subtype definitions (see Lublin and Reingold (1996) Neurology 46(4):907-11, herein specifically incorporated by reference) as relapsing-remitting; secondary progressive; primary progressive; progressive relapsing. The methods of the invention find particular use in the treatment of ongoing disease, and particularly in treating relapsing forms.

Relapsing-remitting describes the initial course of 85% to 90% of individuals with MS. This subtype is characterized by unpredictable attacks (relapses) followed by periods of months to years of relative quiet (remission) with no new signs of disease activity. Deficits suffered during the attacks may either resolve or may be permanent. When deficits always resolve between attacks, this is referred to as "benign" MS.

Secondary progressive describes around 80% of those with initial relapsing-remitting MS, who then begin to have neurologic decline between their acute attacks without any definite periods of remission. This decline may include new neurologic symptoms, worsening cognitive function, or other deficits. Secondary progressive is the most common type of MS and causes the greatest amount of disability.

Primary progressive describes the approximately 10% of individuals who never have remission after their initial MS symptoms. Decline occurs continuously without clear attacks. The primary progressive subtype tends to affect people who are older at disease onset.

Progressive relapsing describes those individuals who, from the onset of their MS, have a steady neurologic decline but also suffer superimposed attacks; and is the least common of all subtypes.

Peripheral neuropathies may also have a relapsing remitting course, and may include Miller Fisher syndrome; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy; IgM monoclonal gammopathies with its subtypes Waldenstrom's macroglobulinemia, myelin-associated glycoprotein-associated gammopathy, polyneuropathy, organomegaly, endocrinopathy, M-protein, skin changes syndrome, mixed cryoglobulinemia, gait ataxia, late-onset polyneuropathy syndrome, and MGUS.

Chronic Plaque Psoriasis.

Chronic plaque psoriasis (also referred to as psoriasis vulgaris) is the most common form of psoriasis. Chronic plaque psoriasis is characterized by raised reddened patches of skin, ranging from coin-sized to much larger. In chronic plaque psoriasis, the plaques may be single or multiple, they may vary in size from a few millimeters to several centimeters. The plaques are usually red with a scaly surface, and reflect light when gently scratched, creating a "silvery" effect. Lesions (which are often symmetrical) from chronic plaque psoriasis occur all over body, but with predilection for extensor surfaces, including the knees, elbows, lumbosacral regions, scalp, and nails. Occasionally chronic plaque psoriasis can occur on the penis, vulva and flexures, but scaling is usually absent. Diagnosis of patients with chronic plaque psoriasis is usually based on the clinical features described above. In particular, the distribution, color and typical silvery scaling of the lesion in chronic plaque psoriasis are characteristic of chronic plaque psoriasis.

Guttate Psoriasis.

Guttate psoriasis refers to a form of psoriasis with characteristic water drop shaped scaly plaques. Flares of guttate psoriasis generally follow an infection, most notably a streptococcal throat infection. Diagnosis of guttate psoriasis is usually based on the appearance of the skin, and the fact that there is often a history of recent sore throat.

Inverse Psoriasis.

Inverse psoriasis is a form of psoriasis in which the patient has smooth, usually moist areas of skin that are red and inflamed, which is unlike the scaling associated with plaque psoriasis. Inverse psoriasis is also referred to as intertiginous psoriasis or flexural psoriasis. Inverse psoriasis occurs mostly in the armpits, groin, under the breasts and in other skin folds around the genitals and buttocks, and, as a result of the locations of presentation, rubbing and sweating can irritate the affected areas.

Pustular Psoriasis.

Pustular psoriasis, also referred to as palmar plantar psoriasis, is a form of psoriasis that causes pus-filled blisters that vary in size and location, but often occur on the hands and feet. The blisters may be localized, or spread over large areas of the body. Pustular psoriasis can be both tender and painful, can cause fevers.

Erythrodermic Psoriasis.

Erythrodermic psoriasis is a particularly inflammatory form of psoriasis that often affects most of the body surface. It may occur in association with von Zumbusch pustular psoriasis. It is a rare type of psoriasis, occurring once or more during the lifetime of 3 percent of people who have psoriasis. It generally appears on people who have unstable plaque psoriasis. Widespread, fiery redness and exfoliation of the skin characterize this form. Severe itching and pain often accompanies it. Erythrodermic psoriasis causes protein and fluid loss that can lead to severe illness. Edema (swelling from fluid retention), especially around the ankles, may develop, along with infection. Erythrodermic psoriasis also can bring on pneumonia and congestive heart failure. People with severe cases often require hospitalization. Erythrodermic psoriasis can occur abruptly at the first signs of psoriasis or it can come on gradually in people with plaque psoriasis. Combination treatments are frequently required, for example topical products and one or two systemic medications.

An inhibitory agent may inhibit the activity of CMKLR1 by a variety of different mechanisms. In certain embodiments, the inhibitory agent is one that binds to the protein CMKLR1 and, in doing so, inhibits its activity. In other embodiments, the inhibitory agent prevents expression of CMKLR1.

An inhibitory agent may act on CMKLR1 mRNA to inhibit the activity of the target CMKLR1 by reducing the amount of CMKLR1 RNA present in the targeted cells, where the target cell may be present in vitro or in vivo. By "reducing the amount of" is meant that the level or quantity of the target CMKLR1 in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods. An effective dose of inhibitor can be the dose that provides for such a reduction in CMKLR1 activity.

EXPERIMENTAL

Example 1

Novel CMKLR1 Inhibitors for Application in Demyelinating Disease

Small molecules that disrupt leukocyte trafficking have proven effective in treating patients with multiple sclerosis (MS). We previously reported that chemerin receptor chemokine-like receptor 1 (CMKLR1) is required for maximal clinical and histological experimental autoimmune encephalomyelitis (EAE); and identified CMKLR1 small molecule antagonist 2-(α-naphthoyl) ethyltrimethylammonium iodide (α-NETA) that significantly suppressed disease onset in vivo. Here we directly compared α-NETA versus FDA-approved MS drug Tecfidera for clinical efficacy in EAE; characterized key safety/toxicity parameters for α-NETA; identified structure-activity relationships among α-NETA domains and CMKLR1 inhibition; and evaluated improved α-NETA analogs for in vivo efficacy. α-NETA proved safe and superior to Tecfidera in suppressing clinical EAE. In addition, we discovered structurally differentiated α-NETA analogs (primarily ortho- or para-methoxy substitutions) with significantly improved target potency in vitro and improved efficacy in vivo. These findings demonstrate that α-NETA-based CMKLR1 inhibitors can be safe and effective in treating demyelinating diseases and potentially other autoimmune disorders.

Figure 1B:
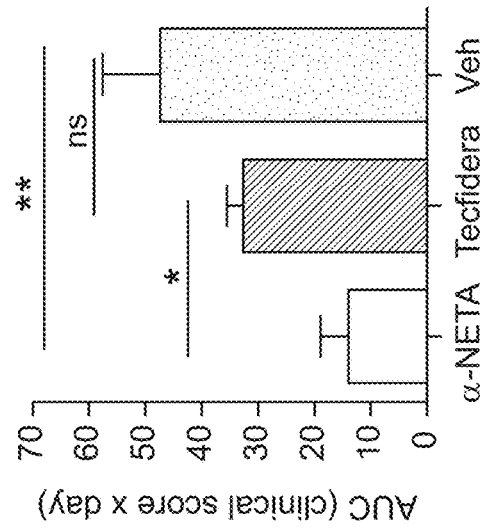
Figure 1C:
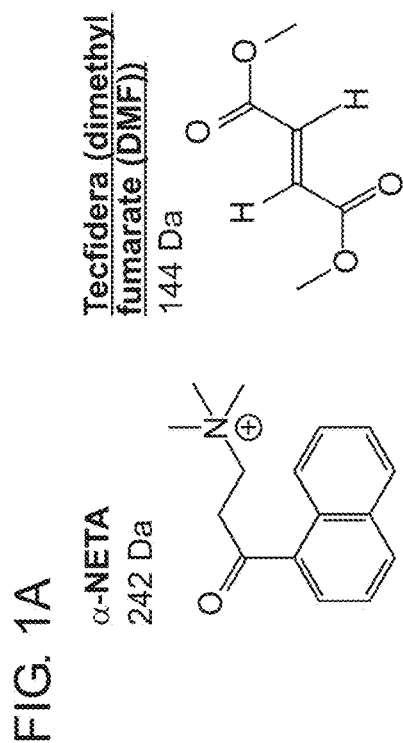
Figure 1D:
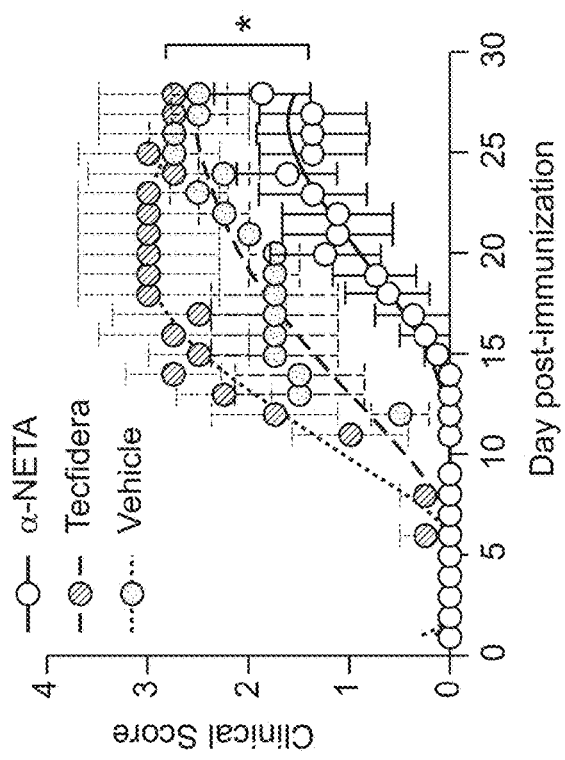

Results

α-NETA is Superior to Tecfidera in Suppressing Clinical EAE in vivo. We compared α-NETA vs. FDA-approved Tecfidera (FIG. 1A) for efficacy in suppressing clinical signs of EAE induced by immunization with myelin oligodendrocyte glycoprotein peptide 35-55. When administered daily at the same dose (10 mg/kg) in the same vehicle (10% captisol in water), α-NETA significantly delayed disease onset compared with either Tecfidera or vehicle control (day of EAE onset for α-NETA: 21±2; Tecfidera: day 14±2; vehicle: day 10±2, mean±SEM, *p<0.05 by ANOVA; FIG. 1B). The severity of clinical EAE was also significantly suppressed by α-NETA compared with Tecfidera or vehicle control (FIG. 1C). In addition, we previously showed that α-NETA treatment significantly reduced mononuclear cell infiltrates within the CNS. We also quantified the total disease experienced by animals in the three treatment groups by area under the curve analysis (FIG. 1D). Thus, by these methods of analyses of clinical EAE, α-NETA-treated animals experienced significantly less severe disease than Tecfidera or vehicle-treated controls (FIG. 1).

Figure 2A:
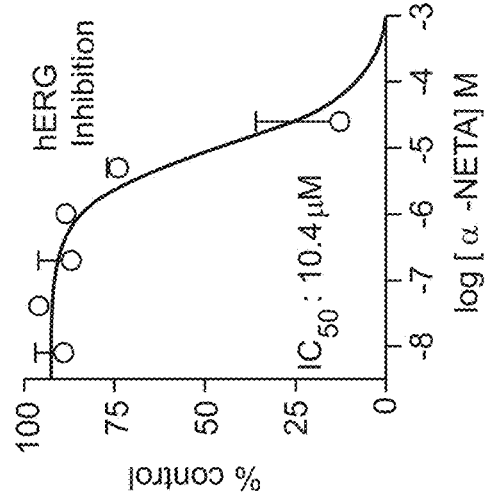
FIG. 2A-2C. In vitro safety assessment.

In vitro Safety Analysis of α-NETA. We assessed potential off-target activity of α-NETA in inhibiting or inducing the activity of cytochrome P450 (Cyp) drug metabolizing enzymes. Effects on the Cyp enzymes are important in avoiding potentially serious drug-drug interactions that can derail drug development efforts. In human liver microsomal Cyp activity assays, α-NETA had little inhibitory activity against Cyp1A2, 2C9, 2C19, 2D6, and 3A4, which are the main drug detoxifying enzymes in the Cyp family (Table 1). α-NETA had some inhibitory activity against Cyp2C8 (IC50: 1.5 uM) and was a relatively potent inhibitor of Cyp2B6 (IC50: 0.12 uM). No time-dependent (mechanism-based) Cyp inhibition was detected. To assess possible induction of Cyp enzymes, we used a reporter cell line to assess activation of nuclear receptor PXR, which is commonly induced by Cyp enzymes. α-NETA did not induce substantial PXR activity at concentrations up to 50 uM (FIG. 2A).

Figure 2B:
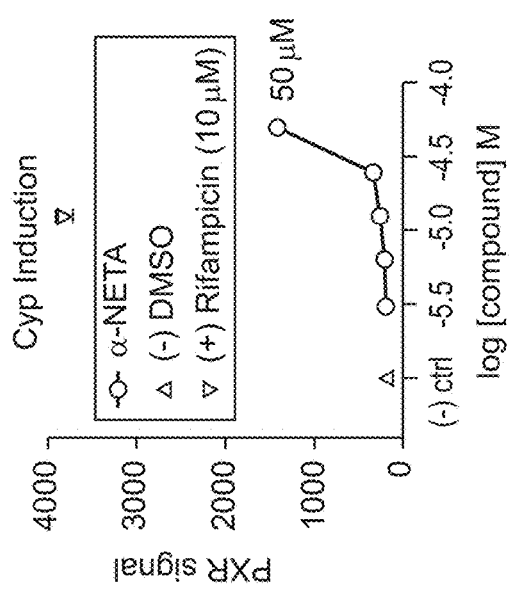
Figure 2C:
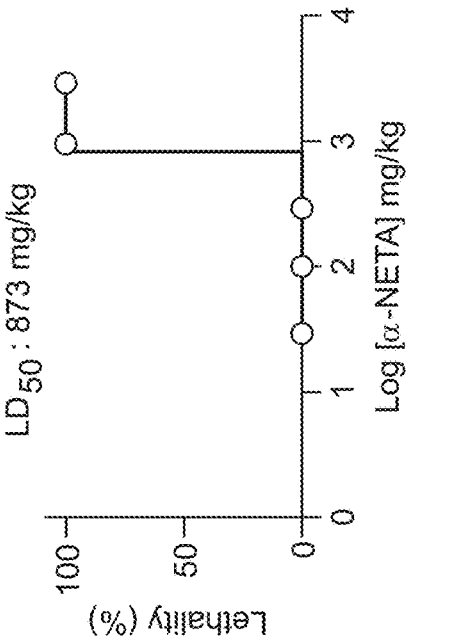

Cardiotoxicity by off-target interference with human Ether-a-go-go Related Gene (hERG) potassium channels is a major safety concern in drug development. In preliminary studies, we assessed potential off-target hERG inhibition by α-NETA using a gold-standard patch-clamp single cell depolarization assay. α-NETA had little inhibitory activity against hERG ($IC_{50}$>10 uM) (FIG. 2B). Genotoxicity by off-target mutagenic effects represents an important safety concern. In preliminary studies, we assessed potential off-target genotoxicity by α-NETA using the Ames test. α-NETA did not induce mutagenesis (monitored by reversion of an obligate histidine mutation) at concentrations up to at least 10 uM (FIG. 2C).

Figure 3:
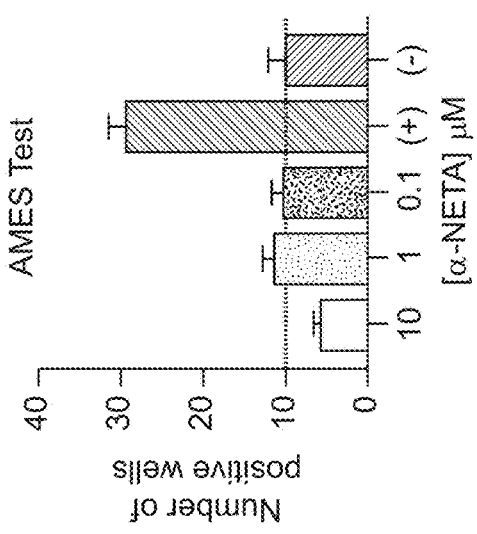
FIG. 3. Acute single dose toxicity (LD50) of α-NETA. WT C57BL6 mice were treated with the following doses of α-NETA: 3000, 1000, 300, 100, 30, 0 mg/kg by oral gavage (200 ul/dose in 10% captisol). Lethal effects were observed within hours for the two highest doses. The remaining mice were monitored for 14 days. Graph depicts lethality at each dose, n=3 per mice/dose.
Figure 4A:
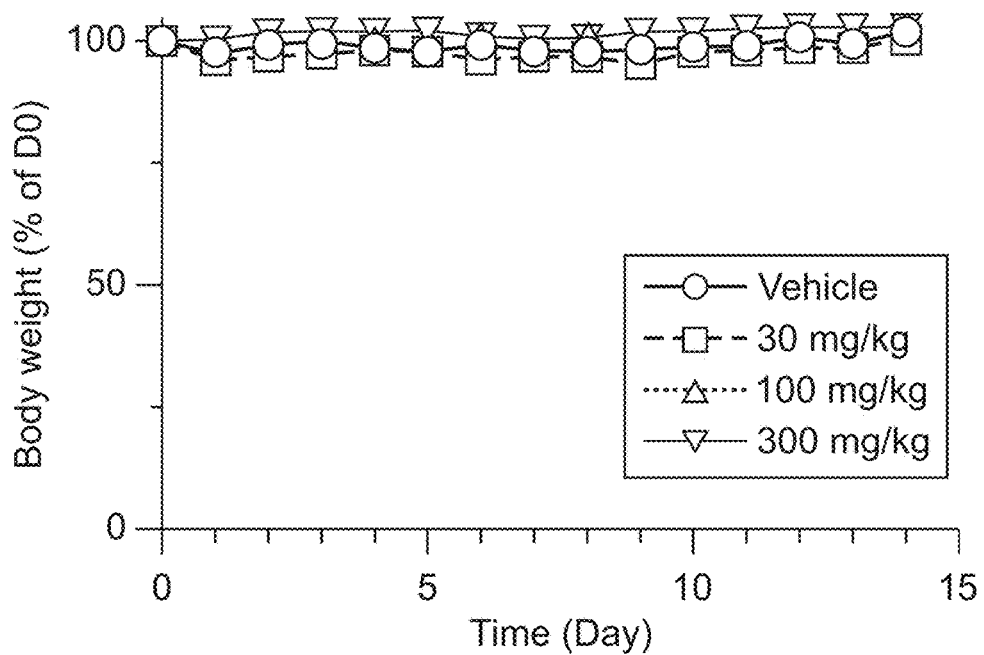
FIG. 4A-4B. In vivo safety: Repeat dosing of α-NETA does not affect body weight or vital organ weight/gross morphology. WT C567/BL6 mice were treated with various doses of α-NETA (300, 100, 30, 0 mg/kg) by oral gavage (in 10% captisol vehicle) daily for 14 days.
Figure 4B:
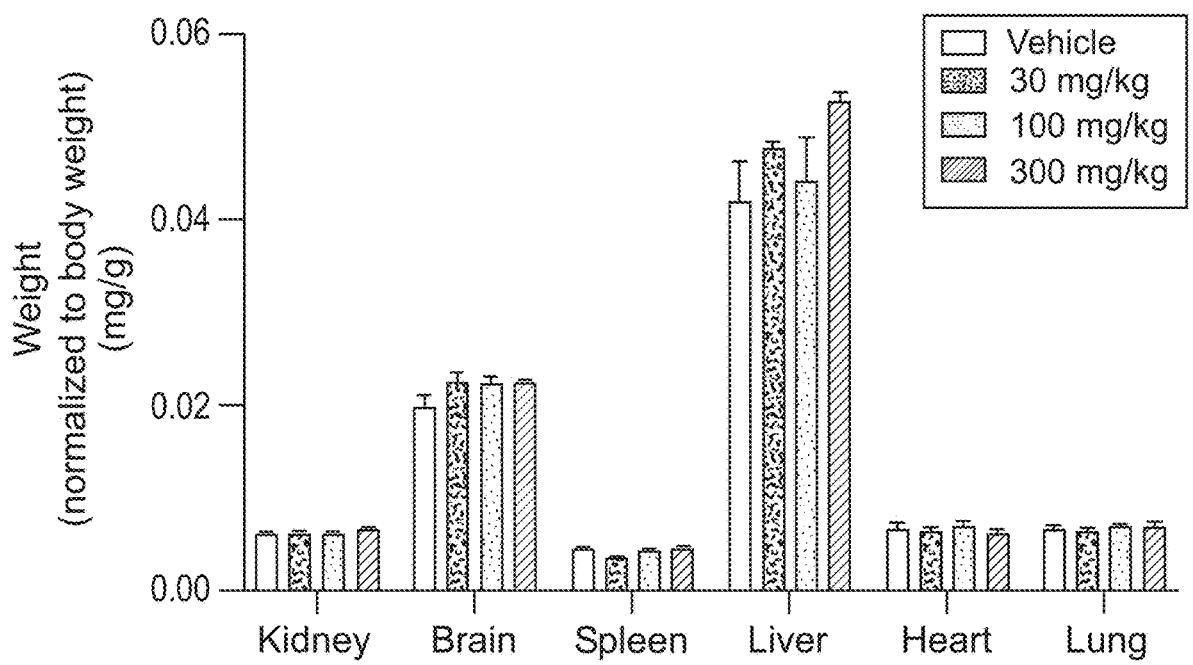

In vivo Toxicity Analysis for α-NETA. We assessed the acute single dose toxicity ($LD_{50}$) of α-NETA (p.o.). The calculated LD$_{50}$ was 873 mg/kg, (FIG. 3). Lethality was an off-target effect, as CMKLR1 KO mice also died following 1000 and 3000 mg/kg dosing. In repeat dosing safety studies, α-NETA administered for 14 days p.o. at up to 300 mg/kg/day had no effect on body weight (FIG. 4A) or the wet weight or gross morphological appearance of vital organs (FIG. 4B). Thus, the no-observable-adverse-effect-level (NOAEL) level for α-NETA in a repeated dosing regimen for up to 14 days is at least 300 mg/kg.

Figure 5:
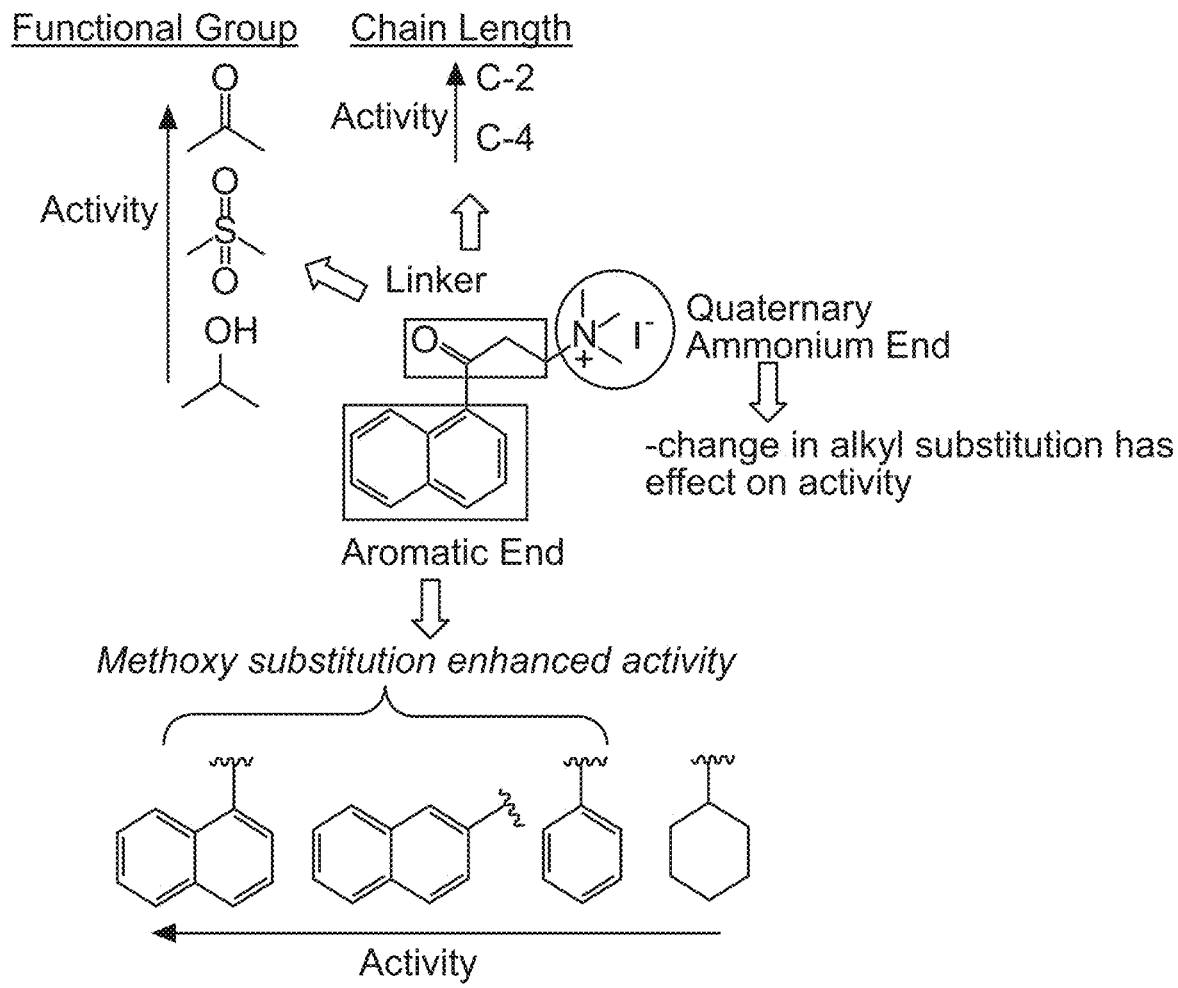
FIG. 5. SAR of α-NETA analogs for CMKLR1 inhibition. Thin arrows indicate structural features leading to increased potency.

Structure-Activity Relationship (SAR). α-NETA consists of: i) a quaternary ammonium end, ii) an aromatic end consisting of α-naphthyl group, and iii) a three-carbon linker with a carbonyl functional group (FIG. 5). We synthesized analogues of α-NETA by systematic modifications at these three sites to study the structure-activity relationship (SAR) using the β-arrestin2 assay.

Figure 6:
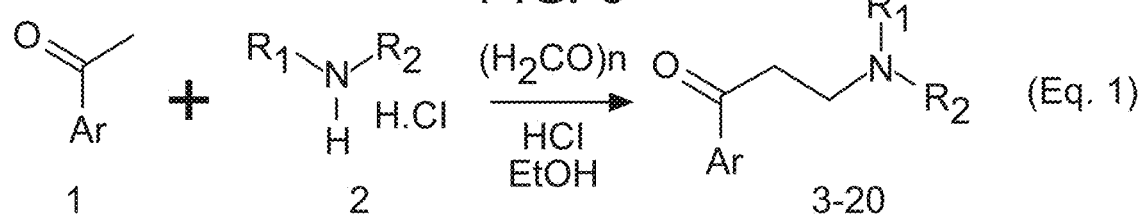
FIG. 6. Synthesis of tertiary amine α-NETA analogues with modified ammonium and aromatic groups FIG. 7. Synthesis of quaternary amine α-NETA analogues with modified aromatic groups.

In the first series of modifications we kept the linker as it is and modified the quaternary ammonium and aromatic ends of α-NETA. We synthesized a set of tertiary amines with varied N-alkyl substitutions and different aromatic rings. These compounds were synthesized from corresponding ketones 1 and hydrochloride salts of dialkylamines 2 using mannich reaction (FIG. 6, Eq 1) and screened for their activity using β-arrestin2 assay (Table 2). In case of α-naphthyl derivatives (compounds 3-5), β-arrestin2 inhibition activity increases with bulkier substitution on nitrogen. Similar structural-activity trend was also observed with phenyl derivatives (compounds 12 and 13). In contrast, activity decreases with bulkier N-substitution in 3-naphthyl derivatives. Effect of methoxy substitution at appropriate position also had prominent effect on the activity, as suggested by lower IC$_{50}$ values for compounds 6 and 19. The inhibitory effect of compound 6 on chemerin-dependent β-arrestin2 signaling was not significantly different from the effect of α-NETA (p>0.05 by two-tailed t-test) (Table 2). Replacing naphthyl group with cyclohexyl (compound 20) resulted in complete loss of activity (Table 2).

Figure 7:
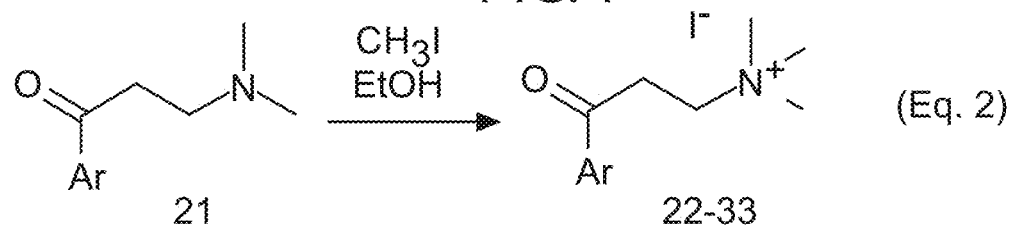

Next, we evaluated the effect of change in aromatic end on the β-arrestin2 activity, keeping quaternary ammonium end and linker unchanged (similar to α-NETA). Corresponding tertiary amines 21 were quaternized using methyl iodide to obtain desired compounds 22-33 (FIG. 7, Eq 2). β-arrestin2 assay showed a trend in the activity of these compounds decreasing in the following order: α-naphthyl (22, IC$_{50}$ 2.3 µM)>β-naphthyl (23, IC$_{50}$ 3.1 µM)>phenyl (24, IC$_{50}$ 4.3 µM)>cyclohexyl (25, IC$_{50}$ 11.9 µM)(Table 3). Interestingly, methoxy substitution on all the aromatic rings increased the potency. In general, ortho or para methoxy compounds (26, 27 and 30) showed higher β-arrestin2 activity in comparison to meta substituted derivatives (compounds 28 and 31). A secondary chemotaxis assay was also performed on selected hit compounds, which also showed higher potency for methoxy-substituted compounds (Table 3). Surprisingly, phenyl derivative 24 showed activity in β-arrestin2 assay but did not show any activity in chemotaxis assay, while the methoxy-substituted phenyl derivatives 26, 27 and 30 were highly active in both assays (Table 3). While the inhibitory effect of compound 27 on chemerin-dependent β-arrestin2 signaling was not significantly different from α-NETA (p>0.05 by two-tailed t-test), compound 27 inhibited chemerin-dependent cell migration with significantly better potency than α-NETA (p<0.05 by two-tailed t-test)(Table 3).

Figure 8:
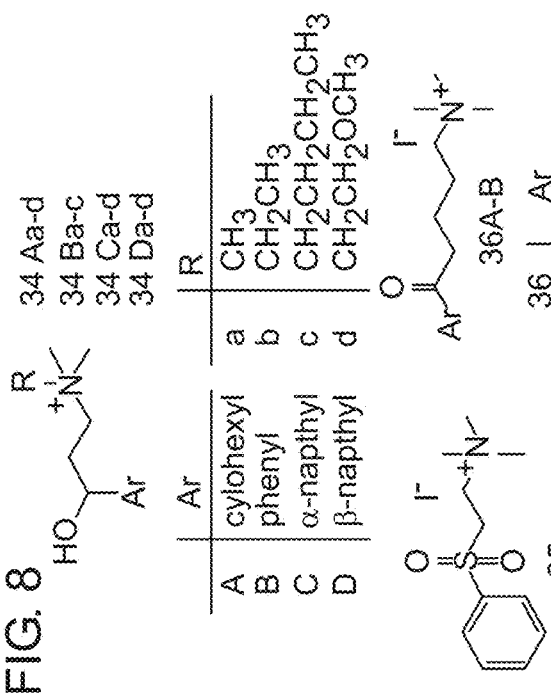
FIG. 8. Structures of α-NETA analogues with modified linker functional groups and chain length.

To further expand the SAR, the carbonyl functional group of the linker moiety of α-NETA derivatives was modified to hydroxyl and sulfone groups to obtain corresponding functionalized—quaternary ammonium salts 34A-D and 35, respectively (FIG. 8). However, all these compounds with modified functional group were inactive in β-arrestin2 assay. We also modified alkyl chain length of the linker from C-2 to C-4 carbons to obtain compounds 36A-B (FIG. 8). These compounds with elongated linker chain length were also inactive in β-arrestin2 assay.

Finally, we asked if new compounds generated via our preliminary SAR studies were effective in suppressing EAE. We were particularly interested to see if any of the new, more potent compounds were similarly more efficacious than α-NETA in vivo. We selected the comparatively more potent methoxy substituted derivative of α-NETA 27 and its tertiary amine counterpart 6 for in vivo testing. While 6 was similarly effective in suppressing the integrated clinical score as α-NETA, 27 proved to be superior to α-NETA in blunting severe EAE disease: both the maximum clinical score and the incidence of hind limb paralysis were significantly reduced by 27 vs. α-NETA (Table 4).

In this study, we investigated key efficacy, safety, and SAR features of CMKLR1 antagonist α-NETA. In terms of efficacy, α-NETA outperformed Tecfidera in suppressing clinical signs of EAE. With respect to safety, we did not identify any major liability for α-NETA in the industry-standard in vitro or in vivo toxicity studies investigated in this report. Through rationale medicinal chemistry modifications to α-NETA structure, we identified specific SAR among α-NETA domains and CMKLR1 inhibition. Importantly, we discovered new α-NETA analogs with improved CMKLR1 target potency, one of which proved superior to α-NETA in suppressing severe clinical EAE in vivo. Thus, α-NETA-based CMKLR1 small molecule antagonists offer a promising, developable approach to treat MS in the clinic.

Although Tecfidera was approved by the FDA for the treatment of MS in 2013, dimethyl fumarate and its metabolites have a long, 60-year history as an effective treatment for autoimmune psoriasis. Dimethyl fumarate has myriad biological effects when administered in vivo, making it difficult to define the cellular and molecular mechanisms underlying its efficacy. Tecfidera is thought to promote protective antioxidant activities via activation of nuclear factor erythroid-2-related factor (NRF2); and to modulate immune responses to both favor immune suppression and to restrict leukocyte infiltration into the CNS, possibly via agonizing hydroxycarboxylic acid receptor 2 (HCAR2). In vitro cell model studies and in vivo rodent studies support that dimethyl fumarate protects neurons from oxidative damage via activation/translocation of NRF2 to the nucleus, where it transcribes several anti-apoptotic, neuroprotective, and antioxidant genes (e.g. heme oxygenase-1 (HO-1), NAD(P)H quinone dehydrogenase 1 (NQO1), GSTP1 (others glutathione-S-transferase), superoxide dismutase-2 (SOD2), Sulfiredoxin-1 (SRXN1), and ferritin heavy chain 1 (FTH1). In MS patients, Tecfidera alters the composition of peripheral blood leukocytes to promote anti-inflammatory conditions, reducing absolute numbers and percentages of CD8+ T cells, CD45RO+CD4+ memory T cells, Th1 (CXCR3+) and Th17 (CCR6+) CD4+ T cells, memory B cells, and CD16+ CD56low NK cells; and increasing percentages of CD45RA+CD4+ naïve T cells, Th2 (CCR3+) CD4+ T cells, regulatory B cells, and CD16loCD56bright NK cells. In rodent EAE models, Tecfidera reduces leukocyte infiltration into the CNS, which correlates with preclinical efficacy. The aggregate effect of these diverse biological changes in many MS patients is clinical improvement.

The mechanism of action for α-NETA in suppressing EAE is consistent with inhibition of leukocyte infiltration into the CNS. Several recent studies also support a specific role for α-NETA in inhibiting chemerin/CMKLR1-associated functions in vivo: α-NETA blocked the recruitment of CMKLR1+DC into the CNS in EAE mice. α-NETA inhibited certain adipokine functions of chemerin mediated by CMKLR1, suppressing white fat deposition and liver steatosis induced by high fat diet challenge in vivo. In a germinal matrix hemorrhage brain injury model in neonatal rats, α-NETA reversed the protective effects of exogenous chemerin acting on CMKLR1+ microglia. α-NETA reduced the clonogenicity and viability of CMKLR1+ neuroblastoma cell lines in vitro, and reduced tumor growth in vivo in a preclinical neuroblastoma model.

In our EAE studies, the efficacy of Tecfidera in inhibiting clinical disease is not as striking as in previously published reports. Differences in our experimental design include the dose used for treatment, the drug vehicle (10% captisol in water), and the route of administration (s.c.), all of which were chosen to directly compare with α-NETA. Tecfidera has a dose dependent response in the MOG EAE model, and an effective dose for limiting clinical score is inconsistent amongst published reports. In some studies, 20 mg/kg Tecfidera was not efficacious; in others, 10 mg/kg daily dosing led to small but significant improvements in clinical scores. Daily doses of 200 mg/kg significantly suppressed clinical EAE, but these doses exceed by 2-3-fold the relevant clinical doses for MS patients. In the absence of pharmacokinetic data for α-NETA, we elected to dose both α-NETA and Tecfidera at 10 mg/kg daily based on our previous work, which showed significant efficacy for α-NETA in attenuating EAE without obvious adverse events.

The Food and Drug Administration (FDA) requires extensive preclinical in vitro and in vivo safety testing as part of an Investigative New Drug filing. In agreement with data deposited in PubChem (NCBI), our results indicate that α-NETA had little effect on hERG potassium channel-driven action potentials, and thus reduced predicted risk of cardiotoxicity in vivo (FIG. 2B). With respect to Cyp enzymes, α-NETA inhibited Cyp2B6 (IC50: 0.12 μM) and Cyp2C8 (1.5 μM)(Table 1). Cyp inhibition does not necessarily derail drug development (e.g. there are FDA-approved drugs (Orphenadrine, Gemfibrozil), that inhibit Cyp2B6 and Cyp2C8, respectively). However, use of Cyp inhibitors, particularly in combination with other drugs, requires additional patient monitoring to avoid adverse events related to drug-drug-interactions. While there were some minor differences in Cyp enzyme inhibition $IC_{50}$ values between publicly indexed PubChem data and our direct experimental data, there was a sizable discrepancy for Cyp3A4: we reported weak inhibition ($IC_{50}$: 7.4 μM), while PubChem listed the $IC_{50}$ as 0.2 μM. It is possible that the use of different substrates (Midazolam in our study, vs. luciferin-6' phenylpiperazinylyl in the PubChem-reported assay) could affect the $IC_{50}$ value. We therefore attempted the assay with testosterone as a third additional substrate. The $IC_{50}$ value in this case was 6.9 μM, in-line with our Midazolam results. Thus, for substrates that may be encountered in vivo, α-NETA is a weak Cyp3A4 inhibitor. In terms of in vivo safety assessment, our repeated dosing study in mice indicated that α-NETA was well-tolerated at doses up to 300 mg/kg p.o. for at least 14 days. Furthermore, the calculated single dose $LD_{50}$ for α-NETA was 873 mg/kg, which by comparison is safer than caffeine ($LD_{50}$ 367 mg/kg). A recent study reported that direct α-NETA injection (5 μg) into the uterine horn on days 6, 9 and 12 following fertilization resulted in significant embryo resorption, thus potentially contraindicating α-NETA for treatment during pregnancy.

In our initial studies, we used a cell-based chemerin-dependent signaling assay (β-arrestin2 inhibition) to identify α-NETA as a CMKLR1 inhibitor with an $IC_{50}$ value of 0.38 μM. In the SAR studies reported here, we again used β-arrestin2 inhibition assay, and in all cases compared the activity of newly generated compounds versus contemporaneously-tested α-NETA. Here it is worth mentioning that α-NETA obtained from different sources gave varied results. Therefore, to maintain consistency all compounds were prepared in our lab and characterized for purity (>98%) prior to any biological testing. It is known that live cell-based assays that quantify inhibitory signals are more sensitive to such variables than enzymatic or ligand binding assays. As a reference for comparison, Bentz et al. compared the interlaboratory variability of $IC_{50}$ values for 16 different inhibitors using a cell-based assay across 23 different research groups. The minimum difference in $IC_{50}$ values (e.g. the most consistent data) was 20-fold between the lowest and highest $IC_{50}$ values, while the maximum difference (e.g. the least consistent data) was 796-fold. While our experiments were conducted in the same lab, the studies were temporally separated by 4-5 years using different sources of α-NETA, and thus some differences in $IC_{50}$ values are expected. For SAR studies, contemporaneous comparison vs. parental α-NETA (and producing all compounds in-house) is crucial to identify improved-potency α-NETA-derivatives.

Overall SAR of our newly synthesized α-NETA analogues is summarized in FIG. 5. We made simple changes to modify three key sites of α-NETA to evaluate SAR, i.e. changing of ammonium head group, modification of length and functionality of the linker and changing the aromatic ring. Our studies indicated that the quaternary ammonium moiety is crucial for activity. Corresponding tertiary amines were comparatively less active in our assay. Any modification of the linker was also not tolerated. Compounds with modified functional groups or chain length did not show any activity. Changing the α-naphthyl to phenyl or a cyclohexyl ring reduced the activity, however, methoxy substitution at the aromatic rings significantly enhanced the β-arrestin2 activity (Table 3). These studies indicate that the aromatic ring of α-NETA is the only site where changes are tolerated. More diversified α-NETA analogues may be made by making complex changes at the aromatic ring site by incorporating heterocycles and substitutes aromatics.

In conclusion, our data shows that α-NETA is well-tolerated in vivo at efficacious and supra-efficacious doses, has a reasonable in vitro safety profile with respect to parameters commonly applied to early stage drug development programs, and is effective in suppressing demyelinating disease as compared to Tecfidera. Furthermore, we successfully identified SAR among α-NETA domains and CMKLR1 inhibition and discovered methoxy-substituted derivatives with enhanced potency in vitro and enhanced efficacy in vivo. Thus, CMKLR1 antagonist α-NETA provides a strong base molecule to use as a benchmark for the development of improved α-NETA derivatives for the treatment of MS and potentially other autoimmune or inflammatory disorders.

Methods

Mice. C57BL/6 mice were purchased from The Jackson Laboratory. Female mice (8-12 weeks old) were used in all experiments. Animal experiments were conducted in accordance with approved Veterans Affairs, National Institutes of Health, and Institutional Animal Care and Use Committee guidelines.

Cell culture. (hu)CMKLR1 transfectants (generated in L1.2 pre-B cell lymphoma cells) were grown in RPMI 1640 (Corning) supplemented with L-glutamine, penicillin-streptomycin, and 10% BCS and G418-sulfate (KSE Scientific). DiscoverX PathHunter® CHO-K1 CMKLR1 β-Arrestin Cells were grown in RPMI lacking phenol red (Gibco, Life Technologies), supplemented with L-glutamine, penicillin-streptomycin, sodium pyruvate, non-essential amino acid, BCS, hygromycin, and G418-sulfate.

β-arrestin recruitment assay. CMKLR1-CHO-β-Arrestin cells were seeded in 96 well plates at $1 \times 10^5$ cell/ml-100 ul/well and incubated overnight at 37° C., 5% $CO_2$. The next day, media was removed and cells were pre-incubated in PBS with α-NETA or test compound (95 ul/well) in a 6 point dose response curve from 100 μM to 0.3 μM for 10 min at RT. (α-NETA and test compounds were reconstituted in DMSO; final DMSO concentration in each well was 0.1%). After 10 min, 5 ul of recombinant human chemerin (R&D Systems) at a final concentration of 20 nM was added to each well. Plates were incubated for 90 min at 37° C., 5% $CO_2$. Media was then removed and 50 ul of chemiluminescent substrate (Tropix Gal-Screen, Applied Biosciences) was added. The plate was incubated for 1 hr at RT and luminescence was detected using the SpectraMax M5 plate reader (Molecular Devices). For each independent trial (single replicate dose curves), data was normalized to the maximum signal per compound tested and an IC50 value was generated using GraphPad Prism software. The average IC50 value for n independent trials (as specified in the table) is reported.

Chemotaxis assay. (hu)CMKLR1 L1.2 cells at $1 \times 10^6$ cell/ml were treated with 5 mM sodium butyrate (Sigma) overnight to induce hCMKLR1 expression. The next day, cells were washed in migration media (RPMI+0.5% BSA) and resuspended at $1.5-3 \times 10^6$ cell/ml. Cells were pre-incubated at RT for 10 min with various concentrations of α-NETA or test compounds (α-NETA and test compounds were reconstituted in DMSO; final DMSO concentration in each well was 0.1%). 100 ul of cells were added to the upper chamber of a 24-well transwell plate (5 um pore size, Costar). Cells were allowed to migrate toward huChemerin (0.6 mM in migration media, bottom chamber) for 2 h, 37° C., 5% $CO_2$. The number of migrated cells was quantified by flow cytometry (BD LSR2), and live cells were distinguished based on FSC×SSC properties. The background for this assay was typically low with 0 cells migrating to the buffer alone. For each independent trial, data was normalized to the maximum migration per compound tested and an IC50 value was generated using GraphPad Prism software. The average IC50 value for n independent trials (as specified in the table) is reported.

EAE. C57/BL6 mice were immunized (s.c. injection near inguinal LNs-50 ul per side) with 100 ul/mouse of a 1:1 emulsion of Complete Freund's Adjuvant (CFA): Myelin oligodendrocyte glycoprotein (MOG) peptide amino acids 35-35 (MEVGWYRSPFSRVVHLYRNGK), ($MOG_{35-55}$, Stanford Protein and Nucleic Acid Facility, Stanford, Calif.). CFA consisted of 5 mg/ml mTB (Mycobacterium-tuberculosis H37 Ra, BD Difco) in IFA (Incomplete Freund's Adjuvant, Sigma). $MOG_{35-55}$ was reconstituted at 2 mg/ml in PBS. Mice also received 200 ng pertussis toxin (List Biological Laboratories, Inc) by i.p. injection at the time of immunization and two days later. Mice were randomly assigned treatment groups and received daily treatments of α-NETA, DMF, compound: 27 or 6, (10 mg/kg in 10% captisol) or vehicle (10% captisol in water) via s.c. injection on the flank beginning at the time of disease induction and ending on day 21-27. The dose of α-NETA was chosen based on our previous work, which was efficacious and well-tolerated. For a direct comparison to α-NETA, the DMF and compound doses were also 10 mg/kg in 10% captisol. Mice were monitored daily for clinical disease and scored (0=normal/healthy, 1=limp tail, 2=hindlimb weakness, 3=hindlimb paralysis, 4=hindlimb and forelimb paralysis, 5=moribund/dead).

α-NETA acute toxicity. C57/BL6 mice received one treatment of α-NETA (formulated in 10% captisol, Cydex Pharmaceuticals) at the following doses: 3000, 1000, 300, 100, 30, 0 mg/kg by oral gavage (200 ul/dose, 3mice/group). Mouse survival was monitored and body weight was measured daily for 14 days. On day 14 the mice were euthanized and the wet weight for the following tissues: kidney, brain, spleen, liver, heart, and lung, was recorded.

α-NETA repeat dosing toxicity. Mice on the C57/BL6 background received daily treatment of α-NETA (formulated in 10% captisol) at the following doses: 300, 100, 30, 0 mg/kg by oral gavage (200 ul/dose, 3 mice/group) for 14 days. Mouse survival was monitored and body weight was measured daily for the length of the study. On day 14 the mice were euthanized and the wet weight for the following tissues: kidney, brain, spleen, liver, heart, and lung, was recorded.

Ames test. Ames test was completed using the AMES-MOD ISO 96 well format assay, Version 1.1 (Environmental Bio-Detection Products Inc.) according to manufacturer's instructions. In brief, Salmonella typhimurium (TA100) bacterial strain was exposed to the indicated doses of sodium azide (positive control) or α-NETA solubilized in DMSO (1% DMSO/well, 48 wells/dose completed in triplicate). After 2 h incubation the cells were diluted and cultured in media lacking histidine but containing pH indicator to identify revertant cell growth. After 3 days of incubation at 37° C., the number of wells containing revertant cells was counted per dose.

Cyp enzyme inhibition. Human liver microsomes were pre-incubated with 7 concentrations (0.1-100 mM, duplicate wells) of α-NETA for 30 min. Cyp-isoform-specific substrates were then added, incubated 10-60 min, substrate concentration quantified by mass spectrometry, and IC50s calculated (Cyprotex/Evotec AG).

Cyp induction. Pregnane X receptor (PXR) activation was used as a marker of Cyp induction. An engineered human hepatoma cell line with a PXR luciferase reporter was incubated with the indicated concentrations of α-NETA, Rifampicin (positive control), or DMSO (negative control), and luciferase activity assessed (Cyprotex/Evotec AG).

hERG inhibition. A patch-clamp assay with single CHO-hERG cell transfectants were used to quantify potential α-NETA-dependent hERG inhibition (2-3 cells per compound concentration). Basal hERG current was measured, and then α-NETA (0.008, 0.04, 0.2, 1, 5, 25 uM), Quinidine (positive control, a known hERG inhibitor) or DMSO (negative control) was added. The cell was depolarized, and the hERG tail current was measured, and IC50 determined (Cyprotex/Evotec AG).

Statistical Methods. All data are presented as mean with error calculated as SEM. Statistical comparisons were made using GraphPad Prism Software (San Diego, Calif., USA). Data was analyzed as indicated by a two tailed student's t-test when comparing two groups or a one-way analysis of variance (ANOVA) with either post-hoc Dunnett's multiple comparison test or Kruskal Wallis test for multiple group comparisons. An F-test (extra sum of squares) was used to compare the geometric features of the $4^{th}$ order polynomial curves fit to the clinical EAE data. Fisher's exact test was used to analyze the 2×2 contingency table (Table 4). A p value of <0.05 was considered statistically significant.

Synthesis of α-NETA analogues. General methods: TLCs were run on pre-coated Silica Gel 60F$_{254}$ plates from MilliporeSigma (Burlington, Mass., USA) and observed under UV light. Column chromatography was done using a CombiFlash Rf+ Lumen chromatography system from Teledyne ISCO (Lincon, Nebr., USA). For verification of the product and purity analysis, the LC-MS was taken on an Agilent 6490 iFunnel Triple Quadrupole Mass Spectrometer from Agilent Technologies Inc. (Santa Clara, Calif., USA). The $^1$H (400 MHz) and $^{13}$C (101 MHz) NMR spectra were taken on an Agilent 400-MR NMR spectrometer from Agilent Technologies Inc. (Santa Clara, Calif., USA). Chemical shifts (δ) are expressed in ppm, coupling constants (J) are expressed in Hertz, and splitting patterns are described as follows: s=singlet; d=doublet; t=triplet; q=quartet; br=broad; m=multiplet; dd=doublet of doublets; dt=doublet of triplets; td=triplet of doublets; ddd=doublet of doublet of doublets. All reagents and solvents were purchased from either Sigma-Aldrich (St. Louis, Mo., USA) or Fisher Scientific (Hampton, N.H., USA) and used without further purification.

General synthesis of tertiary amines 3-20: In a two-neck round-bottom flask, fitted with a reflux condenser was suspended aryl methyl ketone/cyclohexyl methyl ketone 1 (Table 2, 1.0 eq, 47 mmol) in ethanol (15 mL). Then disubstituted amine HCl salts 2 (1.4 eq, 65 mmol) and paraformaldehyde (1.4 eq, 65 mmol) were added. The mixture was stirred at room temperature for 5-10 min and conc. HCl (~0.6 mL) was added. The resulting mixture was stirred at refluxed for 18-24 h. The progress of the reaction was monitored by TLC. After cooling the mixture to ambient temperature, acetone (~50 mL) was added with continues stirring. The mixture was further cooled to −20° C. and the resulting solid was collected by filtration, washed with child acetone and dried in a vacuum for 1 h. The wet solid was dissolved in distilled water (~100 mL), and pH was adjusted to 9-11 by adding a saturated solution of Na$_2$CO$_3$. After stirring the solution at room temperature for 30 min, extracted with ethyl acetate (2×30 mL). combined organic layer was washed with water, brine, dried over Na$_2$SO$_4$, filtered and evaporated to dryness to afford a yellow oil, that was further purified on silica gel column with 0-5% methanol in dichloromethane that contains 1% triethyl amine to afford the desired compound as colorless to pale yellow oil. For compounds 4, 5, 10, 11 and 18, (Table 2) similar procedure was followed except the reaction was carried out in seal tube at 100° C. for 24 h.

General synthesis of quaternary ammonium salts 21-33: The tertiary amine 21 (Table 3, 1.0 eq, 1.0 mmol) was suspended in ethanol (5 mL) in a 14 mL glass vial then methyl iodide (1.2 eq, 1.2 mmol) was added dropwise at ambient temperature and stirred for 24 h, during which time the a white solid precipitated. The solid was collected by filtration and washed with copious amounts of ethanol followed by diethyl ether. The compounds were further purified by stirring them in mixture of acetonitrile and diethyl ether for overnight. The desired compounds were obtained as off-white to pale brown solids.

TABLE 1

| Cyp Inhibition | |
|---|---|
| Isoform | IC$_{50}$ (μM) |
| Cyp1A2 | 8[a] |
| Cyp2B6 | 0.12[b] |
| Cyp2C8 | 1.5[b] |
| Cyp2C9 | 14.6[b] |
| Cyp2C19 | 84[b] |
| Cyp2D6 | >10[c] |
| Cyp3A4 | 7.5[b] |

[a]PubChem BioAssay ID 1476
[b]Human liver microsomes were pre-incubated with α-NETA (0.1-100 mM, duplicate wells). IC50s values were calculated following incubation with cyp-specific substrates.
[c]PubChem BioAssay ID 1461

TABLE 2

| SAR of tertiary amines on CMKLR1 inhibition | | | | |
|---|---|---|---|---|
| Cmpd ID | Ar | R$_1$ | R$_2$ | β-arrestin IC$_{50}$ μM mean ± SEM (n) |
| α-NETA | | | | 4.9 ± 1.5 (18) |
| 3 | naphthalen-1-yl | Me | Me | 18.8 (1) |
| 4 | naphthalen-1-yl | Me | Et | 17.9 (1) |
| 5 | naphthalen-1-yl | Et | Et | 8.9 ± 2.4 (4) |

TABLE 2-continued
SAR of tertiary amines on CMKLR1 inhibition
| Cmpd ID | Ar | R₁ | R₂ | β-arrestin IC$_{50}$ μM mean ± SEM (n) |
|---|---|---|---|---|
| 6 | 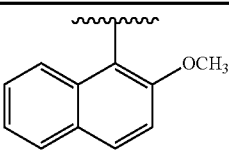 | Me | Me | 6.2 ± 2.5 (3) n.s. |
| 7 | 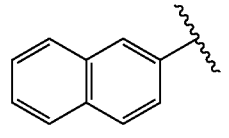 [SMILES: *c1ccc2ccccc2c1] | Me | Me | 18.5 (1) |
| 8 | 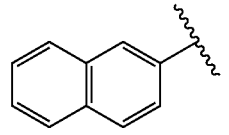 [SMILES: *c1ccc2ccccc2c1] | Et | Et | 71.3 (1) |
| 9 | 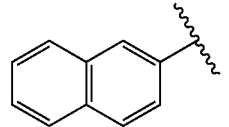 [SMILES: *c1ccc2ccccc2c1] | Me | Et | 39.6 (1) |
| 10 | 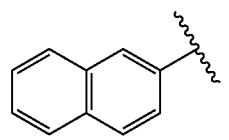 [SMILES: *c1ccc2ccccc2c1] | Me | Bu | 44.5 (1) |
| 11 | 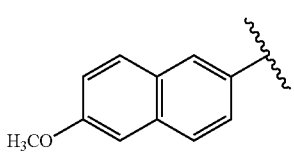 [SMILES: *c1ccc2cc(OC)ccc2c1] | Me | Me | >100 (2) |
| 12 | 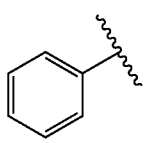 [SMILES: *c1ccccc1] | Me | Me | >100 (1) |
| 13 | 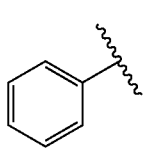 [SMILES: *c1ccccc1] | Me | Et | 16.8 ± 8.3 (3) |
| 14 | 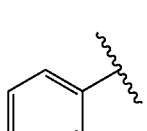 | Et | Et | 77.8 (1) |
| 15 | 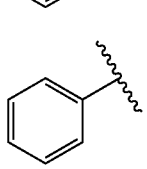 | Me | Bu | >100 (4) |

TABLE 2-continued

SAR of tertiary amines on CMKLR1 inhibition

| Cmpd ID | Ar | $R_1$ | $R_2$ | β-arrestin $IC_{50}$ μM mean ± SEM (n) |
|---|---|---|---|---|
| 16 | 2-methoxyphenyl | Me | Me | >100 (1) |
| 17 | 4-methoxyphenyl | Me | Me | >100 (1) |
| 18 | 3-methoxyphenyl | Me | Me | 64 (1) |
| 19 | 2,6-dimethoxyphenyl | Me | Me | 10.3 ± 4.5 (4) |
| 20 | cyclohexyl | Me | Me | >100 (1) | n.s., not significant by two-tailed t-test vs. α-NETA

TABLE 3

SAR of aryl group on CMKLR1 inhibition

| Cmpd ID | Ar | β-arrestin $IC_{50}$ μM mean ± SEM (n) | Chemotaxis $IC_{50}$ μM mean ± SEM (n) |
|---|---|---|---|
| 22 (α-NETA) | naphthalen-1-yl | 4.9 ± 1.5 (18) | 37.0 ± 8.9 (6) |
| 23 | naphthalen-2-yl | 2.5 ± 0.9 (5) | 24.1 (1) |

TABLE 3-continued

SAR of aryl group on CMKLR1 inhibition

| Cmpd ID | Ar | β-arrestin IC$_{50}$ μM mean ± SEM (n) | Chemotaxis IC$_{50}$ μM mean ± SEM (n) |
| --- | --- | --- | --- |
| 24 | phenyl | 5.6 ± 0.7 (6) | >100 (1) |
| 25 | cyclohexyl | 11.9 (1) | >100 (1) |
| 26 | 2-methoxyphenyl | 2.9 ± 1.6 (5) | 7.2 (1) |
| 27 | 4-methoxyphenyl | 1.9 ± 0.2 (8) n.s. | 4.5 ± 1.5 (3) * |
| 28 | 3-methoxyphenyl | 3.8 ± 1.7 (4) | 14.6 ± 4.8 (2) |
| 29 | 2,4-dimethoxyphenyl | 4.8 ± 1.6 (8) | 17.4 ± 2.2 (4) |
| 30 | 2,6-dimethoxyphenyl | 2.1 ± 1.1 (7) | 6.8 (1) |
| 31 | 3,5-dimethoxyphenyl | 6.0 ± 2.2 (6) | >100 (4) |
| 32 | 6-methoxynaphthalen-2-yl | 1.5 ± 0.3 (3) | 20 ± 6.2 (3) |

TABLE 3-continued

SAR of aryl group on CMKLR1 inhibition

| Cmpd ID | Ar | β-arrestin IC$_{50}$ μM mean ± SEM (n) | Chemotaxis IC$_{50}$ μM mean ± SEM (n) |
|---|---|---|---|
| 33 | naphthyl-OCH$_3$ | 0.6 ± 0.3 (3) | 10.7 (1) | n.s., not significant by two-tailed t-test vs. α-NETA
* p < 0.05 by two-tailed t-test vs. α-NETA

TABLE 4

α-NETA and analogs 27 and 6 suppress clinical EAE

| Treatment Group | AUC (Mean ± SEM) | Day of onset (Mean ± SEM) | Maximum Score (Mean ± SEM) | Incidence of hind limb paralysis |
|---|---|---|---|---|
| Vehicle | 44.7 ± 5.5 | 12.5 ± 0.7 | 2.9 ± 0.1 | 7/8 (87.5%) |
| α-NETA | 31.9 ± 4.0* | 14.4 ± 0.6* | 2.6 ± 0.2 | 5/8 (62.5%) |
| 27 | 24.3 ± 4.2* | 16.0 ± 0.9* | 2.1 ± 0.1¶ | 1/8 (12.5%)§ |
| 6 | 25.2 ± 4.0* | 14.5 ± 0.4* | 2.4 ± 0.2 | 3/8 (37.5%) |

EAE was induced in WT C57/BL6 mice by active immunization with MOG$_{35-55}$/CFA/PTX and monitored daily for clinical signs as previously described. Mice were treated with α-NETA, 6, 27 (10 mg/kg), or vehicle (10% captisol) daily, beginning at the time of disease induction and ending on D 21. n = 8 mice per group. AUC = area under the curve, calculated for each individual mouse as mean clinical score × day.
*p < 0.05, as determined one-way ANOVA compared to vehicle
¶p < 0.05 as determined by t-test compared to α-NETA
§p < 0.05 as determined by Chi-square (2 x 2 contingency table) test compared to α-NETA General Methods:

TLCs were run on pre-coated Silica Gel 60F$_{254}$ plates from MilliporeSigma (Burlington, Mass., USA) and observed under UV light. Column chromatography was done using a CombiFlash Rf+ Lumen chromatography system from Teledyne ISCO (Lincon, Nebr., USA). For verification of the product and purity analysis, the LC-MS was taken on an Agilent 6490 iFunnel Triple Quadrupole Mass Spectrometer from Agilent Technologies Inc. (Santa Clara, Calif., USA). The $^1$H (400 MHz) and $^{13}$C (101 MHz) NMR spectra were taken on a Agilent 400-MR NMR spectrometer from Agilent Technologies Inc. (Santa Clara, Calif., USA). Chemical shifts (δ) are expressed in ppm, coupling constants (J) are expressed in Hertz, and splitting patterns are described as follows: s=singlet; d=doublet; t=triplet; q=quartet; br=broad; m=multiplet; dd=doublet of doublets; dt=doublet of triplets; td=triplet of doublets; ddd=doublet of doublet of doublets. All reagents and solvents were purchased from either Sigma-Aldrich (St. Louis, Mo., USA) or Fisher Scientific (Hampton, N.H., USA) and used without further purification.
Chemistry Experimental
General Methods:

TLCs were run on pre-coated Silica Gel 60F$_{254}$ plates from MilliporeSigma (Burlington, Mass., USA) and observed under UV light. Column chromatography was done using a CombiFlash Rf+ Lumen chromatography system from Teledyne ISCO (Lincon, Nebr., USA). For verification of the product and purity analysis, the LC-MS was taken on an Agilent 6490 iFunnel Triple Quadrupole Mass Spectrometer from Agilent Technologies Inc. (Santa Clara, Calif., USA). The $^1$H (400 MHz) and $^{13}$C (101 MHz) NMR spectra were taken on a Agilent 400-MR NMR spectrometer from Agilent Technologies Inc. (Santa Clara, Calif., USA). Chemical shifts (δ) are expressed in ppm, coupling constants (J) are expressed in Hertz, and splitting patterns are described as follows: s=singlet; d=doublet; t=triplet; q=quartet; br=broad; m=multiplet; dd=doublet of doublets; dt=doublet of triplets; td=triplet of doublets; ddd=doublet of doublet of doublets. All reagents and solvents were purchased from either Sigma-Aldrich (St. Louis, Mo., USA) or Fisher Scientific (Hampton, N.H., USA) and used without further purification.

General synthesis of tertiary amines 3-20: In a two-neck round-bottom flask, fitted with a reflux condenser was suspended aryl methyl ketone/cyclohexyl methyl ketone 1 (Table 2, 1.0 eq, 47 mmol) in ethanol (15 mL). Then disubstituted amine HCl salts 2 (1.4 eq, 65 mmol) and paraformaldehyde (1.4 eq, 65 mmol) were added. The mixture was stirred at room temperature for 5-10 min and conc. HCl (~0.6 mL) was added. The resulting mixture was stirred at refluxed for 18-24 h. The progress of the reaction was monitored by TLC. After cooling the mixture to ambient temperature, acetone (~50 mL) was added with continues stirring. The mixture was further cooled to −20° C. and the resulting solid was collected by filtration, washed with child acetone and dried in a vacuum for 1 h. The wet solid was dissolved in distilled water (~100 mL), and pH was adjusted to 9-11 by adding a saturated solution of Na$_2$CO$_3$. After stirring the solution at room temperature for 30 min, extracted with ethyl acetate (2×30 mL). combined organic layer was washed with water, brine, dried over Na$_2$SO$_4$, filtered and evaporated to dryness to afford a yellow oil, that was further purified on silica gel column with 0-5% methanol in dichloromethane that contains 1% triethyl amine to afford the desired compound as colorless to pale yellow oil.

For compounds 4, 5, 10, 11 and 18, (Table 2) similar procedure was followed except the reaction was carried out in seal tube at 100° C. for 24 h.

3: Obtained in 51% yield as pale yellow oil. $^1$H NMR (400 MHz, Chloroform-d) δ 8.60-8.53 (m, 1H), 8.01-7.95 (m, 1H), 7.90-7.83 (m, 2H), 7.61-7.44 (m, 3H), 3.23 (dd, J=7.8, 6.8 Hz, 2H), 2.81 (dd, J=7.7, 6.9 Hz, 2H), 2.28 (s, 6H). $^{13}$C NMR (101 MHz, cdcl$_3$) δ 203.48, 136.11, 133.93, 132.48, 130.09, 128.34, 127.80, 127.26, 126.41, 125.79, 124.33, 54.71, 45.47, 40.54. LC-MS (ESI-TOF): m/z 228.30 ([C$_{15}$H$_{17}$NO+H]$^+$ calcd 228.13).

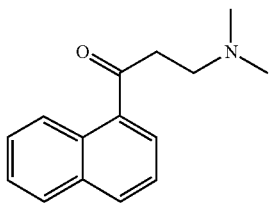 [SMILES: CN(C)CCC(=O)c1cccc2ccccc12]

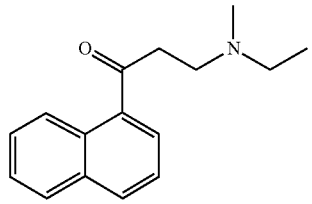 [SMILES: CCN(C)CCC(=O)c1cccc2ccccc12]

4: Obtained in 44% yield as colorless oil. ¹H NMR (400 MHz, Chloroform-d) δ 8.57 (ddt, J=8.6, 1.5, 0.8 Hz, 1H), 7.96 (dt, J=8.3, 1.1 Hz, 1H), 7.86 (dt, J=7.5, 1.4 Hz, 2H), 7.62-7.42 (m, 3H), 3.23 (dd, J=7.8, 6.8 Hz, 2H), 2.88 (dd, J=7.8, 6.8 Hz, 2H), 2.45 (q, J=7.2 Hz, 2H), 2.26 (s, 3H), 1.04 (t, J=7.2 Hz, 3H). ¹³C NMR (101 MHz, cdcl₃) δ 203.79, 136.19, 133.94, 132.44, 130.12, 128.34, 127.77, 127.26, 126.40, 125.85, 124.33, 52.46, 51.39, 41.56, 40.21, 12.33. LC-MS (ESI-TOF): m/z 242.30 ([C₁₆H₁₉NO+H]⁺ calcd 242.16).

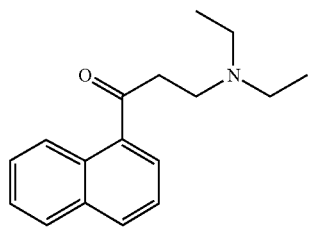 [SMILES: CCN(CC)CCC(=O)c1cccc2ccccc12]

5: Obtained in 14% yield as light brown oil. ¹H NMR (400 MHz, Chloroform-d) δ 8.62-8.51 (m, 1H), 8.02-7.92 (m, 1H), 7.86 (ddt, J=8.0, 2.1, 1.0 Hz, 2H), 7.63-7.41 (m, 4H), 3.28-3.15 (m, 2H), 3.03-2.91 (m, 2H), 2.55 (q, J=7.2 Hz, 4H), 1.01 (t, J=7.2 Hz, 6H). ¹³C NMR (101 MHz, cdcl₃) δ 204.13, 136.26, 133.94, 132.41, 130.14, 128.33, 127.73, 127.29, 126.38, 125.89, 124.33, 48.35, 46.87, 39.95, 11.74. LC-MS (ESI-TOF): m/z 256.30 ([C₁₇H₂₁NO+H]⁺ calcd 256.16).

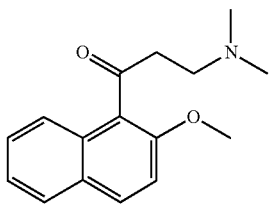 [SMILES: COc1ccc2ccccc2c1C(=O)CCN(C)C]

6: Obtained in 58% yield as pale yellow oil. ¹H NMR (400 MHz, Chloroform-d) δ 7.87 (dt, J=9.1, 0.6 Hz, 1H), 7.78 (ddt, J=8.2, 1.3, 0.6 Hz, 1H), 7.72 (dq, J=8.5, 0.9 Hz, 1H), 7.45 (ddd, J=8.4, 6.8, 1.4 Hz, 1H), 7.35 (ddd, J=8.1, 6.8, 1.2 Hz, 1H), 7.29-7.23 (m, 1H), 3.95 (s, 3H), 3.18-3.06 (m, 2H), 2.78 (dd, J=7.9, 6.9 Hz, 2H), 2.25 (s, 6H). ¹³C NMR (101 MHz, cdcl₃) δ 206.38, 153.75, 131.37, 130.59, 128.82, 128.07, 127.56, 124.91, 124.07, 123.72, 112.65, 56.34, 53.99, 45.39, 43.35. LC-MS (ESI-TOF): m/z 258.20 ([C₁₆H₁₉NO₂+H]⁺ calcd 258.14).

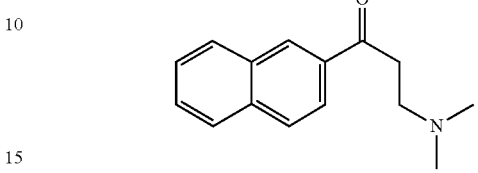

7: Obtained in 38% yield as off white semi solid. ¹H NMR (400 MHz, Chloroform-d) δ 8.50-8.39 (m, 1H), 8.02 (dd, J=8.6, 1.8 Hz, 1H), 7.94 (ddd, J=7.9, 1.5, 0.7 Hz, 1H), 7.90-7.79 (m, 2H), 7.62-7.45 (m, 2H), 3.26 (dd, J=7.9, 6.8 Hz, 2H), 2.80 (dd, J=7.8, 6.9 Hz, 2H), 2.30 (s, 6H). ¹³C NMR (101 MHz, cdcl₃) δ 199.04, 135.54, 134.22, 132.48, 129.69, 129.56, 128.44, 128.43, 127.74, 126.74, 123.83, 54.55, 45.59, 37.02. LC-MS (ESI-TOF): m/z 228.30 ([C₁₅H₁₇NO+H]⁺ calcd 228.13).

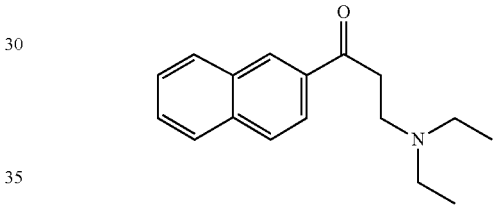

8: Obtained in 44% yield as brown oil. ¹H NMR (400 MHz, Chloroform-d) δ 8.52-8.41 (m, 1H), 8.02 (dd, J=8.6, 1.8 Hz, 1H), 7.94 (ddd, J=7.9, 1.5, 0.7 Hz, 1H), 7.90-7.79 (m, 2H), 7.62-7.47 (m, 2H), 3.33-3.17 (m, 2H), 3.04-2.87 (m, 2H), 2.59 (q, J=7.1 Hz, 4H), 1.06 (t, J=7.1 Hz, 6H). ¹³C NMR (101 MHz, cdcl₃) δ 199.69, 135.53, 134.35, 132.50, 129.73, 129.54, 128.42, 128.39, 127.74, 126.73, 123.84, 48.04, 47.04, 36.54, 11.87. LC-MS (ESI-TOF): m/z 256.30 ([C₁₇H₂₁NO+H]⁺ calcd 256.16).

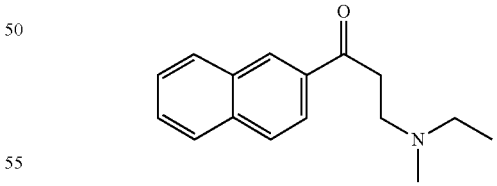

9: Obtained in 62% yield as colorless oil. ¹H NMR (400 MHz, Chloroform-d) δ 8.50-8.43 (m, 1H), 8.02 (dd, J=8.6, 1.8 Hz, 1H), 7.94 (ddt, J=7.9, 1.4, 0.7 Hz, 1H), 7.90-7.80 (m, 2H), 7.56 (dddd, J=18.8, 8.2, 6.9, 1.4 Hz, 2H), 3.34-3.21 (m, 2H), 2.89 (dd, J=8.1, 6.8 Hz, 2H), 2.50 (q, J=7.2 Hz, 2H), 2.30 (s, 3H), 1.09 (t, J=7.2 Hz, 3H). ¹³C NMR (101 MHz, cdcl₃) δ 199.32, 135.55, 134.29, 132.51, 129.70, 129.55, 128.43, 128.41, 127.74, 126.73, 123.83, 52.19, 51.48, 41.72, 36.75, 12.37. LC-MS (ESI-TOF): m/z 242.20 ([C₁₆H₁₉NO+H]⁺ calcd 242.15).

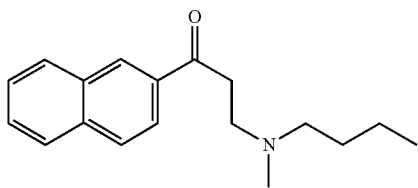 [SMILES: CCCCN(C)CCC(=O)c1ccc2ccccc2c1]

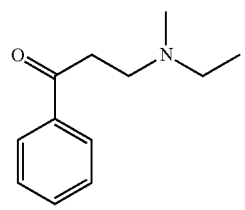

10: Obtained in 63% yield as colorless oil. $^1$H NMR (400 MHz, Chloroform-d) δ 8.48 (d, J=1.3 Hz, 1H), 8.03 (dd, J=8.6, 1.8 Hz, 1H), 7.96 (ddt, J=7.9, 1.5, 0.7 Hz, 1H), 7.92-7.81 (m, 2H), 7.57 (dddd, J=18.7, 8.2, 6.9, 1.4 Hz, 2H), 3.35-3.20 (m, 2H), 2.89 (dd, J=8.1, 6.8 Hz, 2H), 2.49-2.36 (m, 2H), 2.31 (s, 3H), 1.55-1.40 (m, 2H), 1.40-1.25 (m, 2H), 0.91 (t, J=7.3 Hz, 3H). $^{13}$C NMR (101 MHz, cdcl$_3$) δ 199.46, 135.54, 134.29, 132.50, 129.72, 129.56, 128.44, 128.42, 127.75, 126.74, 123.84, 57.64, 52.65, 42.37, 36.71, 29.52, 20.70, 14.10. LC-MS (ESI-TOF): m/z 270.30 ([C$_{18}$H$_{23}$NO+H]$^+$ calcd 270.18).

13: Obtained in 63% yield as light brown oil. $^1$H NMR (400 MHz, Chloroform-d) δ 7.96-7.86 (m, 2H), 7.55-7.46 (m, 1H), 7.45-7.35 (m, 2H), 3.11 (dd, J=8.1, 6.7 Hz, 2H), 2.79 (dd, J=8.1, 6.7 Hz, 2H), 2.43 (q, J=7.2 Hz, 2H), 2.23 (s, 3H), 1.02 (t, J=7.2 Hz, 3H). $^{13}$C NMR (101 MHz, cdcl$_3$) δ 199.30, 136.92, 132.98, 128.56, 128.54, 127.98, 127.97, 51.97, 51.41, 41.66, 36.59, 12.34. LC-MS (ESI-TOF): m/z 192.30 ([C$_{12}$H$_{17}$NO+H]$^+$ calcd 192.13).

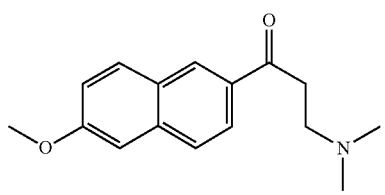

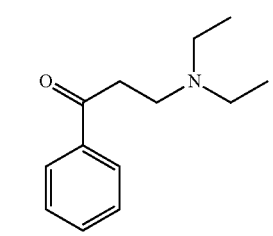

11: Obtained in 65% yield as off white solid. $^1$H NMR (400 MHz, Chloroform-d) δ 8.41 (d, J=1.7 Hz, 1H), 8.00 (ddd, J=8.6, 1.9, 0.6 Hz, 1H), 7.85 (dt, J=8.9, 0.6 Hz, 1H), 7.76 (dt, J=8.6, 0.6 Hz, 1H), 7.29-7.11 (m, 2H), 3.94 (d, J=0.6 Hz, 3H), 3.33-3.20 (m, 2H), 2.82 (t, J=7.4 Hz, 2H), 2.33 (d, J=0.6 Hz, 6H). $^{13}$C NMR (101 MHz, cdcl$_3$) δ 198.71, 159.74, 137.27, 132.31, 131.13, 129.59, 127.81, 127.13, 124.58, 119.71, 105.71, 55.41, 54.61, 45.52, 36.78. LC-MS (ESI-TOF): m/z 258.30 ([C$_{16}$H$_{19}$NO$_2$+H]$^+$ calcd 258.14)

14: Obtained in 29% yield as colorless oil. $^1$H NMR (400 MHz, Chloroform-d) δ 8.01-7.91 (m, 2H), 7.60-7.51 (m, 1H), 7.50-7.41 (m, 2H), 3.18-3.08 (m, 2H), 2.97-2.89 (m, 2H), 2.58 (q, J=7.1 Hz, 4H), 1.05 (t, J=7.1 Hz, 6H). $^{13}$C NMR (101 MHz, cdcl$_3$) δ 199.74, 137.05, 132.96, 128.55, 128.02, 47.87, 47.02, 36.43, 11.84. LC-MS (ESI-TOF): m/z 206.30 ([C$_{13}$H$_{19}$NO+H]$^+$ calcd 206.15).

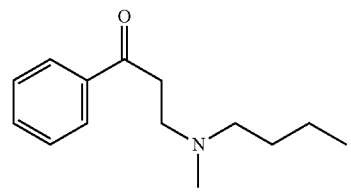

15: Obtained in 73% yield as colorless oil. $^1$H NMR (400 MHz, Chloroform-d) δ 7.98-7.90 (m, 2H), 7.57-7.49 (m, 1H), 7.48-7.39 (m, 2H), 3.18-3.08 (m, 2H), 2.85-2.76 (m, 2H), 2.41-2.32 (m, 2H), 2.25 (s, 3H), 1.50-1.38 (m, 2H), 1.34-1.23 (m, 2H), 0.89 (t, J=7.3 Hz, 3H). $^{13}$C NMR (101 MHz, cdcl$_3$) δ 199.45, 137.00, 132.96, 128.55, 128.01, 57.56, 52.50, 42.29, 36.60, 29.49, 20.63. LC-MS (ESI-TOF): m/z 220.30 ([C$_{14}$H$_{21}$NO+H]$^+$ calcd 220.16).

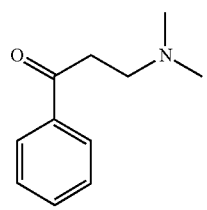

12: Obtained in 67.5% yield as colorless oil. $^1$H NMR (400 MHz, Chloroform-d) δ 7.98-7.92 (m, 2H), 7.58-7.51 (m, 1H), 7.48-7.40 (m, 2H), 3.21-3.08 (m, 2H), 2.75 (dd, J=7.9, 6.8 Hz, 2H), 2.28 (s, 6H). $^{13}$C NMR (101 MHz, cdcl$_3$) δ 199.11, 133.06, 128.59, 128.02, 54.35, 45.53, 36.91. LC-MS (ESI-TOF): m/z 178.30 ([C$_{11}$H$_{15}$NO+H]$^+$ calcd 178.12).

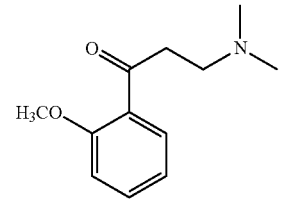

16: Obtained in 44% yield as colorless oil. $^1$H NMR (400 MHz, Chloroform-d) δ 7.66 (ddd, J=7.7, 1.8, 0.4 Hz, 1H), 7.43 (ddd, J=8.3, 7.3, 1.8 Hz, 1H), 7.01-6.90 (m, 2H), 3.88 (d, J=0.3 Hz, 3H), 3.21-3.09 (m, 2H), 2.72-2.63 (m, 2H), 2.25 (d, J=0.5 Hz, 6H). $^{13}$C NMR (101 MHz, cdcl$_3$) δ 201.44, 158.44, 133.34, 130.29, 128.36, 120.62, 111.43, 55.44, 54.46, 45.47, 42.06. LC-MS (ESI-TOF): m/z 208.30 ([C$_{12}$H$_{17}$NO$_2$+H]$^+$ calcd 208.13).

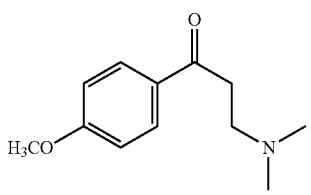

17: Obtained in 51% yield as colorless oil. $^1$H NMR (400 MHz, Chloroform-d) δ 7.92 (dd, J=9.0, 0.9 Hz, 2H), 6.90 (dd, J=9.0, 0.9 Hz, 2H), 3.83 (d, J=1.0 Hz, 3H), 3.13-3.02 (m, 2H), 2.71 (td, J=7.4, 0.8 Hz, 2H), 2.26 (d, J=0.9 Hz, 6H). $^{13}$C NMR (101 MHz, cdcl$_3$) δ 197.63, 163.42, 130.28, 130.02, 113.70, 55.42, 54.58, 45.50, 36.56. LC-MS (ESI-TOF): m/z 208.30 ([C$_{12}$H$_{17}$NO$_2$+H]$^+$ calcd 208.13).

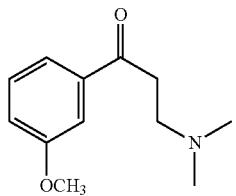

18: Obtained in 53% yield as pale yellow oil. $^1$H NMR (400 MHz, Chloroform-d) δ 7.52 (dddd, J=7.6, 1.5, 1.0, 0.4 Hz, 1H), 7.46 (dd, J=2.7, 1.6 Hz, 1H), 7.34 (dd, J=8.2, 7.7 Hz, 1H), 7.08 (dddd, J=8.2, 2.6, 1.0, 0.5 Hz, 1H), 3.82 (dd, J=1.4, 0.5 Hz, 4H), 3.11 (dd, J=7.7, 6.9 Hz, 2H), 2.72° (dd, J=7.9, 6.8 Hz, 2H), 2.26 (s, 6H). $^{13}$C NMR (101 MHz, cdcl$_3$) δ 198.89, 159.80, 138.28, 129.55, 120.64, 119.50, 112.26, 55.38, 54.41, 45.49, 37.01, 26.68. LC-MS (ESI-TOF): m/z 208.20 ([C$_{12}$H$_{17}$NO$_2$+H]$^+$ calcd 208.13).

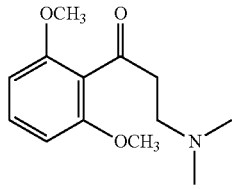 [SMILES: COc1cccc(OC)c1C(=O)CCN(C)C]

19: Obtained in 54% yield as colorless oil. $^1$H NMR (400 MHz, Chloroform-d) δ 7.28-7.18 (m, 1H), 6.52 (dd, J=8.4, 0.7 Hz, 2H), 3.75 (d, J=0.9 Hz, 6H), 2.92 (ddd, J=8.3, 6.7, 0.6 Hz, 2H), 2.74-2.63 (m, 2H), 2.22 (d, J=0.8 Hz, 6H). $^{13}$C NMR (101 MHz, cdcl$_3$) δ 203.66, 156.68, 130.59, 120.27, 103.92, 103.86, 55.77, 53.38, 45.33, 42.96. LC-MS (ESI-TOF): m/z 238.30 ([C$_{13}$H$_{19}$NO$_3$+H]$^+$ calcd 238.14).

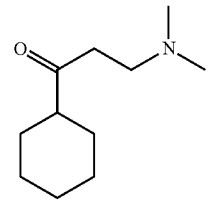

20: Obtained in 28% yield as pale yellow oil. $^1$H NMR (400 MHz, Chloroform-d) δ 2.61-2.54 (m, 2H), 2.54-2.48 (m, 2H), 2.37-2.25 (m, 1H), 2.18 (s, 6H), 1.88-1.68 (m, 4H), 1.67-1.57 (m, 1H), 1.37-1.07 (m, 5H). $^{13}$C NMR (101 MHz, cdcl$_3$) δ 212.86, 53.83, 50.99, 45.43, 38.86, 28.39, 25.81, 25.62. LC-MS (ESI-TOF): m/z 184.30 ([C$_{11}$H$_{21}$NO+H]$^+$ calcd 184.16).

General Synthesis of Quaternary Ammonium Salts 22-33

The tertiary amine 21 (Table 3, 1.0 eq, 1.0 mmol) was suspended in ethanol (5 mL) in a 14 mL glass vial then methyl iodide (1.2 eq, 1.2 mmol) was added dropwise at ambient temperature and stirred for 24 h, during which time the a white solid precipitated. The solid was collected by filtration and washed with copious amounts of ethanol followed by diethyl ether. The compounds were further purified by stirring them in mixture of acetonitrile and diethyl ether for overnight. The desired compounds were obtained as off-white to pale brown solids.

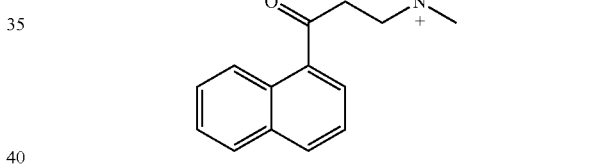

22: Obtained in 58% yield as off white solid. $^1$H NMR (400 MHz, DMSO-d$_6$) δ 8.62-8.54 (m, 1H), 8.32 (dd, J=7.3, 1.2 Hz, 1H), 8.20 (dt, J=8.4, 1.0 Hz, 1H), 8.06-7.99 (m, 1H), 7.71-7.53 (m, 3H), 3.79 (s, 4H), 3.16 (s, 9H). $^{13}$C NMR (101 MHz, dmso) δ 200.22, 134.27, 133.93, 133.83, 129.84, 129.08, 128.56, 126.97, 125.68, 125.20, 61.47 (t, J=4 Hz), 54.86 (t, J=4 Hz), 53.11 (t, J=4 Hz), 35.39. LC-MS (ESI-TOF): m/z 242.30 (C$_{16}$H$_{20}$NO$^+$ calcd 242.15).

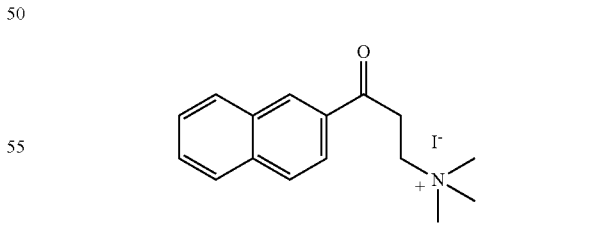

23: Obtained in 34% yield as off white solid. 1H NMR (400 MHz, DMSO-d$_6$) δ 8.81 (q, J=1.2 Hz, 1H), 8.19-8.11 (m, 1H), 8.11-8.00 (m, 3H), 7.76-7.61 (m, 2H), 3.93-3.81 (m, 2H), 3.77 (ddd, J=8.3, 6.9, 1.9 Hz, 2H), 3.18 (s, 9H). $^{13}$C NMR (101 MHz, dmso) δ 196.61, 135.71, 133.68, 132.51, 130.69, 129.92, 129.36, 128.80, 128.23, 127.63, 123.88, 61.38, 53.07, 32.71. LC-MS (ESI-TOF): m/z 242.20 (C$_{16}$H$_{20}$NO$^+$ calcd 242.15).

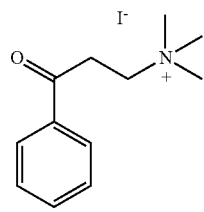

24: Obtained in 76% yield as white solid. $^1$H NMR (400 MHz, DMSO-d$_6$) δ 8.11-8.04 (m, 2H), 7.74-7.67 (m, 1H), 7.62-7.54 (m, 2H), 3.71 (s, 4H), 3.15 (s, 9H). $^{13}$C NMR (101 MHz, dmso) δ 196.69, 136.35, 134.21, 129.18, 128.57, 61.28, 53.06, 53.03, 52.99, 32.65. LC-MS (ESI-TOF): m/z 192.30 (C$_{12}$H$_{18}$NO$^+$ calcd 192.14).

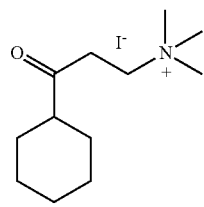

25: Obtained in 30% yield as yellowish solid. $^1$H NMR (400 MHz, DMSO-d$_6$) δ 3.49 (dd, J=8.3, 6.9 Hz, 2H), 3.16-3.07 (m, 4H), 3.04 (s, 9H), 2.43 (dd, J=7.1, 3.6 Hz, 1H), 1.91-1.67 (m, 4H), 1.68-1.57 (m, 1H), 1.32-1.10 (m, 5H). $^{13}$C NMR (101 MHz, dmso) δ 210.13, 60.86 (t, J=3 Hz), 54.83 (t, J=4 Hz), 52.84 (t, J=4 Hz), 50.22, 33.92, 28.18, 25.82, 25.46. LC-MS (ESI-TOF): m/z 198.00 (C$_{12}$H$_{24}$NO$^+$ calcd 198.19).

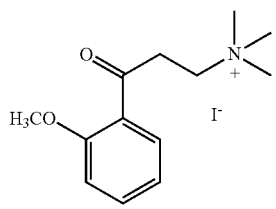

26: Obtained in 50% yield as Yellowish solid. $^1$H NMR (400 MHz, DMSO-d$_6$) δ 7.66 (dd, J=7.7, 1.8 Hz, 1H), 7.60 (ddd, J=8.4, 7.3, 1.8 Hz, 1H), 7.23 (dd, J=8.5, 0.9 Hz, 1H), 7.07 (td, J=7.5, 1.0 Hz, 1H), 3.93 (s, 3H), 3.68 (dd, J=8.3, 6.6 Hz, 2H), 3.51 (t, J=7.2 Hz, 2H), 3.11 (s, 13H). $^{13}$C NMR (101 MHz, dmso) δ 197.77, 158.94, 134.92, 130.15, 127.10, 120.93, 113.07, 61.23 (t, J=3 Hz), 56.42, 54.85 (t, J=4 Hz), 52.98 (t, J=4 Hz), 37.09. LC-MS (ESI-TOF): m/z 222.30 (C$_{13}$H$_{20}$NO$_2^+$ calcd 222.15).

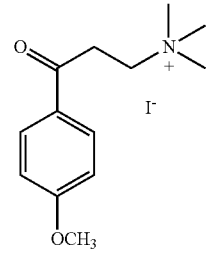

27: Obtained in 64% yield as off white solid. $^1$H NMR (400 MHz, DMSO-d$_6$) δ 8.05 (d, J=8.9 Hz, 2H), 7.09 (d, J=8.9 Hz, 2H), 3.87 (s, 3H), 3.76-3.58 (m, 4H), 3.14 (s, 7H), 3.12-3.09 (m, 2H). $^{13}$C NMR (101 MHz, dmso) δ 195.00, 164.00, 130.96, 130.94, 129.34, 114.37, 114.32, 61.45, 56.13, 54.85 (t, J=4 Hz), 53.02 (t, J=4 Hz), 32.20. LC-MS (ESI-TOF): m/z 222.30 (C$_{13}$H$_{20}$NO$_2^+$ calcd 222.15).

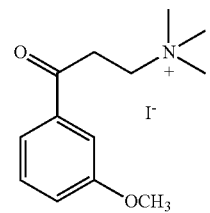

28: Obtained in 56% yield as off white solid. $^1$H NMR (400 MHz, DMSO-d$_6$) δ 7.67 (ddd, J=7.7, 1.6, 1.0 Hz, 1H), 7.56 (dd, J=2.7, 1.5 Hz, 1H), 7.50 (dd, J=8.2, 7.7 Hz, 1H), 7.28 (ddd, J=8.2, 2.7, 0.9 Hz, 1H), 3.85 (s, 3H), 3.69 (s, 4H), 3.14 (s, 7H), 3.11 (s, 3H). $^{13}$C NMR (101 MHz, dmso) δ 196.51, 159.89, 137.74, 130.38, 121.01, 119.91, 113.50, 61.32, 55.97, 54.85 (t, J=4 Hz), 53.04 (t, J=4 Hz), 32.79. LC-MS (ESI-TOF): m/z 222.30 (C$_{13}$H$_{20}$NO$_2^+$ calcd 222.15).

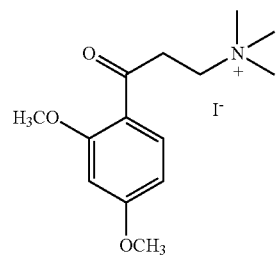

29: Obtained in 74% yield as baby pink solid. $^1$H NMR (400 MHz, DMSO-d6) δ 7.74 (d, J=8.7 Hz, 1H), 6.70 (d, J=2.3 Hz, 1H), 6.68-6.60 (m, 1H), 3.95 (s, 3H), 3.86 (s, 3H), 3.65 (dd, J=8.5, 6.8 Hz, 2H), 3.44 (t, J=7.5 Hz, 2H), 3.11 (d, J=0.9 Hz, 11H). $^{13}$C NMR (101 MHz, dmso) δ 195.02, 165.26, 161.52, 132.55, 119.54, 106.63, 98.92, 61.49, 56.50, 56.21, 54.81 (t, J=4 Hz), 52.95 (t, J=4 Hz), 36.88. LC-MS (ESI-TOF): m/z 252.30 (C$_{14}$H$_{22}$NO$_3^+$ calcd 252.16).

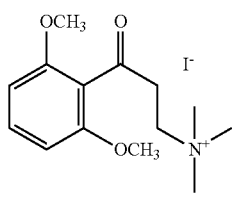 [SMILES: COc1cccc(OC)c1C(=O)CC[N+](C)(C)C ; [I-]]

30: Obtained in 61% yield as off white solid. $^1$H NMR (400 MHz, DMSO-d$_6$) δ 7.40 (t, J=8.4 Hz, 1H), 6.76 (d, J=8.4 Hz, 2H), 3.78 (s, 6H), 3.68 (t, J=7.5 Hz, 2H), 3.27 (t, J=7.4 Hz, 2H), 3.09 (s, 9H). $^{13}$C NMR (101 MHz, dmso) δ 200.28, 156.68, 132.05, 119.06, 104.91, 60.29, 56.46, 54.85 (t, J=4 Hz), 52.80, 38.03. LC-MS (ESI-TOF): m/z 252.20 (C$_{14}$H$_{22}$NO$_3^+$ calcd 252.16).

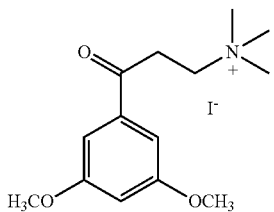

31: Obtained in 58% yield as off white solid. $^1$H NMR (400 MHz, DMSO-d$_6$) δ 7.19 (d, J=2.3 Hz, 2H), 6.83 (t, J=2.3 Hz, 1H), 3.83 (s, 6H), 3.67 (d, J=1.1 Hz, 4H), 3.15 (s, 9H). $^{13}$C NMR (101 MHz, dmso) δ 196.37, 161.07, 138.30, 106.50, 105.73, 61.26, 56.14, 54.82 (t, J=4 Hz), 53.02, 32.86. LC-MS (ESI-TOF): m/z 252.30 (C$_{14}$H$_{22}$NO$_3^+$ calcd 252.16).

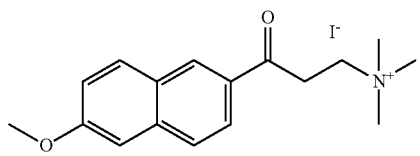

32: Obtained in 33% yield as off white solid. $^1$H NMR (400 MHz, DMSO-d$_6$) δ 8.75 (d, J=1.7 Hz, 1H), 8.10-7.99 (m, 2H), 7.95 (d, J=8.7 Hz, 1H), 7.45 (d, J=2.6 Hz, 1H), 7.31 (dd, J=9.0, 2.5 Hz, 1H), 3.93 (s, 3H), 3.87-3.67 (m, 4H), 3.19 (s, 9H). $^{13}$C NMR (101 MHz, dmso) δ 196.19, 160.01, 137.63, 131.63, 131.60, 130.64, 127.77, 127.53, 124.56, 120.21, 106.62, 61.48, 55.95, 54.86 (t, J=3 Hz), 53.09, 32.55. LC-MS (ESI-TOF): m/z 272.20 (C$_{17}$H$_{22}$NO$_2^+$ calcd 272.16).

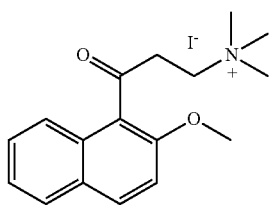

33: Obtained in 57% yield as off white solid. $^1$H NMR (400 MHz, DMSO-d$_6$) δ 8.17-8.07 (m, 1H), 8.01-7.91 (m, 1H), 7.63 (dq, J=8.6, 0.9 Hz, 1H), 7.59 (d, J=9.2 Hz, 1H), 7.54 (ddd, J=8.5, 6.8, 1.4 Hz, 1H), 7.43 (ddd, J=8.1, 6.8, 1.2 Hz, 1H), 4.01 (s, 3H), 3.81 (dd, J=8.3, 6.9 Hz, 2H), 3.50 (t, J=7.5 Hz, 2H), 3.12 (d, J=9.7 Hz, 9H). $^{13}$C NMR (101 MHz, dmso) δ 203.04, 154.61, 132.66, 130.03, 128.78, 128.71, 128.25, 124.63, 123.52, 123.36, 114.02, 60.71, 57.12, 54.85 (t, J=4 Hz), 52.90, 38.36. LC-MS (ESI-TOF): m/z 272.30 (C$_{17}$H$_{22}$NO$_2^+$ calcd 272.16).

Synthesis of Hydroxyl α-NETA Derivatives 34

Scheme S1

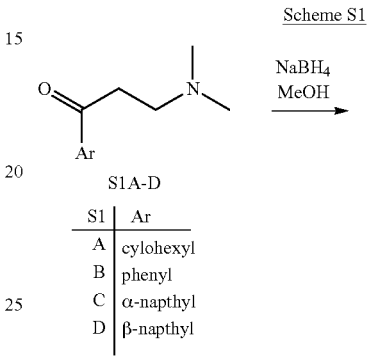

| S1 | Ar |
|---|---|
| A | cylohexyl |
| B | phenyl |
| C | α-napthyl |
| D | β-napthyl |

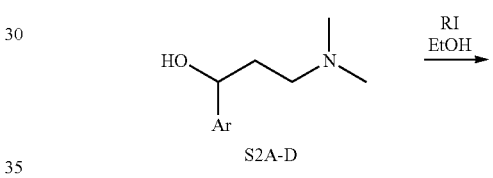

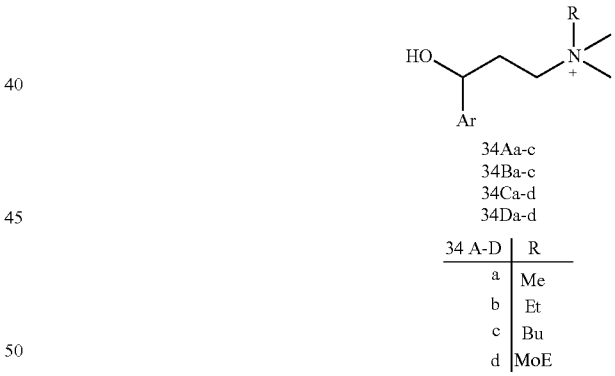

| 34 A-D | R |
|---|---|
| a | Me |
| b | Et |
| c | Bu |
| d | MoE |

Synthesis of S2A-D: Under a nitrogen atmosphere, the keto amine S1 (1.0 eq, 8.9 mmol) was taken in methanol (15 mL) in a two-neck round-bottom flask. The mixture was cooled to 0-5° C. and then NaBH$_4$ (1.3 eq, 1.15 mmol) was added in small portions over 10 min. The reaction mixture was stirred for 3 h at 0-5° C. and the progress of reaction was monitored by TLC. After completion the reaction was quenched with water (2.0 mL). The solvent volume then reduced to 10% on rotary evaporator. The crude obtained was taken into ethyl acetate (150 mL) and then washed with water (50 mL) followed by brine solution (50 mL). The organic layer was dried over Na$_2$SO$_4$, filtered and evaporated to dryness to afford the desired compound S2 as waxy solid.

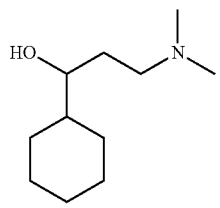

S2A: Obtained in 86% yield as colorless oil. $^1$H NMR (400 MHz, Chloroform-d) δ 3.49 (ddd, J=9.8, 6.4, 2.5 Hz, 1H), 2.62 (ddd, J=12.4, 11.3, 3.4 Hz, 1H), 2.44 (ddd, J=12.4, 4.3, 3.4 Hz, 1H), 2.24 (s, 6H), 1.98-1.87 (m, 1H), 1.80-1.61 (m, 4H), 1.61-1.43 (m, 2H), 1.37-1.07 (m, 4H), 1.07-0.91 (m, 2H). $^{13}$C NMR (101 MHz, cdcl$_3$) δ 78.31, 59.40, 45.25, 44.10, 29.11, 28.79, 28.58, 26.64, 26.31, 26.21. LC-MS (ESI-TOF): m/z 186.40 ([C$_{11}$H$_{23}$NO+H]$^+$ calcd 186.18).

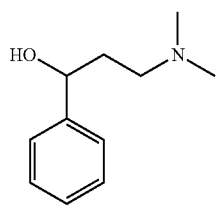

S2B: Obtained in 82% yield as light yellow oil. 1H NMR (400 MHz, Chloroform-d) δ 7.41-7.30 (m, 4H), 7.27-7.20 (m, 1H), 4.93 (dd, J=7.7, 3.9 Hz, 1H), 2.65 (ddd, J=12.9, 8.9, 4.2 Hz, 1H), 2.51-2.43 (m, 1H), 2.30 (s, 6H), 1.89-1.74 (m, 2H). $^{13}$C NMR (101 MHz, cdcl$_3$) δ 145.09, 128.14, 126.81, 125.53, 75.75, 58.42, 45.30, 34.51. LC-MS (ESI-TOF): m/z 180.30 ([C$_{11}$H$_{17}$NO+H]$^+$ calcd 180.13).

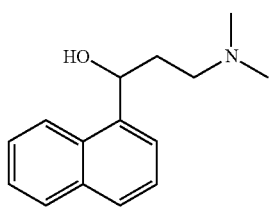 [SMILES: CN(C)CCC(O)c1cccc2ccccc12]

S2C: Obtained in 91% yield as light brown semisolid. $^1$H NMR (400 MHz, Chloroform-d) δ 8.05-7.97 (m, 1H), 7.90-7.82 (m, 1H), 7.76 (tt, J=7.9, 0.9 Hz, 2H), 7.55-7.39 (m, 3H), 5.71 (dd, J=8.1, 3.1 Hz, 1H), 2.69 (ddd, J=12.7, 9.6, 3.2 Hz, 1H), 2.50 (ddd, J=12.5, 6.4, 3.2 Hz, 1H), 2.34 (s, 6H), 2.14-2.01 (m, 1H), 1.98-1.85 (m, 1H). $^{13}$C NMR (101 MHz, cdcl$_3$) δ 140.38, 133.73, 130.14, 128.86, 127.31, 125.65, 125.52, 125.17, 122.98, 122.96, 72.56, 58.49, 45.36, 33.28. LC-MS (ESI-TOF): m/z 230.30 ([C$_{15}$H$_{19}$NO+H]$^+$ calcd 230.15).

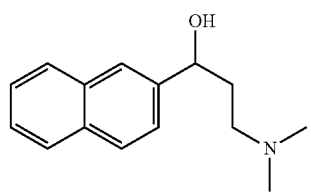 [SMILES: CN(C)CCC(O)c1ccc2ccccc2c1]

S2D: Obtained in 93% yield as off white solid. $^1$H NMR (400 MHz, Chloroform-d) δ 7.92-7.73 (m, 4H), 7.51-7.38 (m, 3H), 5.16-5.02 (m, 1H), 2.66 (ddd, J=12.8, 9.2, 3.8 Hz, 1H), 2.52-2.43 (m, 1H), 2.30 (s, 6H), 1.98-1.79 (m, 2H). $^{13}$C NMR (101 MHz, cdcl$_3$) δ 142.56, 133.39, 132.69, 127.94, 127.81, 127.59, 125.87, 125.41, 124.16, 123.97, 75.80, 58.39, 45.33, 34.41. LC-MS (ESI-TOF): m/z 230.30 ([C$_{15}$H$_{19}$NO+H]$^+$ calcd 230.15).

Synthesis of 34A-D

The tertiary amine S2 (1.0 eq, 0.8 mmol) was suspended in ethanol (5 mL) in a 14 mL glass vial followed by dropwise addition of alkyl iodide (1.5 eq, 1.26 mmol) at room temperature and the reaction mixture was stirred for 16-18 h, during which time the a white solid precipitated. The solvent was removed using nitrogen flow to afford semi-solid, which was taken in diethyl ether (~25 mL) and stirred for 30 min to obtain free-flow solid. The solid was collected by filtration and washed with copious amounts of diethyl ether and dried in a high vacuum to afford the desired compound as off white solid. For the reaction where butyl iodide was a reactant, similar procedure was followed except the reaction was carried out in seal tube at 65° C. for 24 h.

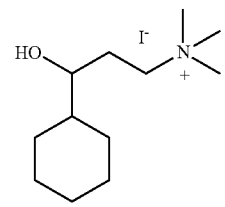

34Aa: Obtained in 60% yield as off white solid. $^1$H NMR (400 MHz, DMSO-d$_6$) δ 4.66 (d, J=5.7 Hz, 1H), 3.43 (td, J=12.4, 5.0 Hz, 1H), 3.37-3.26 (m, 2H), 3.21 (dp, J=8.7, 2.8 Hz, 1H), 3.06 (s, 9H), 1.85-1.57 (m, 7H), 1.30-0.90 (m, 6H). $^{13}$C NMR (101 MHz, dmso) δ 72.12, 64.52, 52.68, 52.64, 52.60, 43.95, 28.99, 28.16, 27.30, 26.56, 26.27, 26.16. LC-MS (ESI-TOF): m/z 200.30 (C$_{12}$H$_{26}$NO$^+$ calcd 200.20).

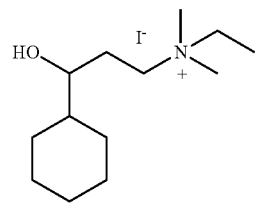

34Ab: Obtained in 87% yield as colorless semisolid. $^1$H NMR (400 MHz, DMSO-d$_6$) δ 4.66 (d, J=5.8 Hz, 1H), 3.40-3.32 (m, 2H), 3.32-3.13 (m, 3H), 2.98 (s, 6H), 1.89-1.67 (m, 4H), 1.67-1.52 (m, 3H), 1.35-0.87 (m, 9H). $^{13}$C NMR (101 MHz, dmso) δ 72.12, 61.46, 58.74, 50.01, 43.96, 29.00, 28.17, 26.89, 26.56, 26.26, 26.15, 8.23. LC-MS (ESI-TOF): m/z 214.40 (C$_{13}$H$_{28}$NO$^+$ calcd 214.22).

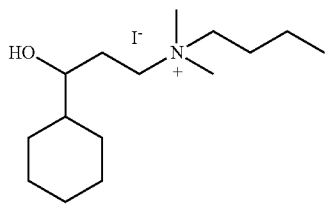

34Ac: Obtained in 81% yield as colorless semisolid. ¹H NMR (400 MHz, DMSO-d₆) δ 4.64 (d, J=5.8 Hz, 1H), 3.44-3.16 (m, 5H), 3.01 (s, 6H), 1.85-1.68 (m, 4H), 1.68-1.50 (m, 5H), 1.31 (q, J=7.3 Hz, 2H), 1.27-0.97 (m, 6H), 0.93 (t, J=7.3 Hz, 3H). ¹³C NMR (101 MHz, dmso) δ 72.13, 63.01, 62.07, 50.55, 43.91, 29.03, 28.16, 26.95, 26.56, 26.26, 26.15, 24.12, 19.61, 13.96. LC-MS (ESI-TOF): m/z 242.00 ($C_{15}H_{32}NO^+$ calcd 242.25).

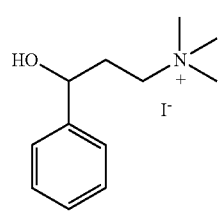

34Ba: Obtained in 63% yield as white solid. ¹H NMR (400 MHz, DMSO-d₆) b 7.45-7.32 (m, 4H), 7.32-7.22 (m, 1H), 5.58 (dd, J=4.4, 0.6 Hz, 1H), 4.63 (dt, J=8.5, 4.4 Hz, 1H), 3.52-3.33 (m, 2H), 3.06 (s, 9H), 2.09-1.93 (m, 2H). ¹³C NMR (101 MHz, dmso) δ 145.39, 128.62, 127.60, 126.11, 70.11, 63.96, 52.76, 52.72, 52.68, 32.45. LC-MS (ESI-TOF): m/z 194.30 ($C_{12}H_{20}NO^+$ calcd 194.15).

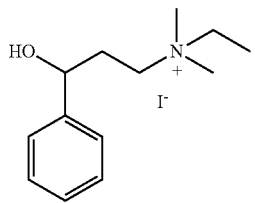

34Bb: Obtained in 54% yield as colorless semisolid. ¹H NMR (400 MHz, DMSO-d₆) δ 7.49-7.31 (m, 4H), 7.31-7.23 (m, 1H), 5.57 (d, J=4.4 Hz, 1H), 4.64 (dt, J=8.4, 4.4 Hz, 1H), 3.44-3.25 (m, 4H), 2.99 (s, 6H), 2.08-1.87 (m, 2H), 1.29-1.13 (m, 3H). ¹³C NMR (101 MHz, dmso) δ 145.38, 128.60, 127.59, 126.11, 70.04, 60.81, 58.80, 50.12, 50.08, 32.04, 8.22. LC-MS (ESI-TOF): m/z 208.30 ($C_{13}H_{22}NO^+$ calcd 208.17).

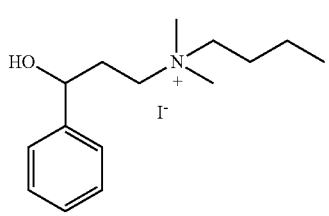

34Bc: Obtained in 75% yield as colorless semisolid. ¹H NMR (400 MHz, DMSO-d₆) δ 7.47-7.30 (m, 4H), 7.31-7.23 (m, 1H), 5.57 (d, J=4.4 Hz, 1H), 4.63 (dt, J=8.5, 4.5 Hz, 1H), 3.43-3.33 (m, 2H), 3.29-3.18 (m, 2H), 3.01 (s, 6H), 1.99 (ddt, J=14.0, 9.5, 5.7 Hz, 2H), 1.59 (p, J=7.6 Hz, 2H), 1.28 (h, J=7.4 Hz, 2H), 0.92 (t, J=7.3 Hz, 3H). ¹³C NMR (101 MHz, dmso) δ 145.35, 128.60, 127.59, 126.13, 70.04, 63.03, 61.38, 50.65, 32.06, 24.08, 19.58, 13.94. LC-MS (ESI-TOF): m/z 236.30 ($C_{15}H_{26}NO^+$ calcd 236.20).

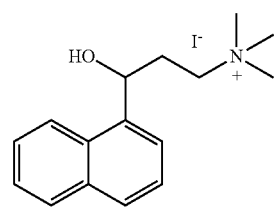

34Ca: Obtained in 86% yield as off white foamy solid. ¹H NMR (400 MHz, DMSO-d₆) δ 8.20 (d, J=8.4 Hz, 1H), 8.00-7.93 (m, 1H), 7.87 (d, J=8.3 Hz, 1H), 7.76-7.69 (m, 1H), 7.63-7.46 (m, 3H), 5.72 (dd, J=4.4, 0.8 Hz, 1H), 5.40 (dt, J=8.2, 3.7 Hz, 1H), 3.69 (td, J=12.3, 4.6 Hz, 1H), 3.58 (td, J=12.3, 5.0 Hz, 1H), 3.07 (s, 9H), 2.27-2.14 (m, 1H), 2.08 (tdd, J=12.9, 9.0, 4.9 Hz, 1H). ¹³C NMR (101 MHz, dmso) δ 140.59, 133.27, 129.62, 128.68, 127.50, 126.09, 125.52, 125.39, 123.11, 122.88, 66.50, 63.72, 52.23, 31.46. LC-MS (ESI-TOF): m/z 244.30 ($C_{16}H_{22}NO^+$ calcd 244.17).

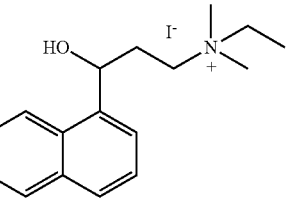

34Cb: Obtained in 83% yield as off white foam. ¹H NMR (400 MHz, DMSO-d₆) δ 8.19 (dt, J=8.5, 1.1 Hz, 1H), 8.00-7.93 (m, 1H), 7.86 (dt, J=8.2, 0.9 Hz, 1H), 7.72 (dt, J=7.0, 1.0 Hz, 1H), 7.62-7.48 (m, 3H), 5.73 (dd, J=4.4, 0.7 Hz, 1H), 5.40 (dt, J=8.1, 3.6 Hz, 1H), 3.62 (td, J=12.5, 4.7 Hz, 1H), 3.50 (td, J=12.4, 4.8 Hz, 1H), 3.33 (d, J=7.6 Hz, 2H), 2.99 (s, 6H), 2.14 (td, J=10.3, 8.6, 3.9 Hz, 1H), 2.04 (tdd, J=13.0, 9.1, 4.8 Hz, 1H), 1.23 (t, J=7.3 Hz, 3H). ¹³C NMR (101 MHz, dmso) δ 141.08, 133.75, 130.09, 129.17, 127.98, 126.55, 126.00, 125.86, 123.54, 123.34, 66.92, 61.05, 58.94, 50.14, 49.97, 31.56, 8.21. LC-MS (ESI-TOF): m/z 258.30 ($C_{17}H_{24}NO^+$ calcd 258.19).

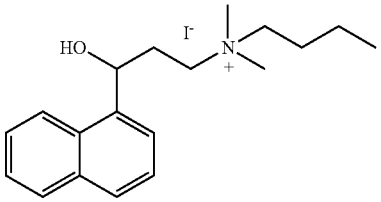

34Cc: Obtained in 60% yield as off white foam. ¹H NMR (400 MHz, DMSO-d₆) δ 8.26-8.16 (m, 1H), 7.97 (dd, J=7.9, 1.7 Hz, 1H), 7.87 (d, J=8.3 Hz, 1H), 7.77-7.69 (m, 1H), 7.63-7.47 (m, 4H), 5.72 (s, 1H), 5.41 (dt, J=8.1, 3.7 Hz, 1H), 3.64 (td, J=12.4, 4.6 Hz, 1H), 3.50 (td, J=12.5, 4.7 Hz, 1H), 3.30-3.17 (m, 2H), 3.01 (d, J=2.2 Hz, 6H), 2.15 (ddt, J=12.8, 7.9, 3.9 Hz, 1H), 2.05 (tdd, J=13.2, 8.8, 4.7 Hz, 1H), 1.69-1.52 (m, 2H), 1.25 (h, J=7.3 Hz, 2H), 0.90 (t, J=7.3 Hz, 3H). $^{13}$C NMR (101 MHz, dmso) δ 141.00, 133.76, 130.08, 129.17, 127.98, 126.51, 126.01, 125.86, 123.57, 123.37, 66.97, 63.07, 61.47, 50.79, 50.61, 31.54, 24.11, 19.56, 13.93. LC-MS (ESI-TOF): m/z 286.30 ($C_{19}H_{28}NO^+$ calcd 286.22).

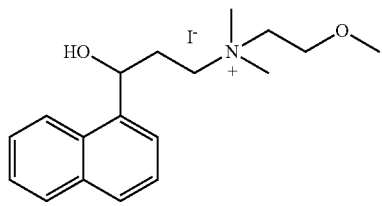

34Cd: Obtained in 65% yield as pale yellow semisolid. $^1$H NMR (400 MHz, DMSO-$d_6$) δ 8.22-8.14 (m, 1H), 7.99-7.94 (m, 1H), 7.86 (d, J=8.1 Hz, 1H), 7.72 (dt, J=7.0, 1.0 Hz, 1H), 7.61-7.49 (m, 3H), 5.72 (dd, J=4.4, 0.7 Hz, 1H), 5.39 (dt, J=8.3, 3.7 Hz, 1H), 3.80-3.49 (m, 6H), 3.28 (s, 3H), 3.08 (s, 3H), 3.06 (s, 3H), 2.19 (t, J=12.6 Hz, 1H), 2.08 (ddd, J=17.7, 12.5, 6.4 Hz, 1H). $^{13}$C NMR (101 MHz, dmso) δ 141.11, 133.74, 130.10, 129.14, 127.95, 126.50, 125.98, 125.85, 123.57, 123.36, 67.08, 65.80, 62.77, 58.55, 51.40, 40.23, 31.67. LC-MS (ESI-TOF): m/z 288.30 ($C_{18}H_{26}NO_2^+$ calcd 288.20).

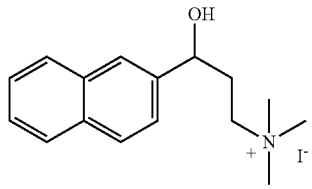

34 Da: Obtained in 66% yield as white solid. $^1$H NMR (400 MHz, DMSO-$d_6$) δ 7.97-7.85 (m, 4H), 7.57 (dd, J=8.5, 1.7 Hz, 1H), 7.55-7.46 (m, 2H), 5.73 (d, J=4.3 Hz, 1H), 4.82 (dt, J=8.3, 4.4 Hz, 1H), 3.45 (ddt, J=14.6, 11.3, 7.0 Hz, 2H), 3.07 (s, 9H), 2.24-2.01 (m, 2H). $^{13}$C NMR (101 MHz, dmso) δ 142.80, 133.22, 132.83, 128.26, 128.18, 127.96, 126.61, 126.19, 124.74, 124.43, 70.17, 63.83, 52.73, 32.23. LC-MS (ESI-TOF): m/z 244.30 ($C_{16}H_{22}NO^+$ calcd 244.17).

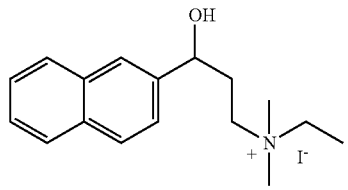

34db: Obtained in 83% yield as yellow semisolid. $^1$H NMR (400 MHz, DMSO-$d_6$) δ 8.01-7.83 (m, 4H), 7.57 (dd, J=8.5, 1.7 Hz, 1H), 7.55-7.44 (m, 2H), 5.73 (d, J=4.4 Hz, 1H), 4.82 (dt, J=8.4, 4.3 Hz, 1H), 3.46-3.32 (m, 4H), 2.99 (s, 6H), 2.18-1.97 (m, 2H), 1.21 (t, J=7.3 Hz, 3H). $^{13}$C NMR (101 MHz, dmso) δ 142.79, 133.21, 132.82, 128.25, 128.18, 127.97, 126.61, 126.19, 124.74, 124.43, 70.12, 60.73, 58.76, 50.14, 31.81, 8.22. LC-MS (ESI-TOF): m/z 258.30 ($C_{17}H_{24}NO^+$ calcd 258.19).

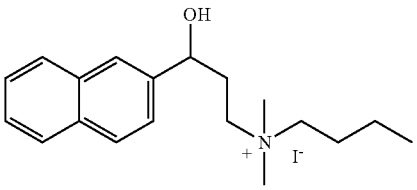

34Dc: Obtained in 89% yield as colorless glassy material. $^1$H NMR (400 MHz, DMSO-$d_6$) δ 7.96-7.85 (m, 4H), 7.57 (dd, J=8.5, 1.7 Hz, 1H), 7.55-7.46 (m, 2H), 5.73 (d, J=4.3 Hz, 1H), 4.82 (dt, J=8.4, 4.3 Hz, 1H), 3.47-3.35 (m, 2H), 3.30-3.19 (m, 2H), 3.01 (s, 6H), 2.10 (dh, J=13.0, 7.1 Hz, 2H), 1.67-1.51 (m, 2H), 1.28 (h, J=7.4 Hz, 2H), 0.90 (t, J=7.3 Hz, 3H). $^{13}$C NMR (101 MHz, dmso) δ 142.74, 133.21, 132.83, 128.25, 128.18, 127.97, 126.62, 126.20, 124.74, 124.46, 70.12, 62.99, 61.27, 50.67, 31.82, 24.09, 19.58, 13.92. LC-MS (ESI-TOF): m/z 286.30 ($C_{19}H_{28}NO^+$ calcd 286.22).

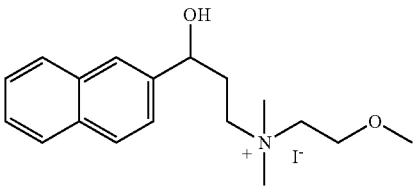

34Dd: Obtained in 68% yield as pale yellow semisolid. $^1$H NMR (400 MHz, DMSO-$d_6$) δ 7.98-7.84 (m, 4H), 7.56 (dd, J=8.5, 1.7 Hz, 1H), 7.55-7.44 (m, 2H), 5.73 (d, J=4.3 Hz, 1H), 4.81 (dt, J=8.4, 4.4 Hz, 1H), 3.72 (s, 2H), 3.62-3.42 (m, 4H), 3.26 (s, 3H), 3.07 (s, 3H), 3.07 (s, 3H), 2.22-2.03 (m, 2H). $^{13}$C NMR (101 MHz, dmso) δ 142.83, 133.21, 132.82, 128.23, 128.17, 127.96, 126.60, 126.18, 124.76, 124.43, 70.26, 65.82, 62.66, 62.53, 58.53, 51.35, 31.96. LC-MS (ESI-TOF): m/z 288.30 ($C_{18}H_{26}NO_2^+$ calcd 288.20).

Synthesis of Sulfone Derivative 35

Synthesis of S4: To a stirred solution of phenyl vinyl sulfone S3 (0.977 g, 5.81 mmol) in ethanol (10 mL) at room temperature, was added a 2M solution of dimethyl amine in methanol (0.739 g, 8.2 mL, 16.4 mmol) over 10 min. The mixture was stirred at room temperature for 30 min. The reaction was monitored by TLC. After completion the reaction mixture was concentrated under vacuum to dryness to afford desired product S4 as colorless oil (1.2 g, 97%). $^1$H NMR (400 MHz, Chloroform-d) δ 7.95-7.88 (m, 2H), 7.70-7.62 (m, 1H), 7.61-7.53 (m, 2H), 3.33-3.19 (m, 2H), 2.77-2.64 (m, 2H), 2.17 (s, 6H). $^{13}$C NMR (101 MHz, cdcl$_3$) δ 133.70, 129.22, 127.99, 109.99, 54.02, 52.22, 44.99. LC-MS (ESI-TOF): m/z 214.20 ([$C_{10}H_{15}NO_2S+H$]$^+$ calcd 214.08).

Scheme S2

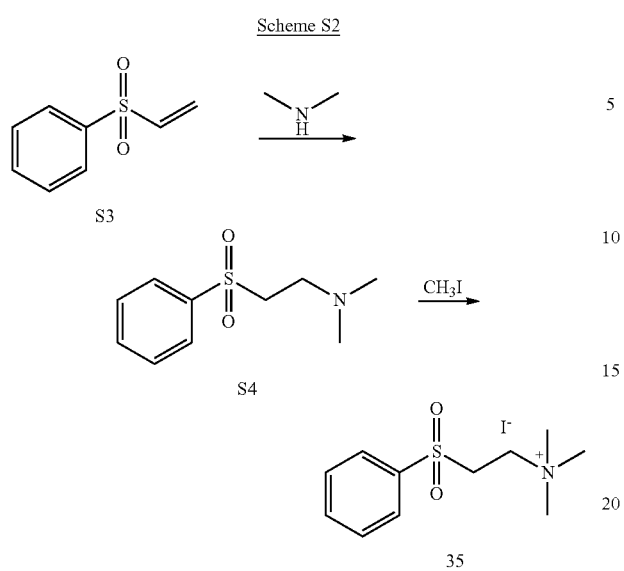

Synthesis of 35: To a stirred solution of N,N-dimethyl-2-(phenylsulfonyl)ethan-1-amine S4 (0.34 g, 1.6 mmol) in ethanol (5 mL) at room temperature, was added methyl iodide (0.34 g, 2.4 mmol) and reaction mixture was stirred for 18 h. The solvent was removed using nitrogen flow to afford semisolid, which was taken in diethyl ether (25 mL) and stirred for 30 min. The solid was collected by filtration and washed with copious amounts of diethyl ether and dried in a high vacuum to afford the desired compound 35 as off white solid (0.45 g, 79%). $^1$H NMR (400 MHz, DMSO-$d_6$) δ 8.00-7.90 (m, 2H), 7.87-7.78 (m, 1H), 7.76-7.66 (m, 2H), 4.12-3.96 (m, 2H), 3.74-3.60 (m, 2H), 3.07 (s, 9H). $^{13}$C NMR (101 MHz, dmso) δ 138.80, 135.04, 130.20, 128.24, 58.26, 52.98, 48.94. LC-MS (ESI-TOF): m/z 228.20 ($C_{11}H_{18}NO_2S^+$ calcd 228.11).

Synthesis of Elongated Linker Chain Length
α-NETA Analogues 36A-B

Scheme S3

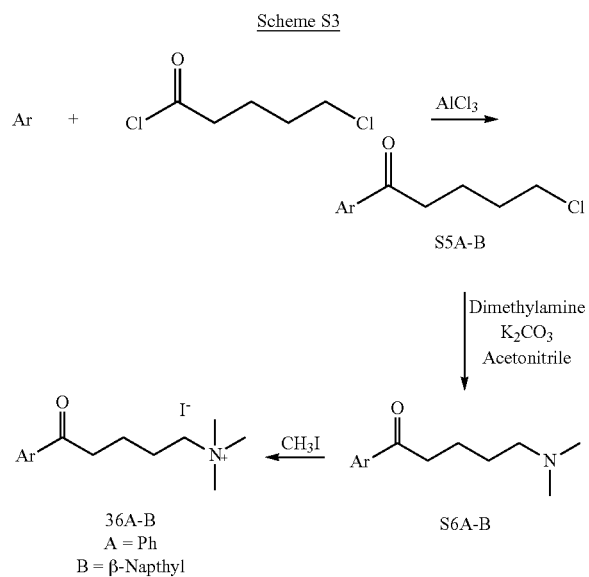

36A-B
A = Ph
B = β-Napthyl

Synthesis of S5A-B: Under a nitrogen atmosphere, $AlCl_3$ (1.1 eq, 43.0 mmol) was taken in dichloromethane (25 mL) in a single-neck round-bottom flask. The mixture was cooled to 0-5° C. and then 5-chloropentanoyl chloride (1.0 eq, 39.0 mmol) was added dropwise while keeping the reaction temperature below 5° C. To the reaction mixture a solution of either benzene or naphthalene in dichloromethane (25 mL) was then added dropwise over 30 min, giving yellow solution. The reaction mixture was then stirred for 2 h at room temperature and poured on crushed ice. Stirring was continued for 30 min then organic layer was separated. Aqueous layer was extracted again with dichloromethane (50 mL). Combined organic layer was washed with water, brine, dried over $Na_2SO_4$, filtered and evaporated to dryness to afford the crude compound that was further purified on silica gel column with 0-40% DCM in hexane as the eluent to obtain desired product S5 as an off white solid.

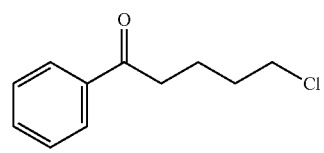 [SMILES: O=C(CCCCCl)c1ccccc1]

S5A: Obtained in 83% yield as off white solid. $^1$H NMR (400 MHz, Chloroform-d) δ 8.00-7.90 (m, 2H), 7.61-7.52 (m, 1H), 7.50-7.40 (m, 2H), 3.62-3.53 (m, 2H), 3.01 (t, J=6.9 Hz, 2H), 1.97-1.81 (m, 4H). $^{13}$C NMR (101 MHz, cdcl$_3$) δ 199.56, 136.83, 133.05, 128.60, 127.98, 127.97, 44.70, 37.53, 32.04, 21.49.

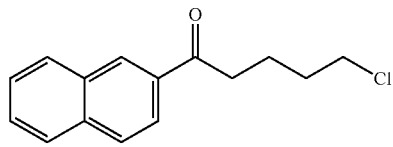 [SMILES: O=C(CCCCCl)c1ccc2ccccc2c1]

S5B: Obtained in 42% yield as pale yellow solid. $^1$H NMR (400 MHz, Chloroform-d) δ 8.59 (dd, J=8.6, 0.8 Hz, 1H), 8.01-7.94 (m, 1H), 7.91-7.81 (m, 2H), 7.63-7.44 (m, 3H), 3.59 (t, J=6.2 Hz, 2H), 3.08 (t, J=6.9 Hz, 2H), 2.01-1.84 (m, 4H). $^{13}$C NMR (101 MHz, cdcl$_3$) δ 203.91, 135.93, 133.97, 132.58, 130.10, 128.45, 127.91, 127.37, 126.47, 125.71, 124.37, 44.72, 41.09, 32.06, 21.95. LC-MS (ESI-TOF): m/z 247.10 ($[C_{15}H_{15}ClO+H]^+$ calcd 247.08).

Synthesis of S6A-B

In a two-neck round-bottom flask, fitted with a reflux condenser was suspended S5 (1 eq, 10.2 mmol) in acetonitrile (50 mL). Then dimethyl amine HCl salt (1.2 eq, 12.2 mmol) and $K_2CO_3$ (2.4 eq, 25 mmol) were added. The reaction mixture was stirred at refluxed for 24 h. The reaction was monitored by TLC for the absence of the starting material. After cooling to ambient temperature, it was poured into ice-cold water (~150 mL) and stirred for 10 min then extracted with dichloromethane (2×100 mL). combined organic layer was washed with water, brine, dried over $Na_2SO_4$ and filtered. The organic layer was evaporated to dryness and the residue was purified by column chromatography by using 0-5% Methanol in dichloromethane to afford the desired compound S6 as a brown oil.

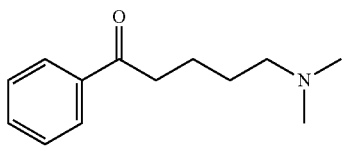

S6A: Obtained in 86% yield as brown oil. $^1$H NMR (400 MHz, Chloroform-d) δ 7.96-7.88 (m, 2H), 7.54-7.47 (m, 1H), 7.46-7.37 (m, 2H), 3.01-2.89 (m, 2H), 2.28 (s, 2H), 2.18 (s, 6H), 1.73 (ddt, J=8.5, 7.8, 7.1 Hz, 2H), 1.58-1.45 (m, 2H). $^{13}$C NMR (101 MHz, cdcl$_3$) δ 200.09, 136.99, 132.83, 128.49, 127.98, 59.52, 45.49, 38.35, 27.39, 22.16. LC-MS (ESI-TOF): m/z 206.30 ($[C_{13}H_{19}NO+H]^+$ calcd 206.15).

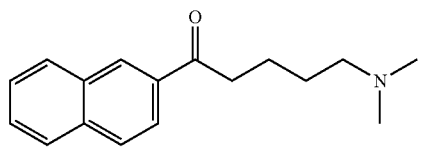 [SMILES: CN(C)CCCCC(=O)c1ccc2ccccc2c1]

S6B: Obtained in 78% yield as brown semisolid. $^1$H NMR (400 MHz, Chloroform-d) δ 8.59-8.48 (m, 1H), 7.96 (dt, J=7.9, 1.0 Hz, 1H), 7.89-7.78 (m, 2H), 7.63-7.41 (m, 3H), 3.07 (t, J=7.3 Hz, 2H), 2.34-2.25 (m, 2H), 2.21 (s, 6H), 1.87-1.74 (m, 2H), 1.64-1.51 (m, 2H). $^{13}$C NMR (101 MHz, cdcl$_3$) δ 204.67, 136.31, 133.94, 132.31, 130.10, 128.37, 127.77, 127.16, 126.38, 125.74, 124.34, 59.57, 45.53, 42.05, 27.43, 22.60. LC-MS (ESI-TOF): m/z 256.30 ($[C_{17}H_{21}NO+H]^+$ calcd 256.16).

Synthesis of 36A-B

To a stirred solution of S6 (1.0 eq, 1.1 mmol) in ethanol (5 mL) at room temperature, was added methyl iodide (1.5 eq, 1.7 mmol) and stirred for 24 h, during which time the a white solid precipitated. The solid was collected by filtration and washed with copious amounts of ethanol followed by diethyl ether. The solid was further purified by stirring them in mixture of acetonitrile and diethyl ether for overnight.

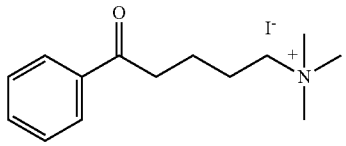

36A: Obtained in 80% yield as off white solid. $^1$H NMR (400 MHz, +/DMSO-d$_6$) δ 8.00-7.91 (m, 2H), 7.67-7.59 (m, 1H), 7.57-7.47 (m, 2H), 3.40-3.31 (m, 2H), 3.12 (t, J=7.0 Hz, 2H), 3.04 (s, 9H), 1.82-1.68 (m, 2H), 1.68-1.55 (m, 2H). $^{13}$C NMR (101 MHz, dmso) δ 199.82, 136.98, 133.66, 129.18, 128.31, 65.54, 52.65 (t, J=4 Hz), 37.59, 22.10, 20.77. LC-MS (ESI-TOF): m/z 220.30 ($C_{14}H_{22}NO^+$ calcd 220.17).

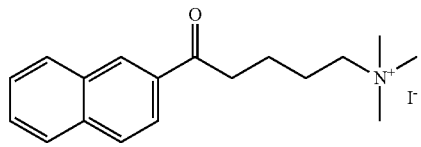 [SMILES: C[N+](C)(C)CCCCC(=O)c1ccc2ccccc2c1 ; [I-]]

36B: Obtained in 78% yield as off white solid. $^1$H NMR (400 MHz, DMSO-d$_6$) δ 8.51-8.42 (m, 1H), 8.15 (d, J=8.2 Hz, 1H), 8.12-8.06 (m, 1H), 8.06-7.98 (m, 1H), 7.69-7.50 (m, 3H), 3.43-3.33 (m, 2H), 3.22 (t, J=7.0 Hz, 2H), 3.07 (s, 9H), 1.81 (p, J=8.0, 7.5 Hz, 2H), 1.71 (p, J=7.1 Hz, 2H). $^{13}$C NMR (101 MHz, dmso) δ 204.17, 135.92, 133.93, 132.82, 129.78, 128.98, 128.35, 128.19, 126.87, 125.71, 125.29, 65.54, 52.65 (t, J=4 hz), 41.08, 22.09, 21.17. LC-MS (ESI-TOF): m/z 270.30 ($C_{18}H_{24}NO^+$ calcd 270.19).

Example 2

Improved Analogs of CMKLR1 Antagonist α-NETA Suppress Psoriasis

Chemerin and its receptors. Chemoattractants and their leukocyte-expressed G protein linked receptors (GPCRs) control the recruitment of circulating white blood cells, and direct their microenvironmental localization and cell-cell interactions within tissues. We and others identified chemerin as an endogenous chemoattractant ligand for chemokine-like receptor-1 (CMKLR1) in the human and mouse. Chemerin circulates in a pro-form that requires proteolytic processing by enzymes of the coagulation, fibrinolytic, and inflammatory cascades to unleash its chemotactic activity. CMKLR1 is expressed by macrophages, DC subsets, and NK cells, and these cells respond to chemerin with integrin activation, calcium signaling and chemotaxis. In experimental autoimmune encephalomyelitis (EAE), CMKLR1-deficient (CMKLR1 KO) mice develop less severe clinical and histological EAE associated with a reduction in macrophage infiltration of the CNS. Moreover, CMKLR1 helps direct the migration of dendritic cells to lymphoid organs and inflamed skin; and co-localization of CMKLR1-positive NK cells at tissue sites of inflammation supports a role for CMKLR1 and chemerin in recruiting NK cells as well.

Figure 9:
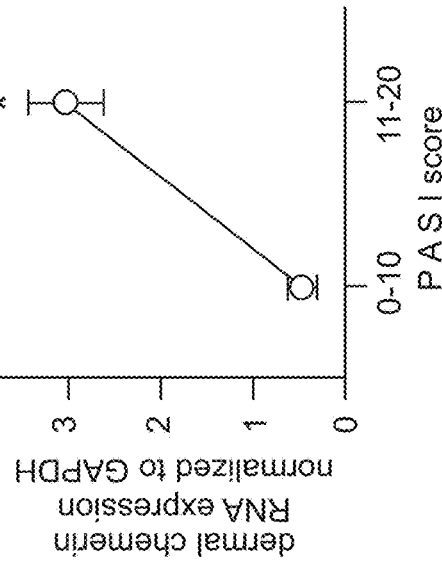
FIG. 9. Dermal chemerin RNA expression increased in patients with elevated PASI score. The dermal layer was mechanically separated from de-identified human skin specimens and chemerin RNA expression determined by RT-QPCR (normalized to GAPDH). 2-ΔCt values shown, mean±SEM, n=4 individual patient samples per PASI (total score, 0-72) bin. *p<0.05 by t-test. Patient demographics: 2 male, 6 female, ages 22-37.

Chemerin in human psoriasis. We sought to produce mechanistic insight into the biology of chemerin and its receptors in psoriasis. In healthy human skin we previously showed that chemerin is highly expressed by epidermal keratinocytes but negligibly by cells in the dermis. In contrast, we and others showed that in psoriatic human skin chemerin is redistributed with elevated levels in the dermis and lower levels in the epidermis. Chemerin co-localizes with vascular endothelial cells in human psoriatic skin. CMKLR1 is expressed on skin infiltrating leukocytes in human psoriasis lesions. Furthermore, plasma chemerin levels are significantly elevated in psoriasis patients. We showed that human psoriatic skin-derived chemerin stimulates CMKLR1+ cell migration, indicating that chemerin is activated locally in the skin. Furthermore, patients with elevated psoriasis area and severity index (PASI) total score expressed significantly higher levels of dermal chemerin RNA, implicating chemerin in human psoriasis disease progression (FIG. 9). These translationally-relevant studies imply a role for chemerin and its receptors in human psoriasis.

CMKLR1 antagonist α-NETA. We screened a 140,000-compound containing library for novel CMKLR1 inhibitors and identified 2-(α-naphthoyl) ethyltrimethylammonium iodide (α-NETA) as a CMKLR1 antagonist that inhibits chemerin-triggered CMKLR1+ cell migration. α-NETA significantly delayed the onset of experimental autoimmune encephalomyelitis (EAE) induced in WT mice by both active immunization with myelin oligodendrocyte glycoprotein peptide 35-55 and by adoptive transfer of encephalitogenic T cells. In addition, α-NETA treatment significantly reduced mononuclear cell infiltrates within the CNS. U.S. Pat. No. 9,265,738 includes the structure of α-NETA and additional information on its properties in preventing EAE.

Mouse psoriasis models. Mouse models have proven instrumental in identifying important pathomechanisms of psoriasis and have led to the identification of novel therapeutic targets, such as STAT3, TIMP-3, and Raf1. We selected the imiquimod (IMQ, TLR7 agonist) model for our preliminary studies based on its abundant desirable features (epidermal and vascular changes, T cell/neutrophil infiltration, involves IL-17 and other psoriasis-like gene signatures, and responds to anti-psoriatic drugs), and its compatibility with our existing chemerin/receptor deficient mice without the need for complicated genetic backcrossing. Mouse models will enable us to move beyond correlative/association studies and probe the mechanisms by which chemerin and its receptors contribute to the pathogenesis of psoriasis, and we use a highly validated IMQ-induced preclinical mouse model of psoriasis for this purpose.

Figure 10A:
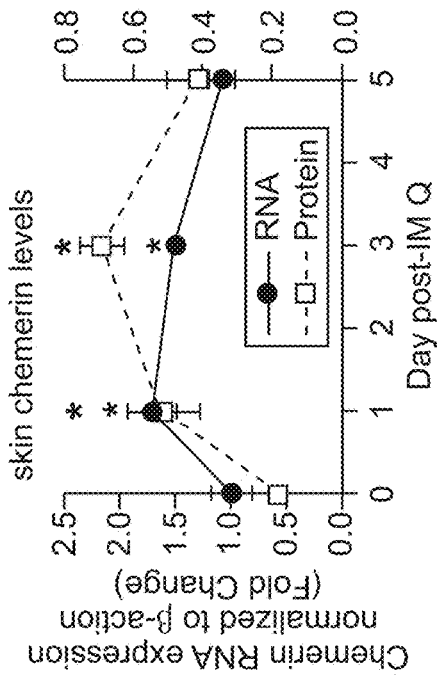
FIG. 10A-10E. Characterization of chemerin skin expression and CMKLR1+NK cells and monocytes in the IMQ model.
Figure 10B:
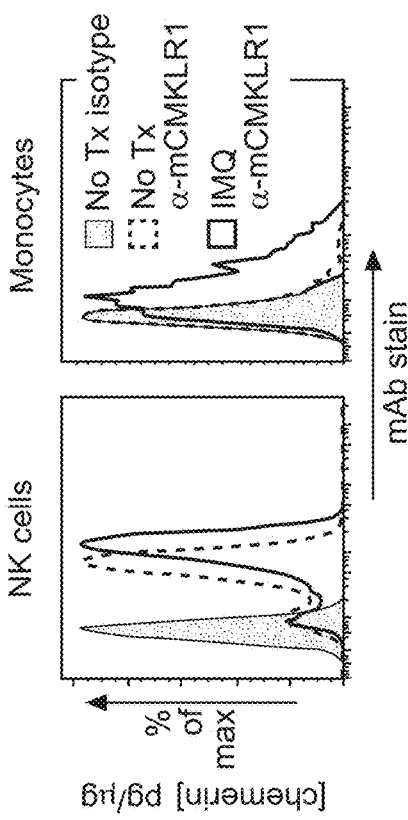
Figure 10C:
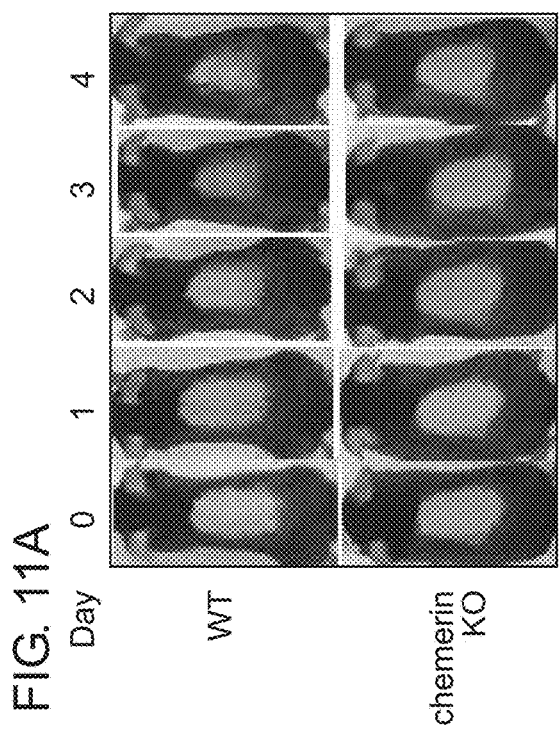
Figure 10D:
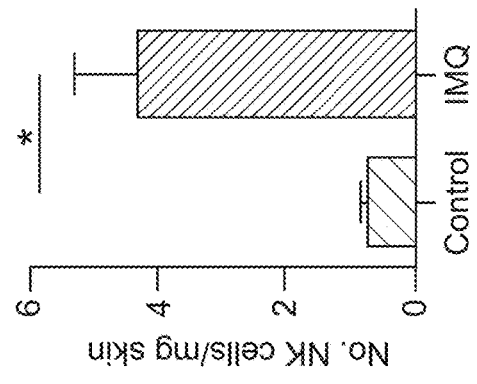
Figure 10E:
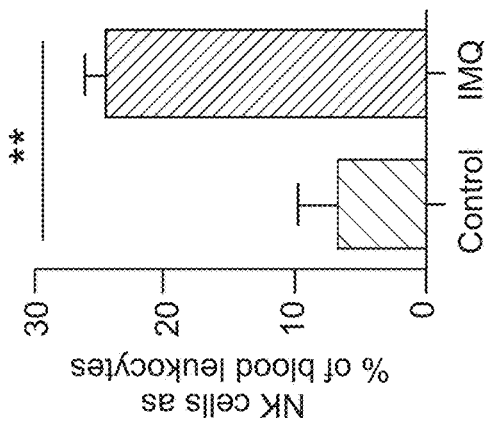

Characterization of chemerin and CMKLR1 in preclinical mouse psoriasis. In the IMQ-induced mouse model of psoriasis, chemerin protein and RNA were significantly upregulated in IMQ-treated skin vs. untreated skin in WT mice (FIG. 10A). We previously published that blood NK cells express CMKLR1 under homeostatic conditions. Blood NK cells from IMQ-treated mice (24 h treatment) also expressed CMKLR1 (FIG. 10B). IMQ treatment induced CMKLR1 expression on blood monocytes (FIG. 10B). CMKLR1 was functional on NK cells, as they migrated to chemerin in a dose-dependent manner, while CMKLR1-negative T and B lymphocytes did not, demonstrating attractant specificity (FIG. 10C). Furthermore, IMQ treatment induced a relative expansion of circulating NK cells and monocytes as a percentage of total leukocytes (FIG. 10D), and significant numbers of NK cells infiltrated the lesional skin (FIG. 10E). NK cells were reported to play a pathogenic role in psoriasis. Thus, similar to human psoriasis, our data in the IMQ-induced mouse model implicates a role for chemerin and its receptors in disease pathogenesis.

Figure 11A:
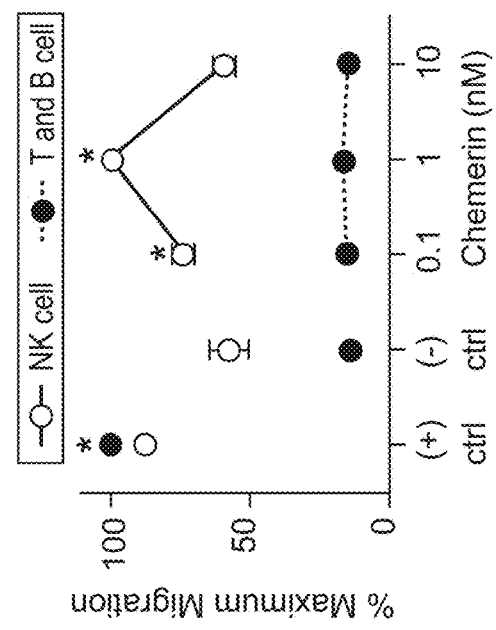

Attenuation of psoriasis in chemerin-deficient mice. Using our newly generated chemerin KO mouse, we next asked if chemerin deficiency had an impact on IMQ disease progression. Chemerin KO mice developed less severe clinical signs of psoriasis (reduced redness, flakiness, skin contraction) and significantly reduced acanthosis over time in the IMQ-psoriasis model (FIG. 11A, B). When compared with the inhibitory effects of global immune suppressant dexamethasone (which completely inhibited acanthosis from days 1-4 post-IMQ, and then inhibited 62±6% on day 5), chemerin deficiency inhibited skin thickening by 80±3% on day 5 post-IMQ, slightly better than the effects of DEX (FIG. 11C). Histological features of psoriasis induced by IMQ were also reduced in chemerin KO mice (FIG. 11D), with significant reductions in epidermal thickening (FIG. 11E) and dermal thickening (FIG. 11F) compared to WT. There were no genotype-dependent differences in epidermal or dermal thickness in non-lesional skin (FIG. 11E,F), implying that chemerin deficiency does not grossly alter normal microscopic skin features. There were significantly fewer NK cells as a percentage of total CD45+ leukocytes in IMQ-treated lesional skin from chemerin KO mice vs. WT (FIG. 11G). In IMQ-treated WT skin there was an elevated percentage of NK cells in lesional vs. non-lesional skin, whereas in chemerin KO mice there was a significant reduction (FIG. 11G). These preliminary data point to a specific defect in NK cell recruitment to lesional skin in chemerin KO mice.

Figure 12C:
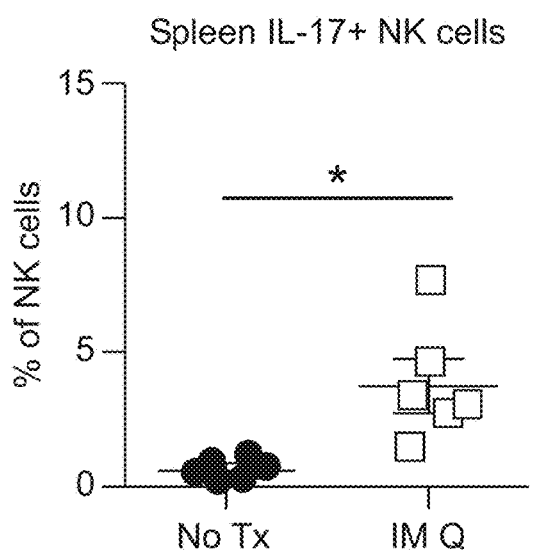
Figure 12D:
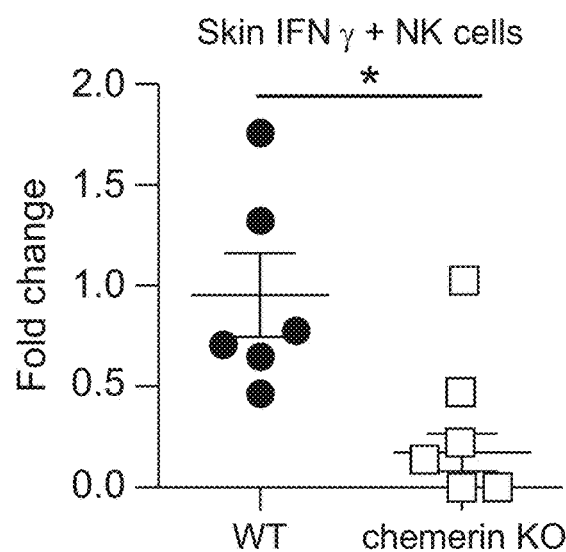
Figure 12E:
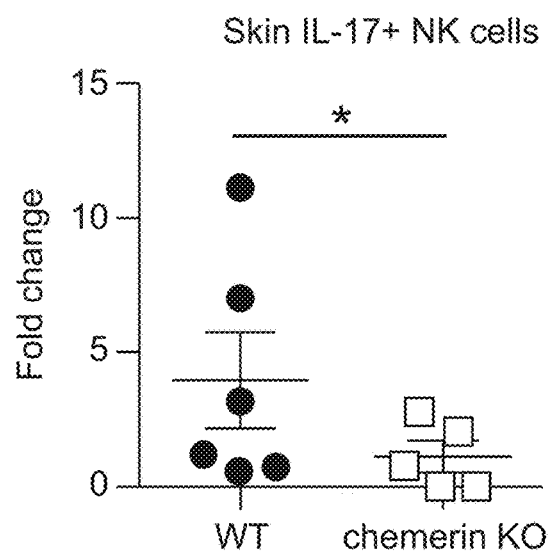

Chemerin drives NK cells recruitment into skin during psoriasis. NK cells are not well characterized in psoriasis, yet circumstantial evidence implies a relationship: increased numbers of NK cells are present in human lesional vs. non-lesional plaques, and lesional skin biopsies contain potent IFNγ producing NK cells. We therefore sought to investigate 1) the potential conversion of resting NK cells into pro-psoriatic cytokine-producing NK cells in IMQ-psoriasis, and 2) the role of chemerin in the recruitment of pro-psoriatic cytokine-positive NK cells into the skin. IMQ-treatment significantly induced IFNγ and IL-17 cytokine production by splenic NK cells as quantified by intracellular cytokine staining (FIG. 12A-C). There was no difference in the upregulation of IFNγ and IL-17 in splenic NK cells between WT and chemerin KO mice. However, the recruitment of IFNγ+ and IL-17+NK cells into the skin of chemerin KO mice was significantly impaired compared to WT (FIG. 12D,E). These data implicate a pathogenic role for NK cells as key cytokine producers in experimental psoriasis, and for chemerin in NK cell recruitment into inflamed skin.

Figure 13A:
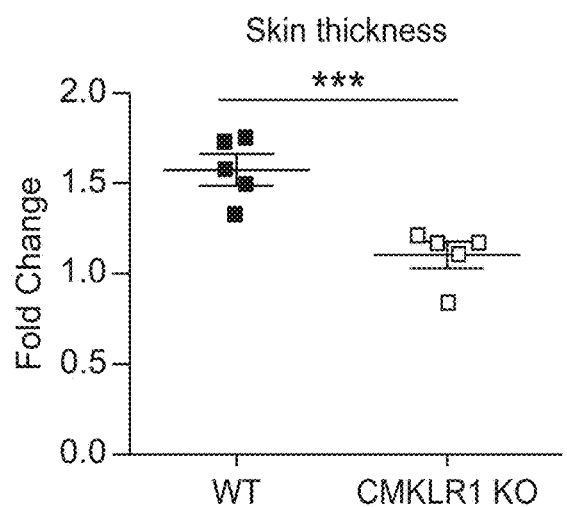
FIG. 13A-13D. Genetic or pharmaceutical targeting of CMKLR1 inhibits IMQ-induced psoriasis.
Figure 13B:
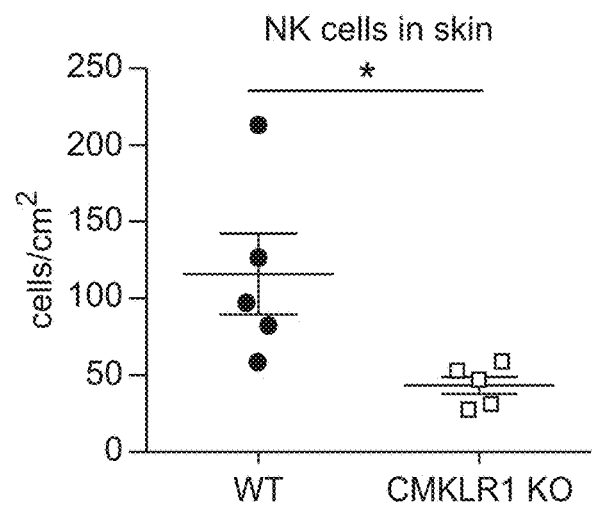
Figure 13C:
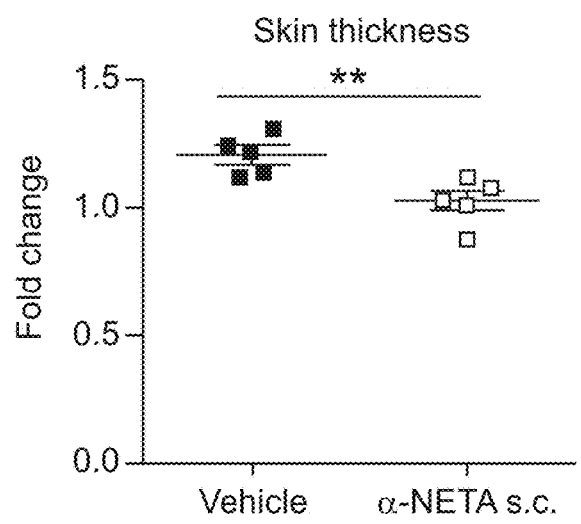
Figure 13D:
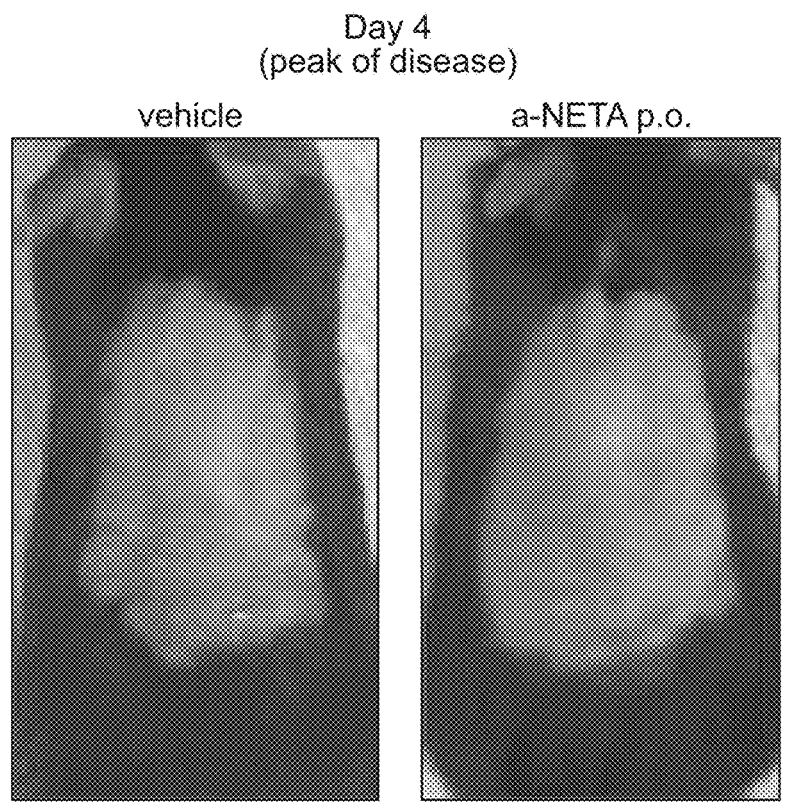
Figure 13D:
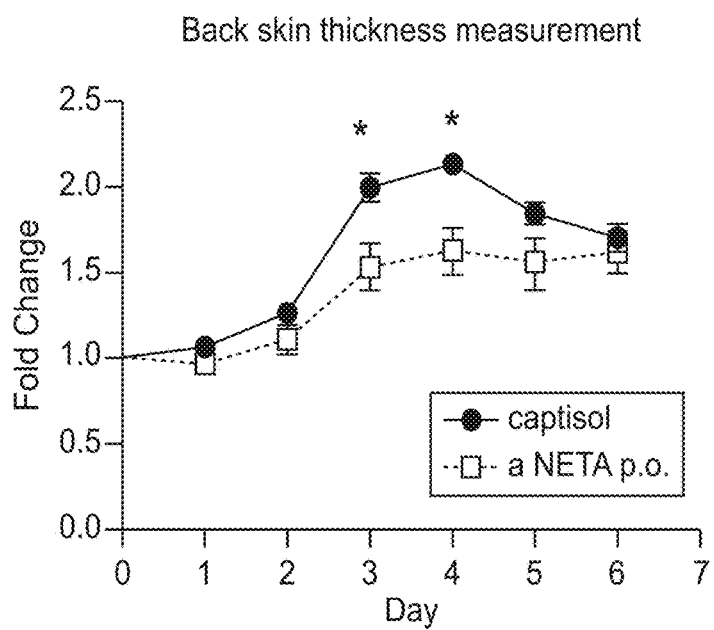
Figure 13D:
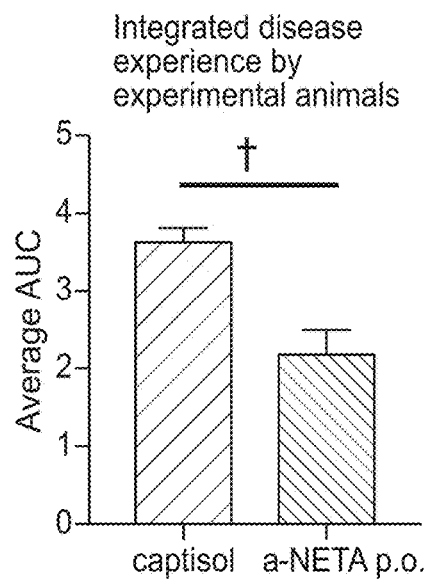

Both CMKLR1 genetic deficiency and treatment with CMKLR1 antagonist α-NETA protects against preclinical psoriasis. We next asked if targeting CMKLR1 by genetic deficiency or small molecule antagonism protects against experimental psoriasis. CMKLR1 KO mice developed less severe clinical signs of IMQ-induced psoriasis and significantly reduced acanthosis vs. WT (FIG. 13A). There were significantly fewer NK cells per square cm of IMQ-treated lesional skin from CMKLR1 KO mice vs. WT (FIG. 13B). It is possible, however, that CMKLR1 is required during fetal or neonatal development for some aspect of skin development unrelated to leukocyte trafficking that renders CMKLR1 KO mice resistant to psoriasis as an adult. Thus, testing CMKLR1 inhibitors in adult WT mice is important to directly assess the role of CMKLR1 in disease pathogenesis, and may have important translational implications. CMKLR1 antagonist α-NETA delivered s.c. significantly suppressed back skin thickening in the IMQ model (FIG. 13C). Since s.c. administration is not optimal for studies of skin disease, we also evaluated α-NETA for efficacy in suppressing psoriasis when administered by oral gavage. α-NETA p.o. reduced clinical signs of IMQ-induced psoriasis compared with vehicle control by visual inspection (reduction in redness and scales) and significantly diminished back skin acanthosis (FIG. 13D). Over time the α-NETA-treated mice experienced significantly less severe disease than their vehicle control treated counterparts (FIG. 13D).

Figure 14A:
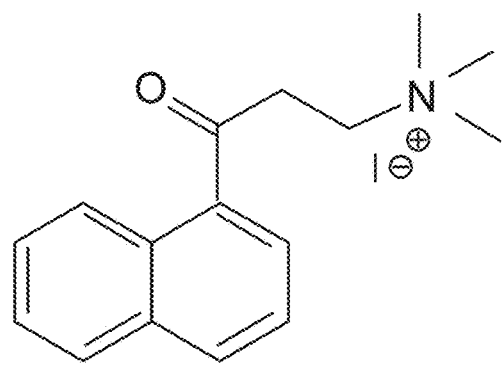
FIG. 14A-14D. Proof-of-concept SAR. α-NETA and selected analogs were tested for potency in inhibiting chemerin-mediated (20 nM) β-arrestin2 association with CMKLR1 in vitro in CHO transfectants (as detected by enzymatic complementation and quantified by chemiluminescence). IC50 values were determined based on 12-point dose-response curves for each compound.
Figure 14B:
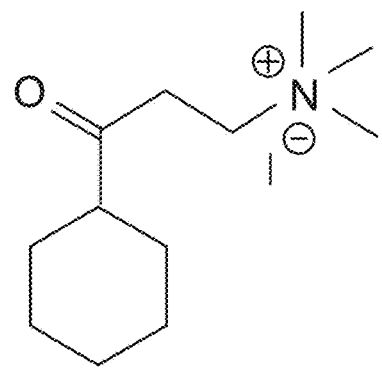
Figure 14C:
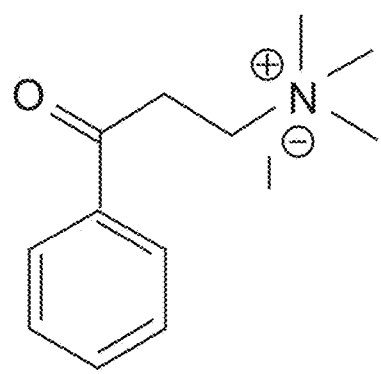
Figure 14D:
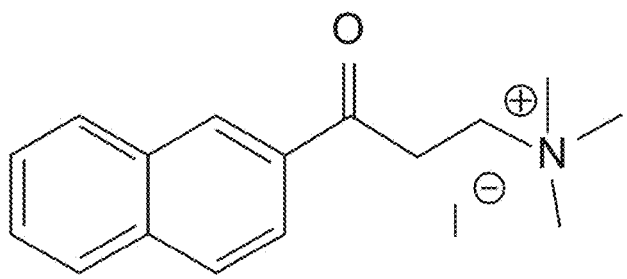

Structure-Activity Relationship (SAR). We next sought to understand how changes to the structure of α-NETA affect its activity in inhibiting chemerin-dependent CMKLR1 signaling, with the goal of generating analogs with improved target potency. α-NETA has four distinct potential sites of modification: ring structure, linker functionalization, alterations in alkyl chain linker, and ammonium salt modification. In preliminary studies, we generated 11 initial α-NETA analogs and determined $IC_{50}$ values for inhibition of chemerin-stimulated CMKLR1 signaling in vitro by β-arrestin assay. Ring modification to cyclohexane negatively impacted potency (FIG. 14A vs. B), whereas modification to benzene retained similar target potency (FIG. 14A vs. C). Shifting the side-chain to the β-carbon in naphthalene slightly improved the $IC_{50}$ value (FIG. 14A vs. D). This data provides proof-of-concept that we can derive important SAR by focused synthetic medicinal chemistry. It also provides proof-of-concept that we can generate analogs with similar or improved potency (compared with α-NETA), with potential to improve plasma stability, PK and in vivo efficacy.

Figure 15A:
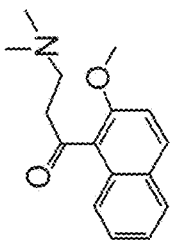
FIG. 15A-15D. SAR of improved α-NETA analogs and in vivo efficacy in suppressing experimental psoriasis. α-NETA and selected analogs were tested for potency in inhibiting chemerin-mediated (20 nM) β-arrestin2 association with CMKLR1 in vitro in CHO transfectants (as detected by enzymatic complementation and quantified by chemiluminescence) and chemerin-dependent (1 nM) CMKLR1+ cell chemotaxis in vitro. IC50 values were determined based on 6-point dose-response curves for each compound.
Figure 15B:
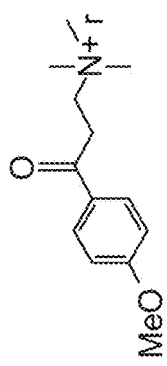
Figure 15C:
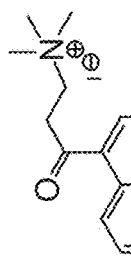
Figure 15D:
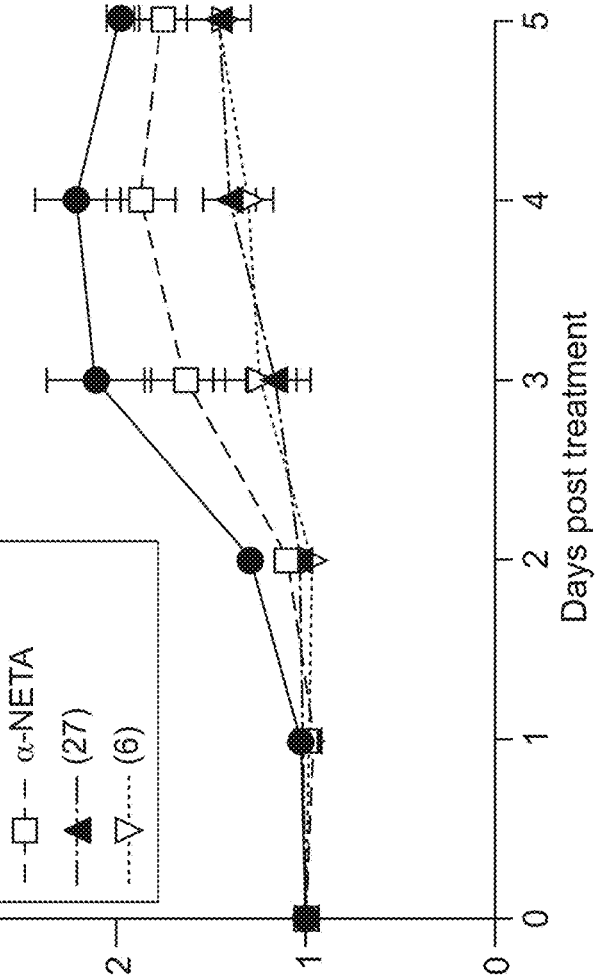
Figure 16:
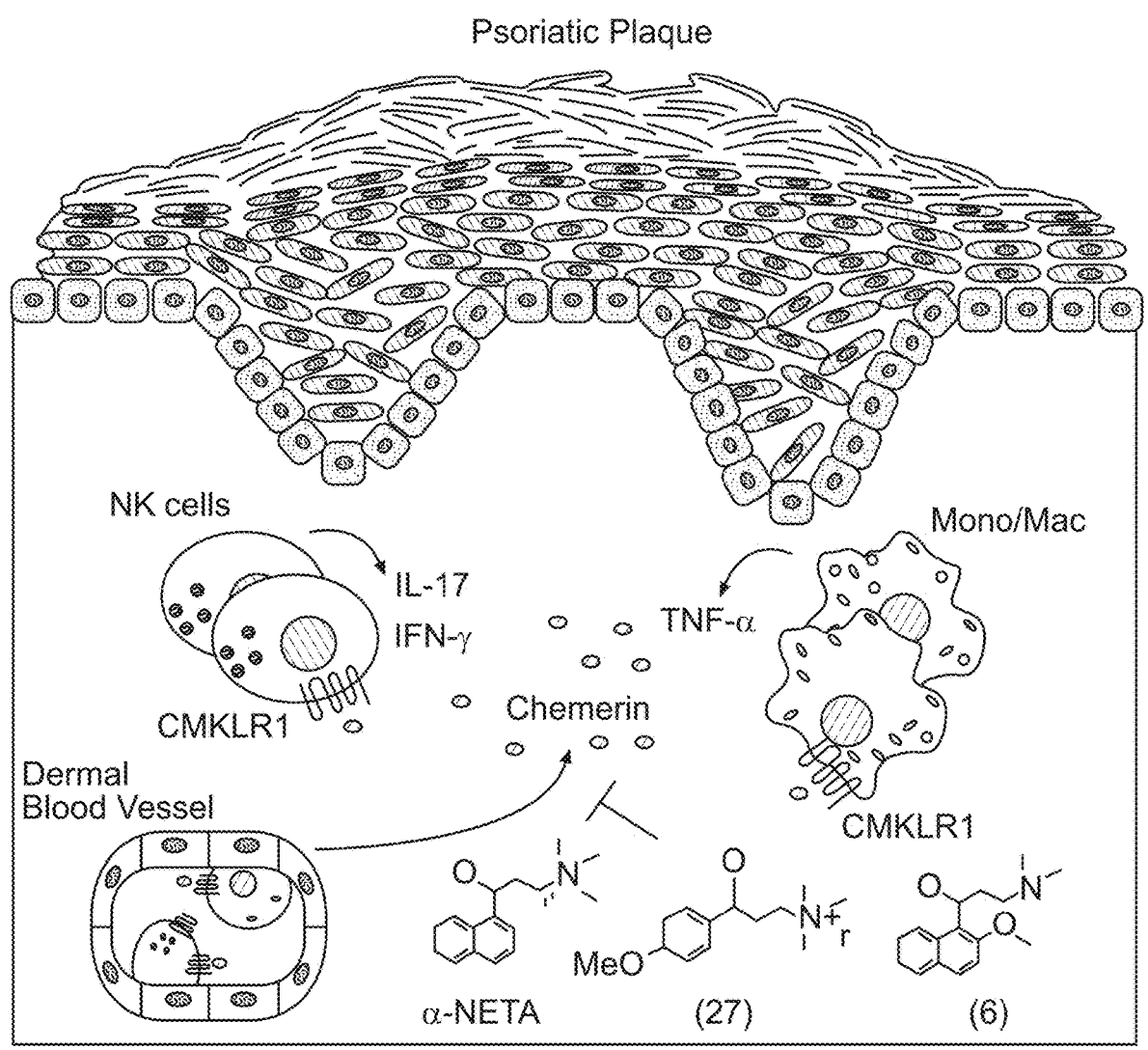
FIG. 16. Model of chemerin, CMKLR1, and α-NETA/analogs in the pathogenesis of psoriasis. The defining microscopic features of psoriatic plaques include an infiltration of immune cells in the dermis, increased dermal vascularity, and a substantially thickened epidermis with atypical keratinocyte differentiation. We hypothesize that chemerin and its receptor CMKLR1 drive the pathogenesis of psoriasis via recruitment of pathogenic leukocytes (specifically NK cells and monocytes/macrophages) into affected skin. CMKLR1 antagonist α-NETA and its improved analogs (27) and (6) interfere with the disease process and ameliorates psoriasis.

SAR testing of an additional ~70 α-NETA analogs identified two new lead compounds, (27) and (6), which have similar (6) or improved (27) potency in inhibiting chemerin-stimulated β-arrestin signaling and chemotaxis (FIG. 15A-C). (6) is an uncharged α-NETA analog and thus has substantially different pharmacologic properties that may improve its pharmacokinetic properties. Importantly, α-NETA, (27), and (6) suppressed clinical features of experimental psoriasis in vivo (FIG. 15D). Based on the aggregate of data presented here, we propose a model where chemerin and CMKLR1 drive the pathogenesis of psoriasis via coordinated skin recruitment of pro-psoriatic CMKLR1+ leukocytes, and that we can ameliorate psoriasis with CMKLR1 antagonist α-NETA and its improved analogs to block pathogenic leukocyte skin infiltration (FIG. 16). α-NETA and its improved analogs hold great translational potential to reduce the impact of psoriasis on public health.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of decreasing psoriasis in a subject, the method comprising:
administering to said subject an effective amount of a compound selected from

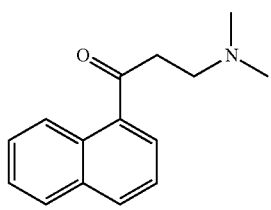

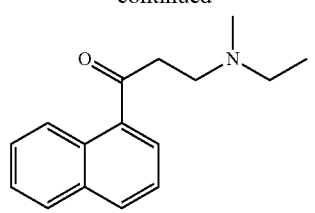

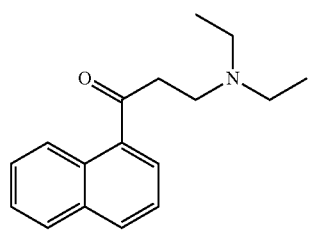

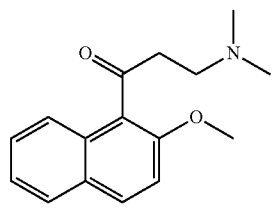

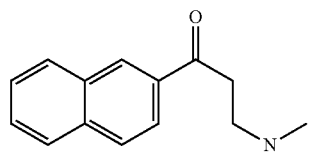

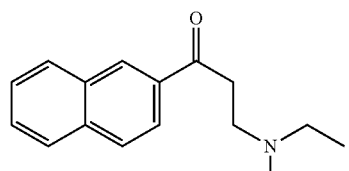

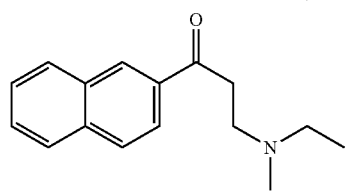

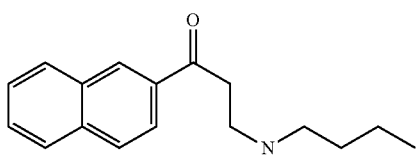

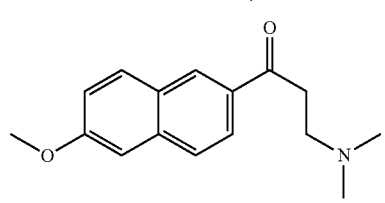

-continued

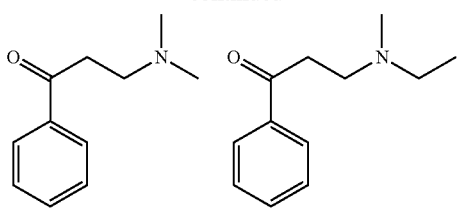

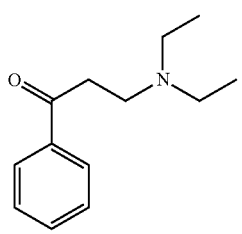

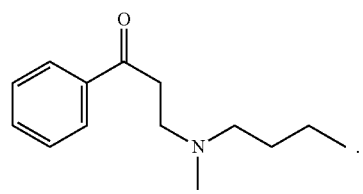

2. A method of decreasing psoriasis in a subject, the method comprising:

administering to said subject an effective amount of a compound

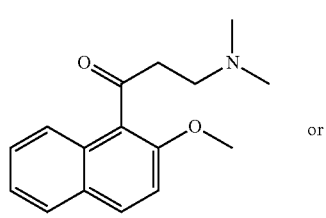 or

-continued

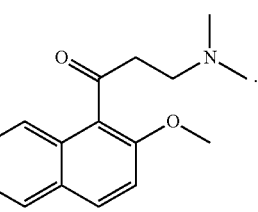

3. The method of claim 1, wherein the effective dose is from 0.01 mg/m² surface area to 500 mg/m² surface area.

4. The method of claim 1, wherein acanthosis is reduced by the treatment.

5. The method of claim 1, wherein the compound of Formula I has the structure:

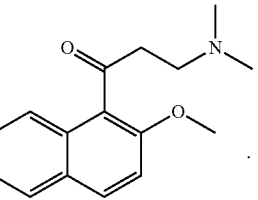

6. A method of treating psoriasis in a subject, the method comprising:

administering to the subject an effective dose of a compound having a structure:

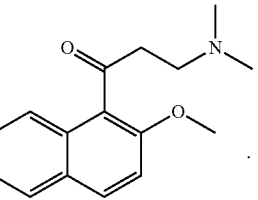

7. The method of claim 6, wherein the effective dose is from 0.01 mg/m² surface area to 500 mg/m² surface area.

8. The method of claim 6, wherein acanthosis is reduced by the treatment.

* * * * *